(12) United States Patent
Gilson et al.

(10) Patent No.: US 7,846,176 B2
(45) Date of Patent: *Dec. 7, 2010

(54) EMBOLIC PROTECTION SYSTEM

(75) Inventors: Paul Gilson, Moycullen (IE); Charles Taylor, West Sussex (GB); Patrick Griffin, Castlegar (IE); Michael Gilvarry, Ballina (IE); David Vale, Dublin (IE); Eamon Brady, Elphin (IE)

(73) Assignee: Salviac Limited, Dublin (IE)

( * ) Notice: Subject to any disclaimer, the term of this patent is extended or adjusted under 35 U.S.C. 154(b) by 220 days.

This patent is subject to a terminal disclaimer.

(21) Appl. No.: 11/669,460

(22) Filed: Jan. 31, 2007

(65) Prior Publication Data

US 2007/0123931 A1 May 31, 2007

Related U.S. Application Data

(63) Continuation of application No. 10/939,995, filed on Sep. 14, 2004, now abandoned, which is a continuation of application No. 09/838,544, filed on Apr. 20, 2001, now Pat. No. 6,887,256, which is a continuation-in-part of application No. 09/188,472, filed on Nov. 9, 1998, now Pat. No. 6,336,934.

(30) Foreign Application Priority Data

| Nov. 7, 1997 | (IE) | ................................. 970789 |
| Apr. 8, 1998 | (IE) | ................................. 980267 |
| Apr. 20, 2000 | (IE) | ........................ PCT/IE00/00045 |
| Mar. 16, 2001 | (IE) | ............................... 2001/0258 |
| Mar. 16, 2001 | (IE) | ............................... 2001/0260 |
| Mar. 16, 2001 | (IE) | ............................... 2001/0261 |

(51) Int. Cl.
*A61M 29/00* (2006.01)

(52) U.S. Cl. ................................... 606/200

(58) Field of Classification Search ................. 606/127, 606/128, 159, 194–200, 108; 604/104–107; 128/898; 623/1.11, 1.12, 903
See application file for complete search history.

(56) References Cited

U.S. PATENT DOCUMENTS 2,854,983 A 10/1958 Barskin (Continued)

FOREIGN PATENT DOCUMENTS

DE 3706077 6/1988

(Continued)

OTHER PUBLICATIONS

A. Beck et al., "Dilatation of the Carotid Artery by a Temporary Carotid Filter", Edizioni Oplitai—Via dei Foscari N° 7 -00162 Roma, Spediz, in Abb. Postale Gruppo IV—70%—Anno II N. 6 Nov.-Dec. 1989 L. 800.

(Continued)

*Primary Examiner*—Anhtuan T Nguyen
*Assistant Examiner*—Elizabeth Houston
(74) *Attorney, Agent, or Firm*—Sughrue Mion, PLLC; Jonathan Feuchtwang

(57) ABSTRACT

An assembly for loading a collapsible embolic protection filter 1 into a catheter 2, comprises a catheter 2 defining a reception space at a distal end of the catheter 2 for receiving a collapsed embolic protection filter 1; and a separate removable pushing device 8 for delivering the embolic protection filter 1 into the reception space. The pushing device 8 comprises an elongate stem 71 with a proximal stop 72 for engagement with the filter 1. A separate loading device 7 to collapse the embolic protection filter 1 is also provided. The loading device 7 defines an inlet end and an outlet end, the outlet end being configured for co-operative alignment with the reception space.

10 Claims, 35 Drawing Sheets

U.S. PATENT DOCUMENTS

| | | |
|---|---|---|
| 2,943,626 A | 7/1960 | Dormia |
| 3,334,629 A | 8/1967 | Cohn |
| 3,435,824 A | 4/1969 | Gamponia |
| 3,540,431 A | 11/1970 | Mebin-Uddin |
| 3,692,029 A | 9/1972 | Adair |
| 3,730,185 A | 5/1973 | Cook et al. |
| 3,952,747 A | 4/1976 | Kimmell, Jr. |
| 4,295,464 A | 10/1981 | Shihata |
| 4,404,971 A | 9/1983 | LeVeen et al. |
| 4,423,725 A | 1/1984 | Baran et al. |
| 4,425,908 A | 1/1984 | Simon |
| 4,425,909 A | 1/1984 | Rieser |
| 4,445,892 A | 5/1984 | Hussein et al. |
| 4,493,711 A | 1/1985 | Chin et al. |
| 4,512,762 A | 4/1985 | Spears |
| 4,585,000 A | 4/1986 | Hershenson |
| 4,586,919 A | 5/1986 | Taheri |
| 4,610,662 A | 9/1986 | Weikl et al. |
| 4,611,594 A | 9/1986 | Grayhack et al. |
| 4,619,246 A | 10/1986 | Molgaard-Nielsen et al. |
| 4,643,187 A | 2/1987 | Okada |
| 4,650,466 A | 3/1987 | Luther |
| 4,712,551 A | 12/1987 | Rayhunabad |
| 4,723,549 A | 2/1988 | Wholey et al. |
| 4,781,177 A | 11/1988 | Lebigot |
| 4,790,812 A | 12/1988 | Hawkins, Jr. et al. |
| 4,794,928 A | 1/1989 | Kletschka |
| 4,807,626 A | 2/1989 | McGirr |
| 4,817,600 A | 4/1989 | Herms et al. |
| 4,832,055 A | 5/1989 | Palestrant |
| 4,867,156 A | 9/1989 | Stack et al. |
| 4,873,978 A | 10/1989 | Ginsburg |
| 4,926,858 A | 5/1990 | Gifford, III et al. |
| 4,927,426 A | 5/1990 | Dretler |
| 4,957,501 A | 9/1990 | Lahille et al. |
| 4,969,891 A | 11/1990 | Gevertz |
| 4,990,156 A | 2/1991 | Lefebvre |
| 5,011,488 A | 4/1991 | Ginsburg |
| 5,026,377 A | 6/1991 | Burton et al. |
| 5,053,008 A | 10/1991 | Bajaj |
| 5,092,839 A | 3/1992 | Kipperman |
| 5,100,423 A | 3/1992 | Fearnot |
| 5,108,419 A | 4/1992 | Reger et al. |
| 5,122,125 A | 6/1992 | Deuss |
| 5,133,733 A | 7/1992 | Rasmussen et al. |
| 5,171,233 A | 12/1992 | Amplatz et al. |
| 5,178,158 A | 1/1993 | de Toledo |
| 5,192,284 A | 3/1993 | Pleatman |
| 5,254,622 A | 10/1993 | Nanasawa et al. |
| 5,324,304 A | 6/1994 | Rasmussen |
| 5,329,942 A | 7/1994 | Gunther et al. |
| 5,336,234 A | 8/1994 | Vigil et al. |
| 5,354,310 A | 10/1994 | Garnic et al. |
| 5,370,657 A | 12/1994 | Irie |
| 5,375,612 A | 12/1994 | Cottenceau et al. |
| 5,383,887 A | 1/1995 | Nadal |
| 5,387,219 A | 2/1995 | Rappe |
| 5,405,329 A | 4/1995 | Durand |
| 5,421,832 A * | 6/1995 | Lefebvre ............... 264/173.11 |
| 5,454,788 A | 10/1995 | Walker et al. |
| 5,490,837 A * | 2/1996 | Blaeser et al. ......... 604/103.11 |
| 5,540,707 A | 7/1996 | Ressemenn et al. |
| 5,549,626 A | 8/1996 | Miller et al. |
| 5,593,394 A | 1/1997 | Kanesaka et al. |
| 5,621,065 A | 4/1997 | Pudleiner et al. |
| 5,658,296 A | 8/1997 | Bates et al. |
| 5,662,671 A | 9/1997 | Barbut et al. |
| 5,669,933 A | 9/1997 | Simon et al. |
| 5,683,451 A | 11/1997 | Lenker et al. |
| 5,695,519 A | 12/1997 | Summers et al. |
| 5,709,704 A | 1/1998 | Nott et al. |
| 5,713,853 A * | 2/1998 | Clark et al. ................. 604/509 |
| 5,720,764 A | 2/1998 | Naderlinger |
| 5,725,519 A | 3/1998 | Penner et al. |
| 5,766,203 A | 6/1998 | Imran et al. |
| 5,769,816 A | 6/1998 | Barbut et al. |
| 5,769,871 A | 6/1998 | Mers Kelly et al. |
| 5,779,716 A | 7/1998 | Cano et al. |
| 5,795,322 A | 8/1998 | Boudewijn |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,823,992 A | 10/1998 | Salmon et al. |
| 5,827,324 A | 10/1998 | Cassell et al. |
| 5,834,449 A | 11/1998 | Thompson et al. |
| 5,836,969 A | 11/1998 | Kim et al. |
| 5,843,167 A | 12/1998 | Dwyer et al. |
| 5,846,260 A | 12/1998 | Maahs |
| 5,848,964 A | 12/1998 | Samuels |
| 5,876,367 A | 3/1999 | Kaganov et al. |
| 5,879,697 A | 3/1999 | Ding et al. |
| 5,882,329 A | 3/1999 | Patterson et al. |
| 5,895,398 A | 4/1999 | Wensel et al. |
| 5,895,410 A | 4/1999 | Forber et al. |
| 5,897,567 A | 4/1999 | Ressemann et al. |
| 5,902,334 A | 5/1999 | Dwyer et al. |
| 5,910,154 A | 6/1999 | Tsugita et al. |
| 5,911,725 A | 6/1999 | Boury |
| 5,911,734 A | 6/1999 | Tsugita et al. |
| 5,928,261 A | 7/1999 | Ruiz |
| 5,935,139 A | 8/1999 | Bates |
| 5,941,869 A | 8/1999 | Patterson et al. |
| 5,941,896 A | 8/1999 | Kerr |
| 5,947,995 A | 9/1999 | Samuels |
| 5,954,745 A | 9/1999 | Gertler et al. |
| 5,968,071 A | 10/1999 | Chevillon |
| 5,976,172 A | 11/1999 | Homsma et al. |
| 5,984,947 A | 11/1999 | Smith |
| 5,989,281 A | 11/1999 | Barbut et al. |
| 5,993,469 A | 11/1999 | McKenzie et al. |
| 5,997,557 A | 12/1999 | Barbut et al. |
| 6,001,118 A | 12/1999 | Daniel et al. |
| 6,007,557 A | 12/1999 | Ambrisco et al. |
| 6,010,522 A | 1/2000 | Barbut et al. |
| 6,013,093 A | 1/2000 | Nott et al. |
| 6,027,509 A | 2/2000 | Schatz et al. |
| 6,027,520 A | 2/2000 | Tsugita et al. |
| 6,042,598 A | 3/2000 | Tsugita et al. |
| 6,048,645 A | 4/2000 | Tu |
| 6,051,014 A | 4/2000 | Jang |
| 6,053,832 A | 4/2000 | Saito |
| 6,053,932 A | 4/2000 | Daniel et al. |
| 6,059,814 A | 5/2000 | Ladd |
| 6,063,173 A | 5/2000 | Balceta et al. |
| 6,066,149 A | 5/2000 | Samson et al. |
| 6,074,357 A | 6/2000 | Kaganov et al. |
| 6,083,239 A | 7/2000 | Addis |
| 6,086,577 A | 7/2000 | Ken et al. |
| 6,086,605 A | 7/2000 | Barbut et al. |
| 6,090,097 A | 7/2000 | Barbut et al. |
| 6,096,027 A | 8/2000 | Layne |
| 6,096,053 A | 8/2000 | Bates |
| 6,099,534 A | 8/2000 | Bates et al. |
| 6,099,549 A | 8/2000 | Bosma et al. |
| 6,123,715 A | 9/2000 | Amplatz |
| 6,129,739 A | 10/2000 | Khosravi |
| 6,132,458 A | 10/2000 | Staehle et al. |
| 6,142,987 A | 11/2000 | Tsugita |
| 6,146,370 A * | 11/2000 | Barbut ........................ 604/500 |
| 6,146,404 A | 11/2000 | Kim et al. |
| 6,152,946 A * | 11/2000 | Broome et al. .............. 606/200 |
| 6,156,200 A | 12/2000 | Tsugita et al. |
| 6,168,579 B1 | 1/2001 | Tsugita |

| Patent No. | Date | Inventor(s) |
|---|---|---|
| 6,168,604 B1 | 1/2001 | Cano |
| 6,171,327 B1 | 1/2001 | Daniel et al. |
| 6,171,328 B1 | 1/2001 | Addis |
| 6,176,849 B1 | 1/2001 | Yang et al. |
| 6,179,859 B1 | 1/2001 | Bates et al. |
| 6,179,861 B1 | 1/2001 | Khosravi et al. |
| 6,203,561 B1 | 3/2001 | Ramee et al. |
| 6,206,868 B1 | 3/2001 | Parodi |
| 6,214,026 B1 | 4/2001 | Lepak et al. |
| 6,221,006 B1 * | 4/2001 | Dubrul et al. ............... 600/159 |
| 6,238,412 B1 | 5/2001 | Dubrul et al. |
| 6,241,746 B1 | 6/2001 | Bosma et al. |
| 6,245,012 B1 * | 6/2001 | Kleshinski ................ 623/1.11 |
| 6,245,087 B1 | 6/2001 | Addis |
| 6,245,088 B1 | 6/2001 | Lowery |
| 6,245,089 B1 | 6/2001 | Daniel et al. |
| 6,251,122 B1 | 6/2001 | Tsukernik |
| 6,254,563 B1 | 7/2001 | Macoviak et al. |
| 6,258,115 B1 | 7/2001 | Dubrul |
| 6,258,120 B1 | 7/2001 | McKenzie et al. |
| 6,264,663 B1 | 7/2001 | Cano |
| 6,264,672 B1 | 7/2001 | Fisher |
| 6,267,776 B1 | 7/2001 | O'Connell |
| 6,267,777 B1 | 7/2001 | Bosma et al. |
| 6,270,513 B1 | 8/2001 | Tsugita et al. |
| 6,273,901 B1 | 8/2001 | Whitcher et al. |
| 6,277,138 B1 | 8/2001 | Levinson et al. |
| 6,277,139 B1 | 8/2001 | Levinson et al. |
| 6,280,413 B1 * | 8/2001 | Clark et al. ................ 604/104 |
| 6,290,710 B1 | 9/2001 | Cryer et al. |
| 6,295,989 B1 | 10/2001 | Connors, III |
| 6,306,163 B1 | 10/2001 | Fitz |
| 6,319,242 B1 | 11/2001 | Patterson et al. |
| 6,325,815 B1 | 12/2001 | Kusleika et al. |
| 6,336,934 B1 | 1/2002 | Gilson et al. |
| 6,340,364 B2 | 1/2002 | Kanesaka |
| 6,346,116 B1 | 2/2002 | Brooks et al. |
| 6,348,056 B1 | 2/2002 | Bates et al. |
| 6,355,051 B1 | 3/2002 | Sisskind et al. |
| 6,361,545 B1 | 3/2002 | Macoviak et al. |
| 6,361,546 B1 | 3/2002 | Khosravi |
| 6,364,895 B1 | 4/2002 | Greenhalgh |
| 6,371,935 B1 | 4/2002 | Macoviak et al. |
| 6,371,969 B1 | 4/2002 | Tsugita et al. |
| 6,371,970 B1 | 4/2002 | Khosravi et al. |
| 6,371,971 B1 | 4/2002 | Tsugita et al. |
| 6,375,670 B1 | 4/2002 | Greenhalgh |
| 6,383,206 B1 | 5/2002 | Gillick et al. |
| 6,391,044 B1 | 5/2002 | Yadav et al. |
| 6,394,978 B1 | 5/2002 | Boyle et al. |
| 6,395,014 B1 | 5/2002 | Macoviak et al. |
| 6,395,017 B1 | 5/2002 | Dwyer et al. |
| 6,398,756 B2 | 6/2002 | Peterson et al. |
| 6,402,771 B1 | 6/2002 | Palmer et al. |
| 6,406,471 B1 | 6/2002 | Jang et al. |
| 6,423,032 B2 | 7/2002 | Parodi |
| 6,425,909 B1 | 7/2002 | Dieck et al. |
| 6,428,559 B1 | 8/2002 | Johnson |
| 6,432,122 B1 | 8/2002 | Gilson et al. |
| 6,436,121 B1 | 8/2002 | Blom |
| 6,443,926 B1 | 9/2002 | Kletschka |
| 6,443,971 B1 | 9/2002 | Boylan et al. |
| 6,443,979 B1 | 9/2002 | Stalker et al. |
| 6,447,530 B1 | 9/2002 | Ostrovsky et al. |
| 6,458,139 B1 | 10/2002 | Palmer et al. |
| 6,461,370 B1 | 10/2002 | Gray et al. |
| 6,468,291 B2 | 10/2002 | Bates et al. |
| 6,482,222 B1 | 11/2002 | Bruckheimer et al. |
| 6,485,497 B2 | 11/2002 | Wensel et al. |
| 6,485,500 B1 | 11/2002 | Kokish et al. |
| 6,485,501 B1 | 11/2002 | Green |
| 6,485,502 B2 | 11/2002 | Don Michael et al. |
| 6,494,895 B2 | 12/2002 | Addis |
| 6,506,203 B1 | 1/2003 | Boyle et al. |
| 6,506,205 B2 | 1/2003 | Goldberg et al. |
| 6,511,492 B1 * | 1/2003 | Rosenbluth et al. ......... 606/159 |
| 6,511,496 B1 | 1/2003 | Huter et al. |
| 6,511,497 B1 | 1/2003 | Braun et al. |
| 6,511,503 B1 | 1/2003 | Burkett et al. |
| 6,514,273 B1 | 2/2003 | Voss et al. |
| 6,517,550 B1 | 2/2003 | Konya et al. |
| 6,517,559 B1 | 2/2003 | O'Connell |
| 6,520,978 B1 | 2/2003 | Blackledge et al. |
| 6,527,746 B1 | 3/2003 | Oslund et al. |
| 6,530,939 B1 | 3/2003 | Hopkins et al. |
| 6,530,940 B2 | 3/2003 | Fisher |
| 6,533,800 B1 | 3/2003 | Barbut |
| 6,537,294 B1 | 3/2003 | Boyle et al. |
| 6,537,295 B2 | 3/2003 | Petersen |
| 6,537,296 B2 | 3/2003 | Levinson et al. |
| 6,537,297 B2 | 3/2003 | Tsugita et al. |
| 6,540,722 B1 | 4/2003 | Boyle et al. |
| 6,540,767 B1 | 4/2003 | Walak et al. |
| 6,540,768 B1 | 4/2003 | Diaz et al. |
| 6,544,279 B1 | 4/2003 | Hopkins et al. |
| 6,544,280 B1 | 4/2003 | Daniel et al. |
| 6,547,760 B1 | 4/2003 | Samson et al. |
| 6,551,341 B2 | 4/2003 | Boylan et al. |
| 6,551,342 B1 | 4/2003 | Shen et al. |
| 6,558,405 B1 | 5/2003 | McInnes |
| 6,562,058 B2 | 5/2003 | Seguin |
| 6,565,591 B2 | 5/2003 | Brady et al. |
| 6,569,184 B2 | 5/2003 | Huter |
| 6,575,995 B1 | 6/2003 | Huter et al. |
| 6,575,996 B1 | 6/2003 | Denison et al. |
| 6,575,997 B1 | 6/2003 | Palmer et al. |
| 6,582,447 B1 | 6/2003 | Patel et al. |
| 6,582,448 B1 | 6/2003 | Boyle et al. |
| 6,585,756 B1 | 7/2003 | Strecker |
| 6,589,263 B1 | 7/2003 | Hopkins et al. |
| 6,589,265 B1 | 7/2003 | Palmer et al. |
| 6,592,546 B1 | 7/2003 | Barbut et al. |
| 6,592,606 B2 | 7/2003 | Huter et al. |
| 6,592,616 B1 | 7/2003 | Stack et al. |
| 6,596,011 B2 | 7/2003 | Johnson et al. |
| 6,599,307 B1 | 7/2003 | Huter et al. |
| 6,602,269 B2 | 8/2003 | Wallace et al. |
| 6,602,271 B2 | 8/2003 | Adams et al. |
| 6,602,272 B2 | 8/2003 | Boylan et al. |
| 6,605,102 B1 | 8/2003 | Mazzocchi et al. |
| 6,605,111 B2 | 8/2003 | Bose et al. |
| 6,610,077 B1 | 8/2003 | Hancock et al. |
| 6,616,679 B1 | 9/2003 | Khosravi et al. |
| 6,616,680 B1 | 9/2003 | Thielen |
| 6,616,681 B2 | 9/2003 | Hanson et al. |
| 6,616,682 B2 | 9/2003 | Joergensen et al. |
| 6,620,148 B1 | 9/2003 | Tsugita et al. |
| 6,620,182 B1 | 9/2003 | Khosravi |
| 6,623,450 B1 | 9/2003 | Dutta |
| 6,632,236 B2 | 10/2003 | Hogendijk |
| 6,632,241 B1 | 10/2003 | Hancock et al. |
| 6,635,070 B2 | 10/2003 | Leeflang et al. |
| 6,638,294 B1 | 10/2003 | Palmer |
| 6,645,220 B1 | 11/2003 | Huter et al. |
| 6,645,223 B2 | 11/2003 | Boyle et al. |
| 6,645,224 B2 | 11/2003 | Gilson et al. |
| 6,652,480 B1 | 11/2003 | Imran et al. |
| 6,652,505 B1 | 11/2003 | Tsugita et al. |
| 6,652,554 B1 | 11/2003 | Wholey et al. |
| 6,652,557 B1 | 11/2003 | MacDonald |
| 6,656,202 B2 | 12/2003 | Papp et al. |
| 6,660,021 B1 | 12/2003 | Palmer et al. |
| 6,663,650 B2 | 12/2003 | Sepetka et al. |
| 6,663,651 B2 | 12/2003 | Krolik et al. |
| 6,663,652 B2 | 12/2003 | Daniel et al. |
| 6,682,812 B2 | 1/2004 | Scheckenbach et al. |

| | | |
|---|---|---|
| 6,726,703 B2 | 4/2004 | Broome et al. |
| 6,752,819 B1 | 6/2004 | Brady et al. |
| 6,755,846 B1 * | 6/2004 | Yadav ........................ 606/200 |
| 6,782,216 B2 | 8/2004 | Daniel et al. |
| 6,887,256 B2 | 5/2005 | Gilson et al. |
| 2001/0000799 A1 | 5/2001 | Wessman et al. |
| 2001/0001315 A1 | 5/2001 | Bates et al. |
| 2001/0007947 A1 | 7/2001 | Kanesaka |
| 2001/0012951 A1 | 8/2001 | Bates et al. |
| 2001/0020175 A1 | 9/2001 | Yassour et al. |
| 2001/0025187 A1 | 9/2001 | Okada |
| 2001/0031982 A1 | 10/2001 | Peterson et al. |
| 2001/0039431 A1 | 11/2001 | De Vries et al. |
| 2001/0041908 A1 | 11/2001 | Levinson et al. |
| 2001/0044632 A1 | 11/2001 | Daniel et al. |
| 2002/0002384 A1 | 1/2002 | Gilson et al. |
| 2002/0022858 A1 | 2/2002 | Demond et al. |
| 2002/0022860 A1 | 2/2002 | Borillo et al. |
| 2002/0026211 A1 | 2/2002 | Khosravi et al. |
| 2002/0026213 A1 | 2/2002 | Gilson et al. |
| 2002/0032460 A1 | 3/2002 | Kusleika et al. |
| 2002/0045916 A1 | 4/2002 | Gray et al. |
| 2002/0045918 A1 | 4/2002 | Suon et al. |
| 2002/0049467 A1 | 4/2002 | Gilson et al. |
| 2002/0049468 A1 | 4/2002 | Strecker et al. |
| 2002/0052626 A1 | 5/2002 | Gilson et al. |
| 2002/0052638 A1 | 5/2002 | Zadno-Azizi |
| 2002/0055747 A1 | 5/2002 | Cano et al. |
| 2002/0055767 A1 | 5/2002 | Forde et al. |
| 2002/0058911 A1 | 5/2002 | Gilson et al. |
| 2002/0058963 A1 | 5/2002 | Vale et al. |
| 2002/0062133 A1 | 5/2002 | Gilson et al. |
| 2002/0062135 A1 | 5/2002 | Mazzocchi et al. |
| 2002/0065507 A1 | 5/2002 | Zadno-Azizi |
| 2002/0068954 A1 | 6/2002 | Foster |
| 2002/0068955 A1 | 6/2002 | Khosravi |
| 2002/0072730 A1 | 6/2002 | McGill et al. |
| 2002/0072765 A1 | 6/2002 | Mazzocchi et al. |
| 2002/0082525 A1 | 6/2002 | Oslund et al. |
| 2002/0082639 A1 | 6/2002 | Broome et al. |
| 2002/0091408 A1 | 7/2002 | Sutton et al. |
| 2002/0091409 A1 | 7/2002 | Sutton et al. |
| 2002/0095141 A1 | 7/2002 | Belef et al. |
| 2002/0095170 A1 | 7/2002 | Krolik et al. |
| 2002/0095171 A1 | 7/2002 | Belef |
| 2002/0095172 A1 | 7/2002 | Mazzocchi et al. |
| 2002/0095173 A1 | 7/2002 | Mazzocchi et al. |
| 2002/0095174 A1 | 7/2002 | Tsugita et al. |
| 2002/0099407 A1 | 7/2002 | Becker et al. |
| 2002/0103501 A1 | 8/2002 | Diaz et al. |
| 2002/0107541 A1 | 8/2002 | Vale et al. |
| 2002/0111648 A1 | 8/2002 | Kusleika et al. |
| 2002/0111649 A1 | 8/2002 | Russo et al. |
| 2002/0115942 A1 | 8/2002 | Stanford et al. |
| 2002/0120286 A1 | 8/2002 | Dobrava et al. |
| 2002/0120287 A1 | 8/2002 | Huter |
| 2002/0121472 A1 | 9/2002 | Garner et al. |
| 2002/0123720 A1 | 9/2002 | Kuleika et al. |
| 2002/0123755 A1 | 9/2002 | Lowe et al. |
| 2002/0128679 A1 | 9/2002 | Turovskiy et al. |
| 2002/0128680 A1 | 9/2002 | Pavlovic |
| 2002/0128681 A1 | 9/2002 | Broome et al. |
| 2002/0133092 A1 | 9/2002 | Oslund et al. |
| 2002/0138094 A1 | 9/2002 | Borillo et al. |
| 2002/0138095 A1 | 9/2002 | Mazzocchi et al. |
| 2002/0143360 A1 | 10/2002 | Douk et al. |
| 2002/0143361 A1 | 10/2002 | Douk et al. |
| 2002/0151927 A1 | 10/2002 | Douk et al. |
| 2002/0156456 A1 | 10/2002 | Fisher |
| 2002/0156457 A1 | 10/2002 | Fisher |
| 2002/0161390 A1 | 10/2002 | Mouw |
| 2002/0161392 A1 | 10/2002 | Dubrul |
| 2002/0161393 A1 | 10/2002 | Demond et al. |
| 2002/0161395 A1 | 10/2002 | Douk et al. |
| 2002/0165576 A1 | 11/2002 | Boyle et al. |
| 2002/0169414 A1 | 11/2002 | Kletschka |
| 2002/0169458 A1 | 11/2002 | Connors, III |
| 2002/0169472 A1 | 11/2002 | Douk et al. |
| 2002/0169474 A1 | 11/2002 | Kusleika et al. |
| 2002/0173815 A1 | 11/2002 | Hogendijk et al. |
| 2002/0173817 A1 | 11/2002 | Kletschka et al. |
| 2002/0183873 A1 | 12/2002 | Shadduck |
| 2002/0188313 A1 | 12/2002 | Johnson et al. |
| 2002/0188314 A1 | 12/2002 | Anderson et al. |
| 2002/0193825 A1 | 12/2002 | McGuckin et al. |
| 2002/0193826 A1 | 12/2002 | McGuckin et al. |
| 2002/0193827 A1 | 12/2002 | McGuckin et al. |
| 2002/0193828 A1 | 12/2002 | Griffin et al. |
| 2003/0004536 A1 | 1/2003 | Boylan et al. |
| 2003/0004537 A1 | 1/2003 | Boyle et al. |
| 2003/0004539 A1 | 1/2003 | Linder et al. |
| 2003/0004540 A1 | 1/2003 | Linder et al. |
| 2003/0004541 A1 | 1/2003 | Linder et al. |
| 2003/0009188 A1 | 1/2003 | Linder et al. |
| 2003/0009189 A1 | 1/2003 | Gilson et al. |
| 2003/0015206 A1 | 1/2003 | Roth et al. |
| 2003/0018354 A1 | 1/2003 | Roth et al. |
| 2003/0023265 A1 | 1/2003 | Forber |
| 2003/0028238 A1 | 2/2003 | Burkett et al. |
| 2003/0032941 A1 | 2/2003 | Boyle et al. |
| 2003/0032977 A1 | 2/2003 | Brady et al. |
| 2003/0040772 A1 | 2/2003 | Hyodoh et al. |
| 2003/0042186 A1 | 3/2003 | Boyle |
| 2003/0045898 A1 | 3/2003 | Harrison et al. |
| 2003/0057156 A1 | 3/2003 | Peterson et al. |
| 2003/0060782 A1 | 3/2003 | Bose et al. |
| 2003/0060843 A1 | 3/2003 | Boucher |
| 2003/0060844 A1 | 3/2003 | Borillo et al. |
| 2003/0065354 A1 | 4/2003 | Boyle et al. |
| 2003/0069596 A1 | 4/2003 | Eskuri |
| 2003/0069597 A1 | 4/2003 | Petersen |
| 2003/0078519 A1 | 4/2003 | Salahieh et al. |
| 2003/0078614 A1 | 4/2003 | Salahieh et al. |
| 2003/0083692 A1 | 5/2003 | Vrba et al. |
| 2003/0083693 A1 | 5/2003 | Daniel et al. |
| 2003/0093106 A1 | 5/2003 | Brady et al. |
| 2003/0100917 A1 | 5/2003 | Boyle et al. |
| 2003/0100918 A1 | 5/2003 | Duane |
| 2003/0105484 A1 | 6/2003 | Boyle et al. |
| 2003/0109824 A1 | 6/2003 | Anderson et al. |
| 2003/0114879 A1 | 6/2003 | Euteneuer et al. |
| 2003/0114880 A1 | 6/2003 | Hansen et al. |
| 2003/0120303 A1 | 6/2003 | Boyle et al. |
| 2003/0125764 A1 | 7/2003 | Brady et al. |
| 2003/0130680 A1 | 7/2003 | Russell |
| 2003/0130681 A1 | 7/2003 | Ungs |
| 2003/0130682 A1 | 7/2003 | Broome et al. |
| 2003/0130684 A1 | 7/2003 | Brady et al. |
| 2003/0130685 A1 | 7/2003 | Daniel et al. |
| 2003/0130686 A1 | 7/2003 | Daniel et al. |
| 2003/0130687 A1 | 7/2003 | Daniel et al. |
| 2003/0130688 A1 | 7/2003 | Daniel et al. |
| 2003/0135162 A1 | 7/2003 | Deyette, Jr. et al. |
| 2003/0135232 A1 | 7/2003 | Douk et al. |
| 2003/0139764 A1 | 7/2003 | Levinson et al. |
| 2003/0144670 A1 | 7/2003 | Pavcnik et al. |
| 2003/0144685 A1 | 7/2003 | Boyle et al. |
| 2003/0144686 A1 | 7/2003 | Martinez et al. |
| 2003/0144687 A1 | 7/2003 | Brady et al. |
| 2003/0144688 A1 | 7/2003 | Brady et al. |
| 2003/0144689 A1 | 7/2003 | Brady et al. |
| 2003/0150821 A1 | 8/2003 | Bates et al. |
| 2003/0153942 A1 | 8/2003 | Wang et al. |
| 2003/0153943 A1 | 8/2003 | Michael et al. |
| 2003/0158574 A1 | 8/2003 | Esch et al. |
| 2003/0163064 A1 | 8/2003 | Vrba et al. |

| | | | |
|---|---|---|---|
| 2003/0171770 A1 | 9/2003 | Kusleika et al. | |
| 2003/0171771 A1 | 9/2003 | Anderson et al. | |
| 2003/0171803 A1 | 9/2003 | Shimon | |
| 2003/0176884 A1 | 9/2003 | Berrada et al. | |
| 2003/0176885 A1 | 9/2003 | Broome et al. | |
| 2003/0176886 A1 | 9/2003 | Wholey et al. | |
| 2003/0181942 A1 | 9/2003 | Sutton et al. | |
| 2003/0181943 A1 | 9/2003 | Daniel et al. | |
| 2003/0187474 A1 | 10/2003 | Keegan et al. | |
| 2003/0187475 A1 | 10/2003 | Tsugita et al. | |
| 2003/0187495 A1 | 10/2003 | Cully et al. | |
| 2003/0191493 A1 | 10/2003 | Epstein et al. | |
| 2003/0195555 A1 | 10/2003 | Khairkhahan et al. | |
| 2003/0199819 A1 | 10/2003 | Beck | |
| 2003/0204168 A1 | 10/2003 | Bosma et al. | |
| 2003/0208224 A1 | 11/2003 | Broome | |
| 2003/0208225 A1 | 11/2003 | Goll et al. | |
| 2003/0208226 A1 | 11/2003 | Bruckheimer et al. | |
| 2003/0208227 A1 | 11/2003 | Thomas | |
| 2003/0208228 A1 | 11/2003 | Gilson et al. | |
| 2003/0212361 A1 | 11/2003 | Boyle et al. | |
| 2003/0212429 A1 | 11/2003 | Keegan et al. | |
| 2003/0212431 A1 | 11/2003 | Brady et al. | |
| 2003/0212434 A1 | 11/2003 | Thielen | |
| 2003/0216774 A1 | 11/2003 | Larson | |
| 2003/0220665 A1 | 11/2003 | Eskuri et al. | |
| 2003/0225418 A1 | 12/2003 | Esksuri et al. | |
| 2003/0229295 A1 | 12/2003 | Houde et al. | |
| 2003/0229374 A1 | 12/2003 | Brady et al. | |
| 2003/0233117 A1 | 12/2003 | Adams et al. | |
| 2004/0010282 A1 | 1/2004 | Kusleika | |

FOREIGN PATENT DOCUMENTS

| | | | |
|---|---|---|---|
| EP | 0256683 | 2/1988 | |
| EP | 0461375 | 4/1991 | |
| EP | 0533511 | 3/1993 | |
| EP | 0596172 | 5/1994 | |
| EP | 0655228 | 5/1995 | |
| EP | 0743046 | 11/1996 | |
| EP | 0759287 | 2/1997 | |
| EP | 0791340 | 8/1997 | |
| EP | 0827756 | 3/1998 | |
| EP | 1123688 | 8/2001 | |
| EP | 1127556 | 8/2001 | |
| EP | 1149566 | 10/2001 | |
| EP | 1172073 | 1/2002 | |
| EP | 1181900 | 2/2002 | |
| FR | 2580504 | 10/1986 | |
| FR | 2616666 | 12/1988 | |
| FR | 2768326 | 3/1999 | |
| GB | 2020557 | 11/1979 | |
| GB | 2200848 | 8/1998 | |
| WO | WO 88/09683 | 12/1988 | |
| WO | WO 89/07422 | 8/1989 | |
| WO | WO 94/24946 | 11/1994 | |
| WO | WO 95/32454 | 12/1995 | |
| WO | WO 95/34339 | 12/1995 | |
| WO | WO 96/01591 | 1/1996 | |
| WO | WO 96/39998 | 12/1996 | |
| WO | WO 97/03810 | 2/1997 | |
| WO | WO 97/17021 | 5/1997 | |
| WO | WO 97/17100 | 5/1997 | |
| WO | WO 97/17914 | 5/1997 | |
| WO | WO 97/27808 | 8/1997 | |
| WO | WO 97/42879 | 11/1997 | |
| WO | WO 98/24377 | 6/1998 | |
| WO | WO 98/30265 | 7/1998 | |
| WO | WO 98/33443 | 8/1998 | |
| WO | WO 98/38920 | 9/1998 | |
| WO | WO 98/39053 | 9/1998 | |
| WO | WO 98/46297 | 10/1998 | |
| WO | WO 98/49952 | 11/1998 | |
| WO | WO 98/50103 | 11/1998 | |
| WO | WO 98/51237 | 11/1998 | |
| WO | WO 99/16382 | 4/1999 | |
| WO | WO 99/20335 | 4/1999 | |
| WO | WO 99/22673 | 5/1999 | |
| WO | WO 99/23976 | 5/1999 | |
| WO | WO 99/25252 | 5/1999 | |
| WO | WO 99/44510 | 9/1999 | |
| WO | WO 99/44542 | 9/1999 | |
| WO | WO 99/51167 | 10/1999 | |
| WO | WO 99/55236 | 11/1999 | |
| WO | WO 00/07521 | 2/2000 | |
| WO | WO 00/07656 | 2/2000 | |
| WO | WO 00/16705 | 3/2000 | |
| WO | WO 00/21604 | 4/2000 | |
| WO | WO 00/44428 | 8/2000 | |
| WO | WO 00/49970 | 8/2000 | |
| WO | WO 00/56390 | 9/2000 | |
| WO | WO 00/66031 | 11/2000 | |
| WO | WO 00/67664 | 11/2000 | |
| WO | WO 00/67665 | 11/2000 | |
| WO | WO 00/67666 | 11/2000 | |
| WO | WO 00/67667 | 11/2000 | |
| WO | WO 00/67668 | 11/2000 | |
| WO | WO 00/67669 | 11/2000 | |
| WO | WO 00/67670 | 11/2000 | |
| WO | WO 00/67671 | 11/2000 | |
| WO | WO 00/67829 | 11/2000 | |
| WO | WO 00/76390 | 12/2000 | |
| WO | WO 01/00084 | 1/2001 | |
| WO | WO 01/00087 | 1/2001 | |
| WO | WO 01/05329 | 1/2001 | |
| WO | WO 01/08595 | 2/2001 | |
| WO | WO 01/08596 | 2/2001 | |
| WO | WO 01/08742 | 2/2001 | |
| WO | WO 01/08743 | 2/2001 | |
| WO | WO 01/10343 | 2/2001 | |
| WO | WO 01/12082 | 2/2001 | |
| WO | WO 01/15629 | 3/2001 | |
| WO | WO 01/15630 | 3/2001 | |
| WO | WO 01/21077 | 3/2001 | |
| WO | WO 01/21100 | 3/2001 | |
| WO | WO 01/35857 | 5/2001 | |
| WO | WO 01/35858 | 5/2001 | |
| WO | WO 01/43662 | 6/2001 | |
| WO | WO 01/45590 | 6/2001 | |
| WO | WO 01/45591 | 6/2001 | |
| WO | WO 01/45592 | 6/2001 | |
| WO | WO 01/49208 | 7/2001 | |
| WO | WO 01/49209 | 7/2001 | |
| WO | WO 01/49215 | 7/2001 | |
| WO | WO 01/50982 | 7/2001 | |
| WO | WO 01/52768 | 7/2001 | |
| WO | WO 01/72205 | 10/2001 | |
| WO | WO 01/80776 | 11/2001 | |
| WO | WO 01/80777 | 11/2001 | |
| WO | WO 01/82830 | 11/2001 | |
| WO | WO 01/82831 | 11/2001 | |
| WO | WO 01/87183 | 11/2001 | |
| WO | WO 01/89413 | 11/2001 | |
| WO | WO 01/97714 | 12/2001 | |
| WO | WO 02/43595 | 6/2002 | |
| WO | WO 02/083225 | 10/2002 | |
| WO | WO 03/022325 | 3/2003 | |
| WO | WO 03/047648 | 6/2003 | |
| WO | WO 03/084434 | 10/2003 | |
| WO | WO 03/084435 | 10/2003 | |
| WO | WO 03/084436 | 10/2003 | |
| WO | WO 03/088805 | 10/2003 | |

WO    WO 03/088869    10/2003

OTHER PUBLICATIONS

Rolf W. Gunther et al., "Minibasket for Percutaneous Embolectomy and Filter Protection Against Distal Embolization: Technical Note", Cardiovasular and Interventional Radiology, Springer—Verlag New York Inc. 1991.

US 6,348,062, 02/2002, Hopkins et al. (withdrawn)

* cited by examiner

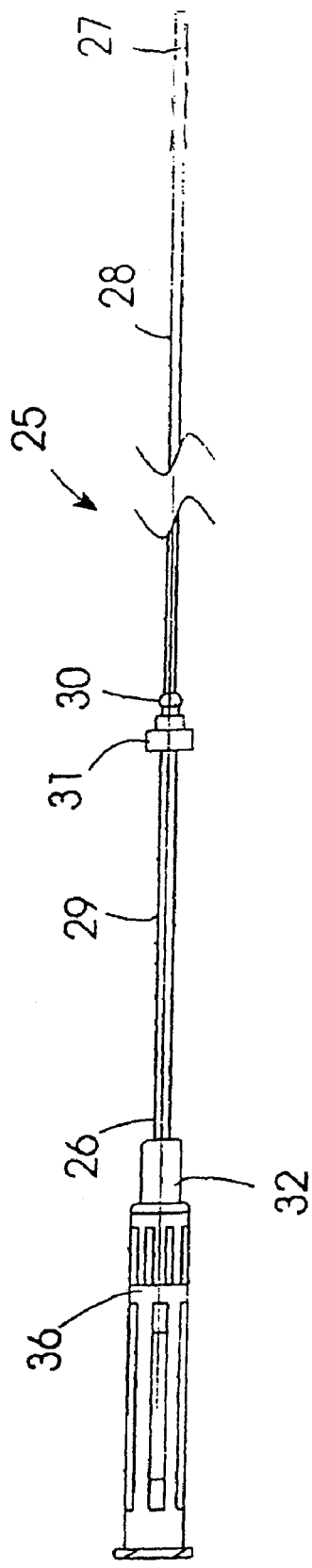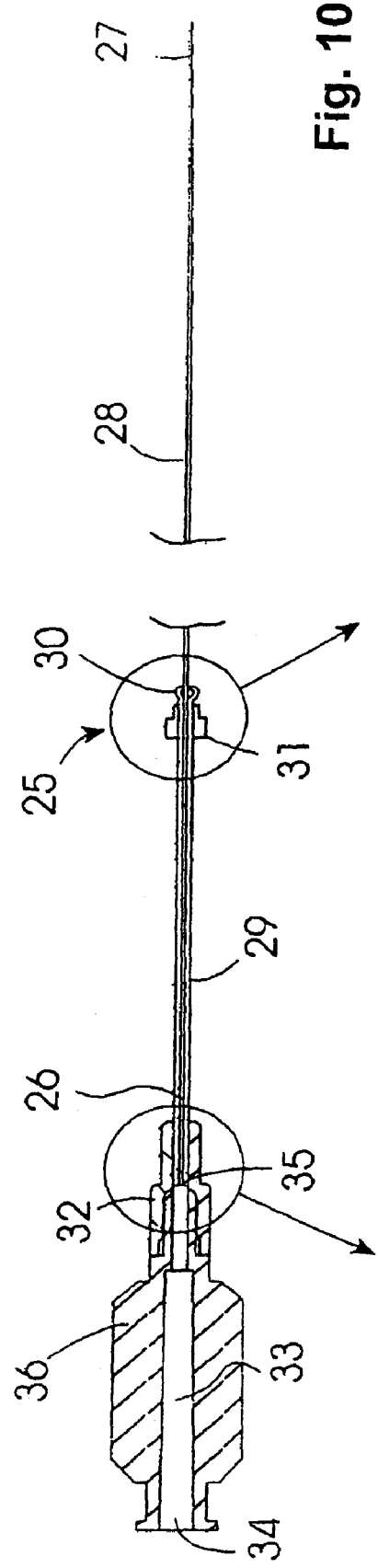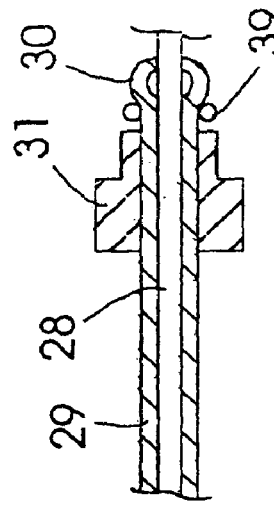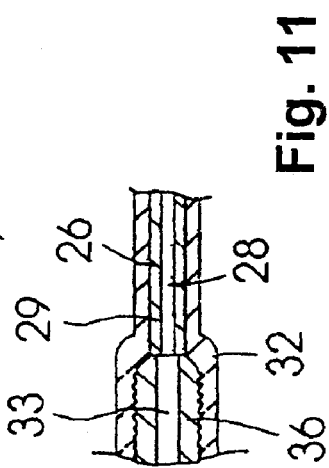

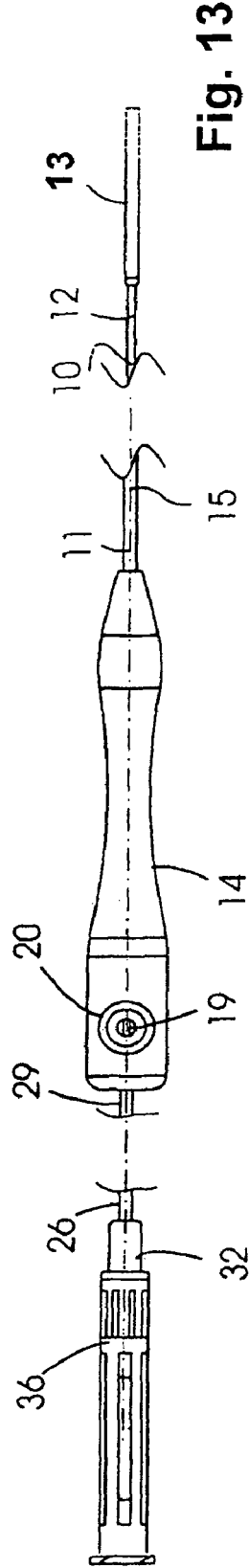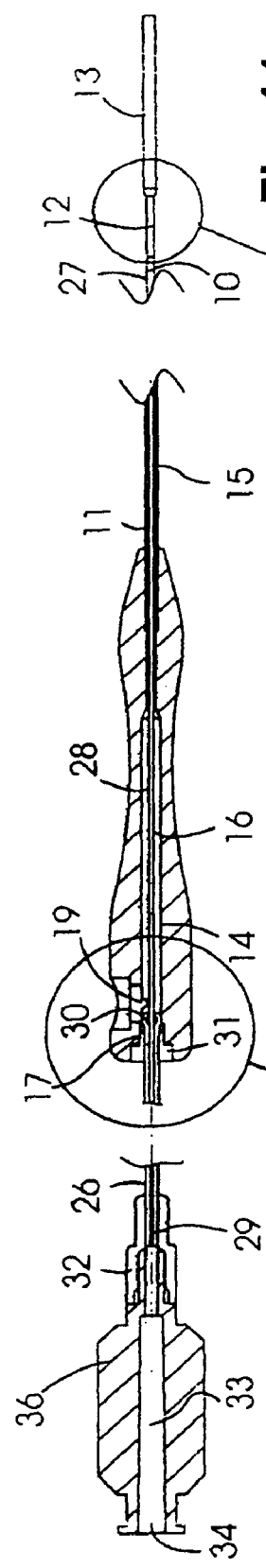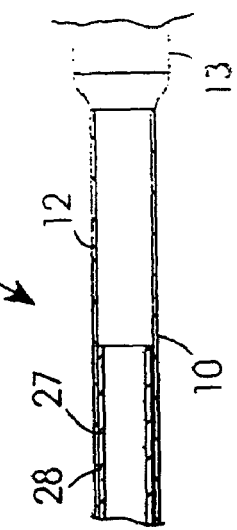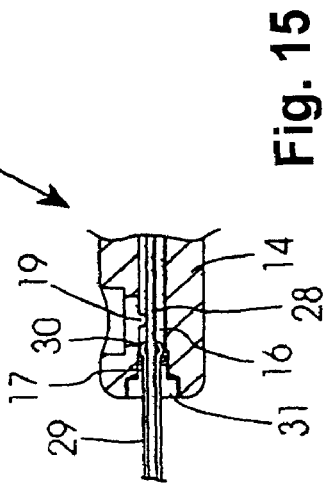

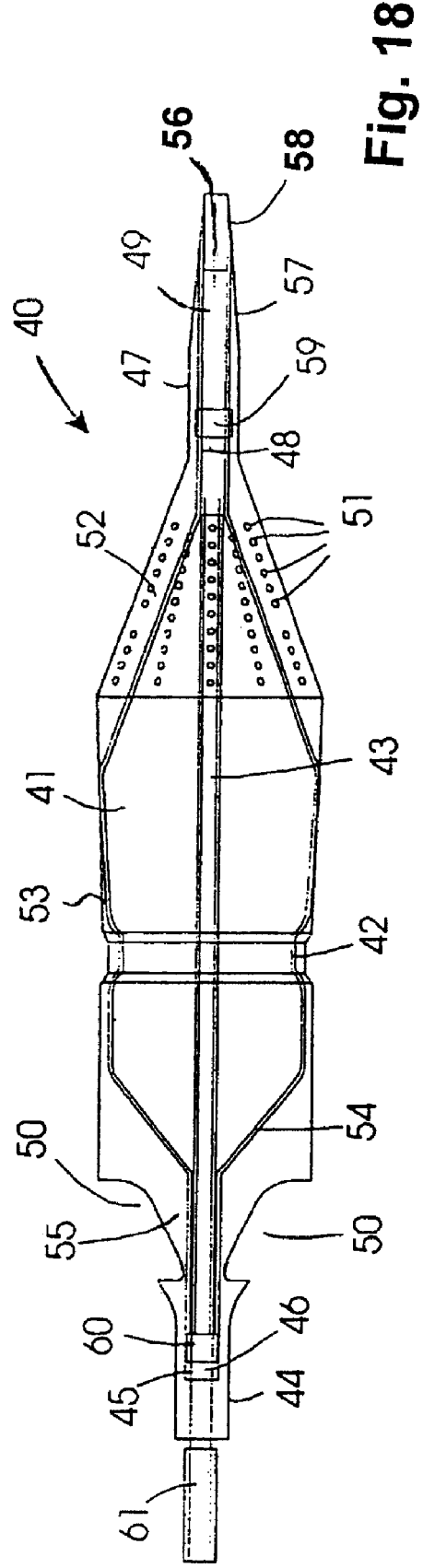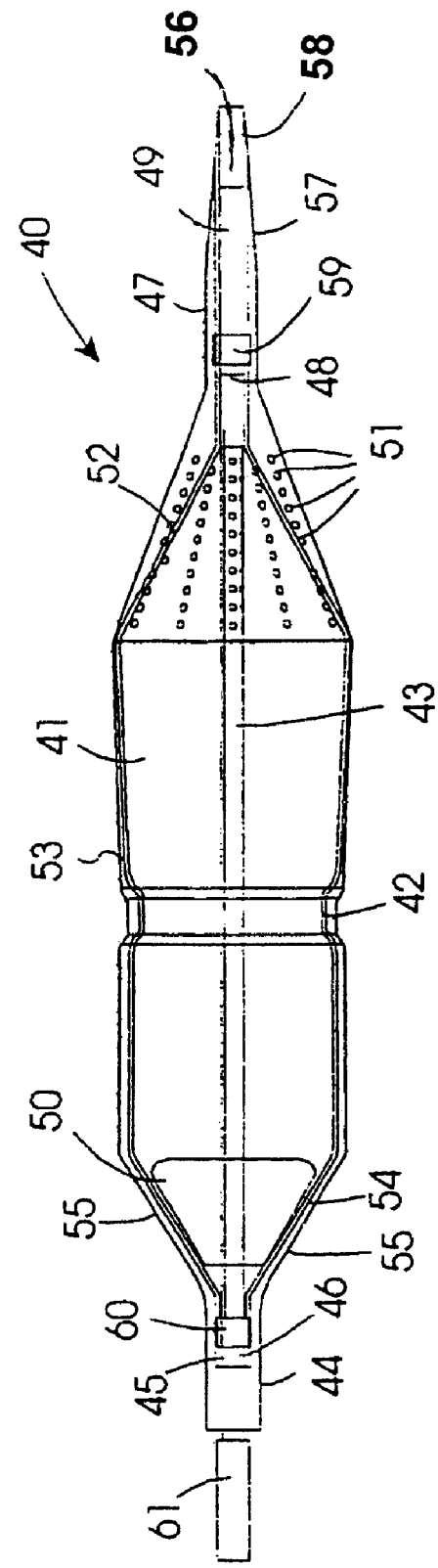

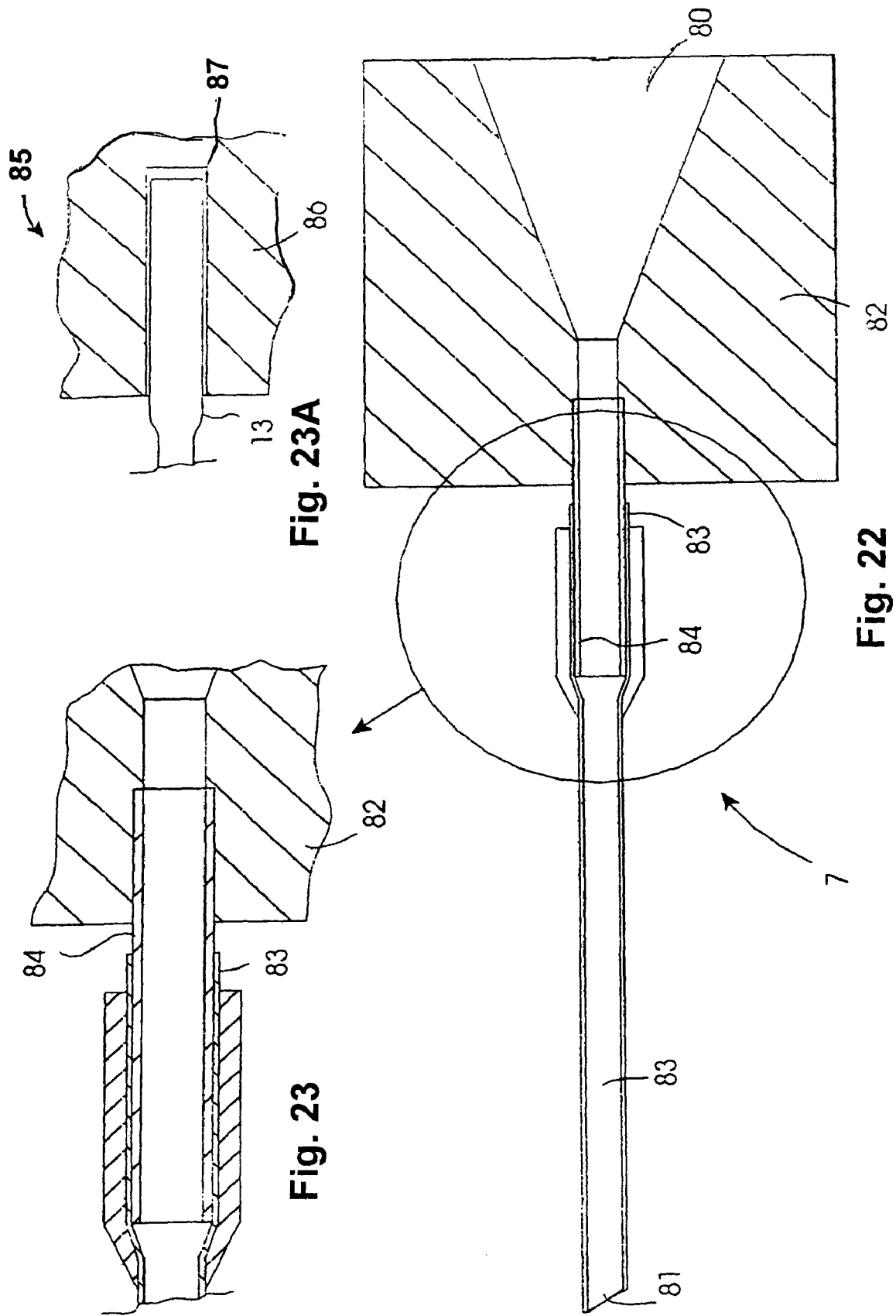

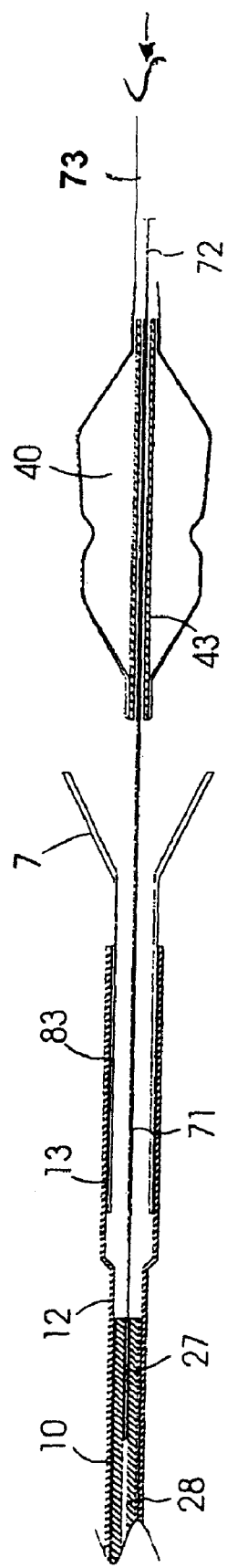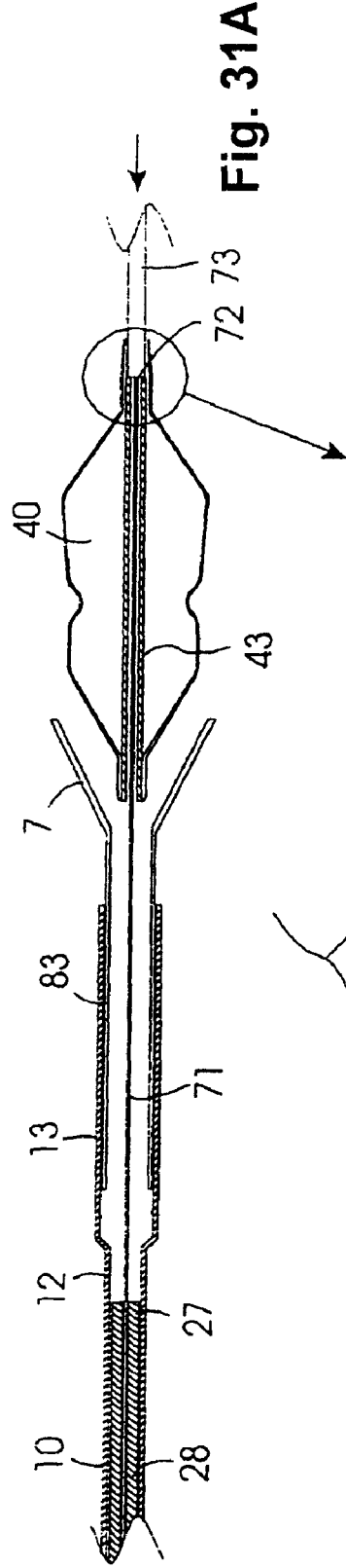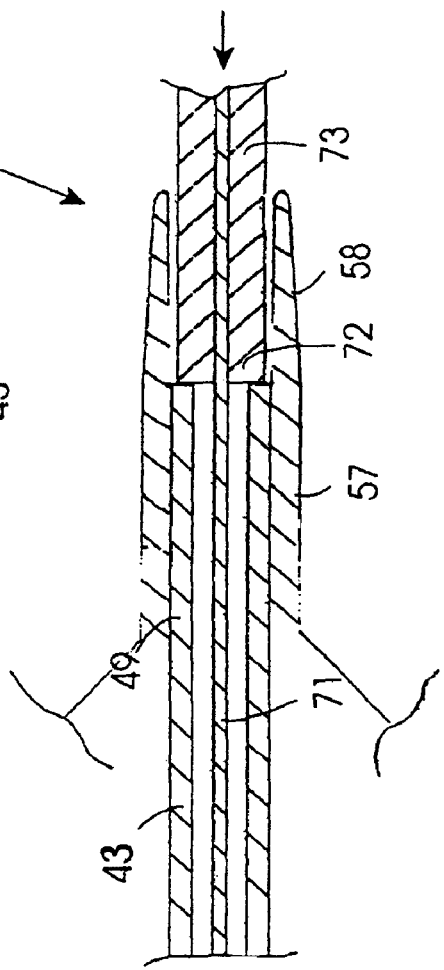

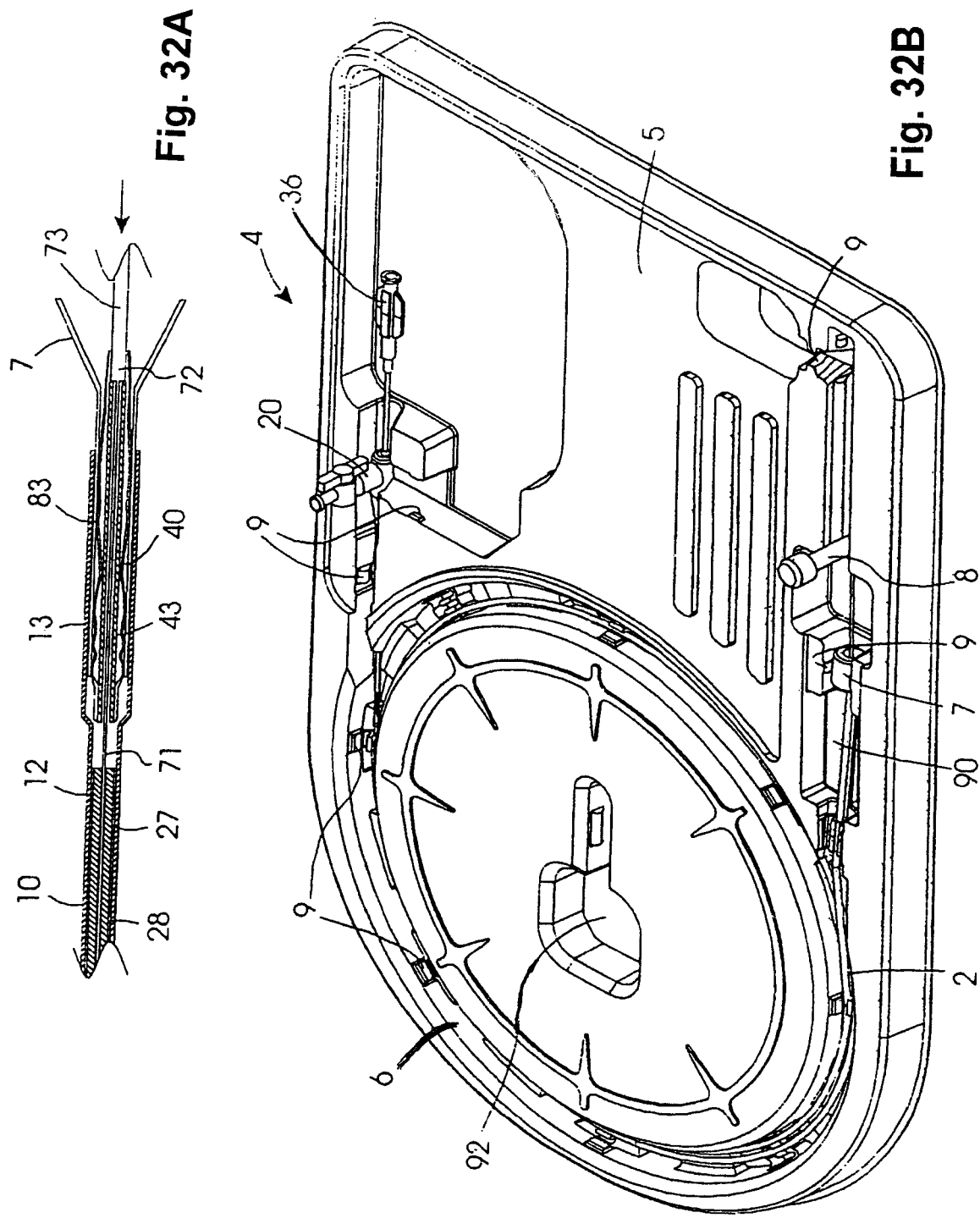

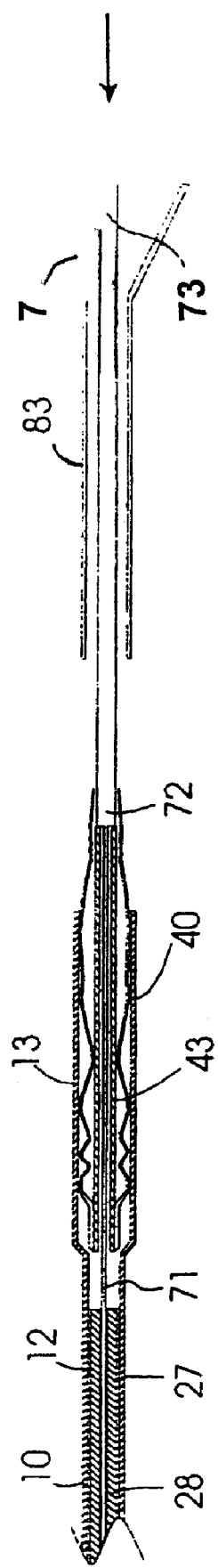
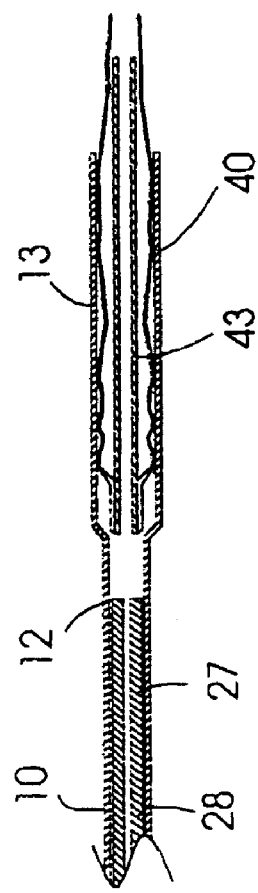
Fig. 33
Fig. 34

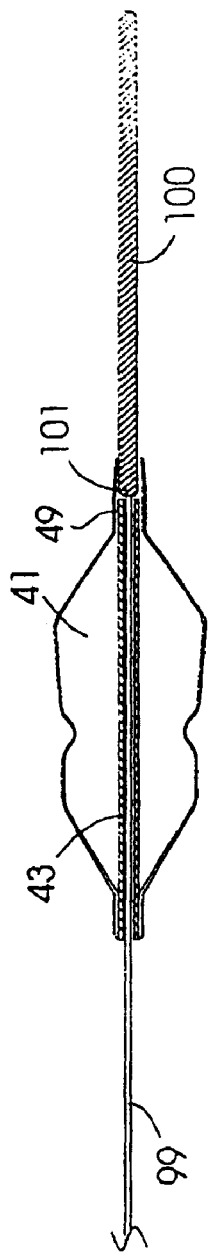
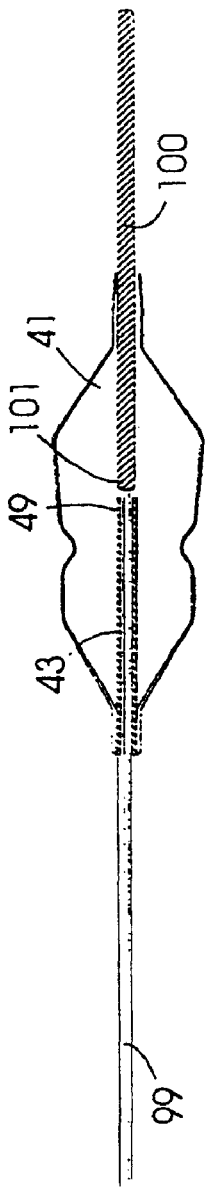
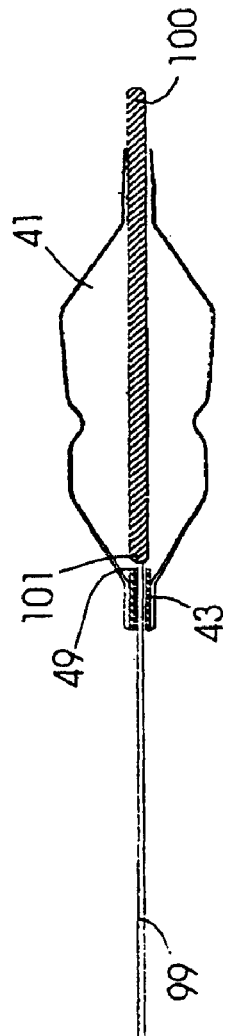
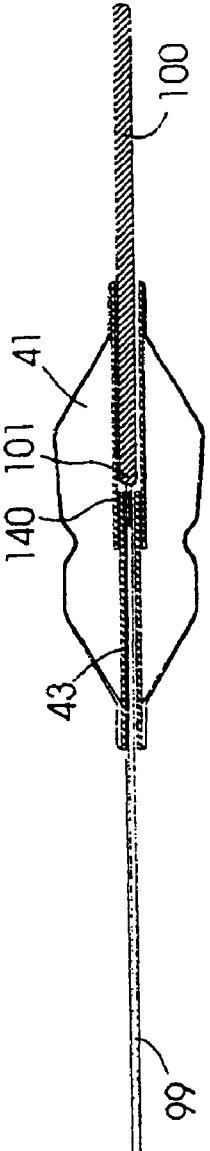
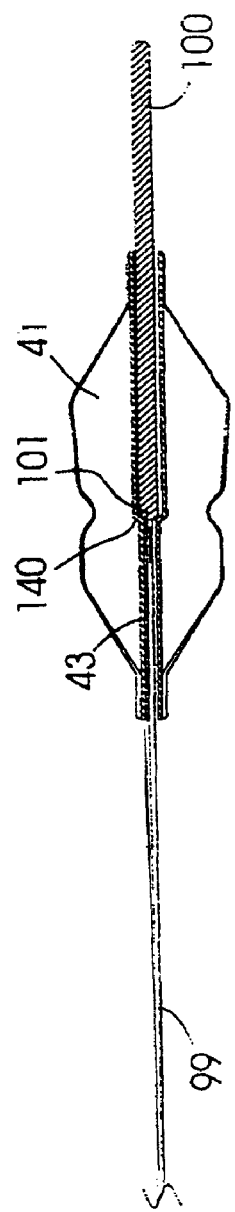

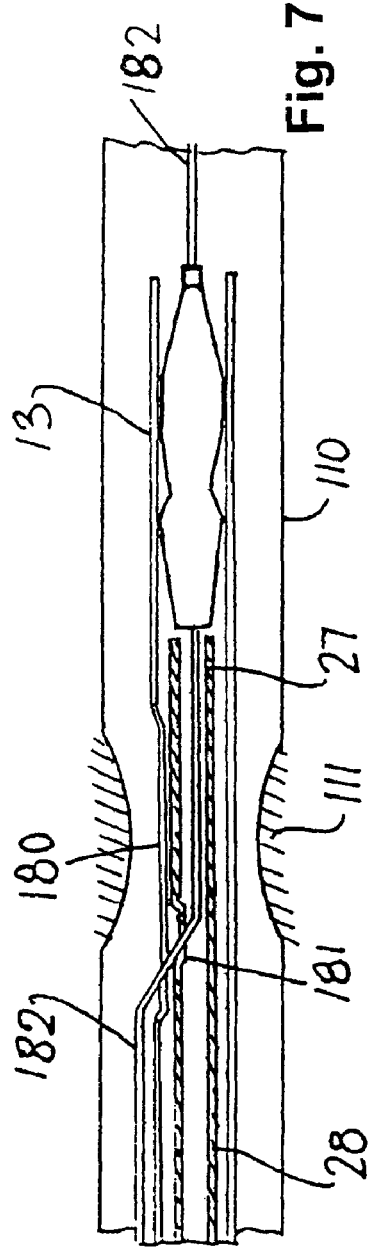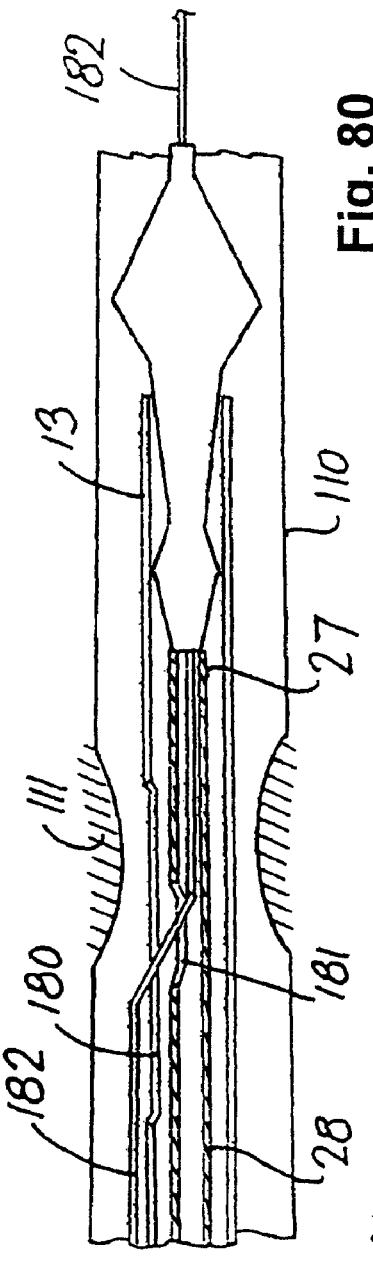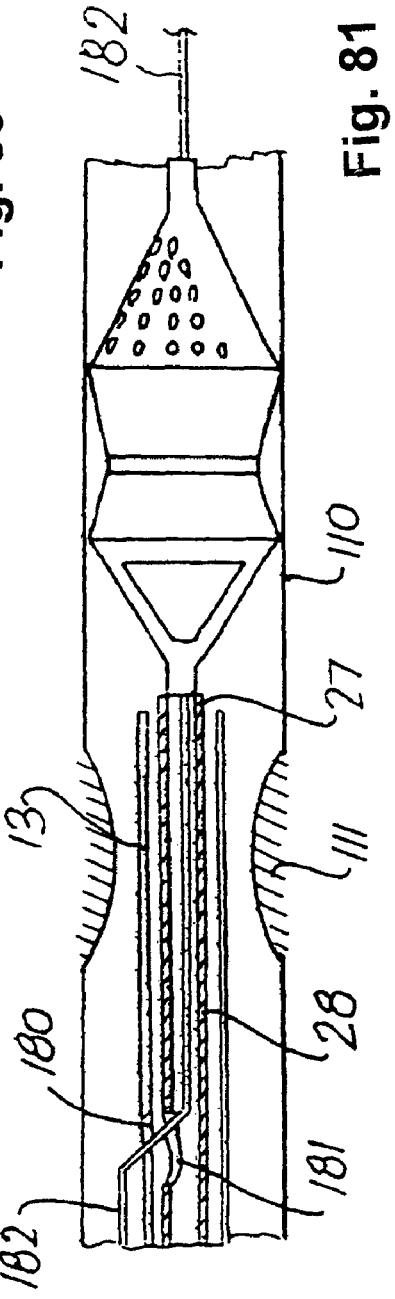

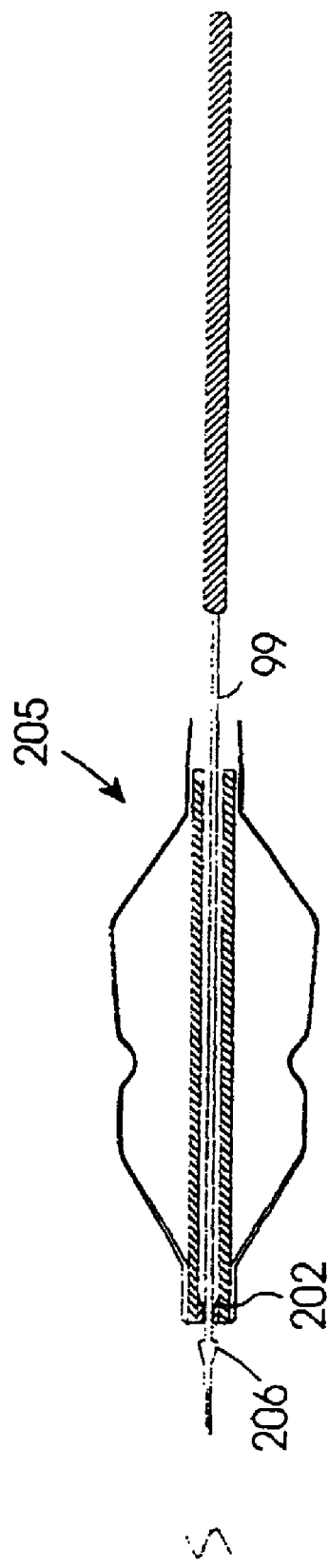
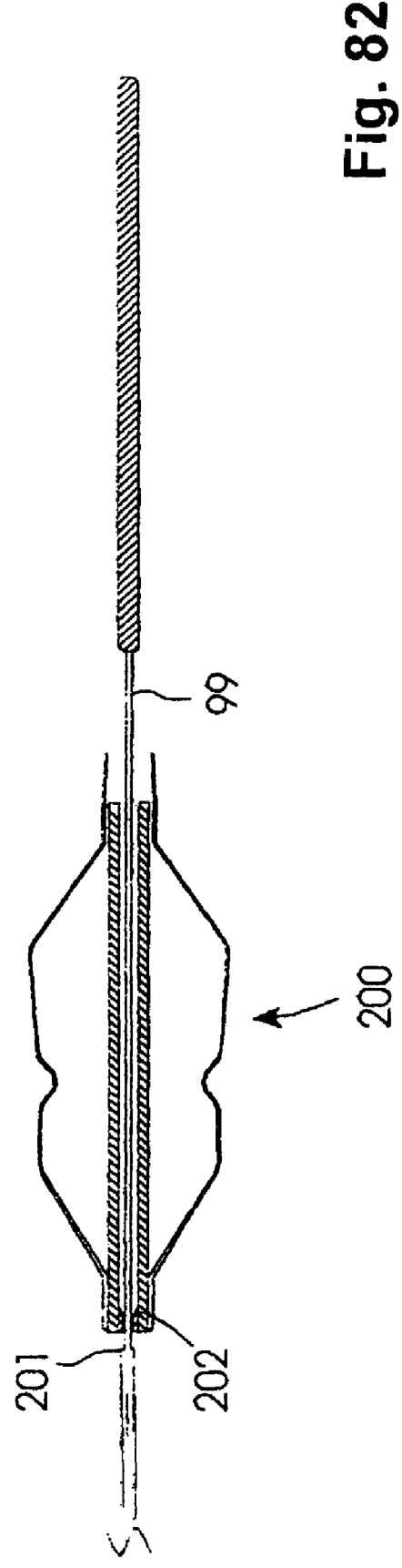
Fig. 83
Fig. 82

EMBOLIC PROTECTION SYSTEM

This application is a continuation of U.S. application Ser. No. 10/939,995 filed Sep. 14, 2004, which is a continuation of U.S. application Ser. No. 09/838,544 filed Apr. 20, 2001, now U.S. Pat. No. 6,887,256, which is a continuation-in-part of U.S. application Ser. No. 09/188,472 filed Nov. 9, 1998, now U.S. Pat. No. 6,336,934, which claim benefit to Irish Patent Application No. 970789 filed on Nov. 7, 1997, Irish Patent Application No. 980267 filed on Apr. 8, 1998, International Application No. PCT/IE00/00045 filed on Apr. 20, 2000; Irish Patent Application No. 2001/0258 filed on Mar. 16, 2001; Irish Patent Application No 2001/0260 filed on Mar. 16, 2001; and Irish Patent Application No. 2001/0261 filed on Mar. 16, 2001; all of the disclosures of which are hereby incorporated by reference in their entirety.

BACKGROUND OF THE INVENTION

Summary of the Invention

This invention relates to a transvascular embolic protection system for safely capturing and retaining embolic material released during an interventional procedure while maintaining blood flow.

WO-A-99/23976 describes various embolic protection systems of this type. WO-A-99/51167 and WO-A-99/51166 describe delivery catheters for delivery of an embolic protection filter to a desired site in the vascular system. Various embolic filters are described in WO-A-00/67668, WO-A-00/67669 WO-A-00/67670 and WO-A00/67671. A retrieval catheter for use with such embolic protection systems is described in WO-A-01/12082.

There is an economical and clinical need to provide an improved embolic protection system which will be easy and convenient for a clinician to prepare for use, to deploy and to retrieve. In addition there is a need to provide such a system which will facilitate a wide range of clinical procedures to be carried out.

STATEMENTS OF INVENTION

According to the invention there is provided an embolic protection system comprising:
- a guidewire for advancing through a vasculature, the guidewire having a distal end and a proximal end;
- an embolic protection filter having a filter body with a distal end and a proximal end, the filter body providing for a collapsed configuration and an expanded deployed configuration;
- the embolic protection filter body having a guidewire path for slidably receiving the guidewire to permit movement of the filter relative to the guidewire when the filter is in the collapsed configuration and the expanded deployed configuration;
- a delivery catheter advanceable over the guidewire for delivery of the embolic protection filter; the delivery catheter having a proximal end and a distal end, the filter being deployed from the distal end of the delivery catheter into the expanded deployed configuration;
- a retrieval catheter advanceable over the guidewire for retrieval of the filter, the retrieval catheter having a distal end and a proximal end; and
- engagement elements for engaging the embolic protection filter with the guidewire for retrieval of the filter into the retrieval catheter in the collapsed configuration.

In one embodiment of the invention the guidewire path is in isolation from the embolic material captured within the filter body.

In a preferred case the tubular guidewire path is defined by a tubular sleeve. Ideally the tubular sleeve extends from the proximal end to the distal end of the filter. Desirably the guidewire path is a tubular guidewire path.

In another embodiment the engagement elements comprise a guidewire engagement element on the guidewire and a filter engagement element on the filter, the engagement elements co-operating to provide selective engagement and positioning of the filter with respect to the guidewire. Preferably the engagement element of the guidewire comprises a guidewire abutment on the guidewire.

The guidewire abutment may be located at the distal end of the guidewire.

The guidewire abutment may be located proximal of the distal and of the guidewire.

In a particularly preferred embodiment the engagement element of the filter comprises a filter abutment on the filter.

The filter abutment may be a distal abutment on the filter.

The filter abutment may be a proximal abutment on the filter.

Most preferably the tubular guidewire path is defined by a sleeve and the filter abutment is provided by the sleeve.

In another embodiment of the invention the engagement elements comprise releasable locking elements. Preferably the releasable locking elements comprise a taper lock. Ideally the guidewire engagement element comprises a locking ring on the guidewire and the filter engagement element comprises a tapered surface of the filter, the locking ring having a tapered surface which is engageable with the tapered surface of the filter to lock the filter to the guidewire. Most preferably the locking ring is a split ring.

In another case the embolic protection system includes a tube advanceable over the guidewire, the locking ring being located between a distal end of the tube and the filter for retrieval of the filter.

Desirably the releasable locking means includes a tether engageable with the filter for retrieving the filter into the retrieval catheter.

In a preferred embodiment the embolic protection system comprises deployment means for moving the collapsed filter relative to the distal end of the delivery catheter. Preferably the deployment means comprises a tube which is advanceable over the guidewire for engagement with the proximal end of the filter, the tube being movable longitudinally relative to the delivery catheter for deployment of the filter from the distal end of the delivery catheter.

In another embodiment the embolic protection system includes loading means for loading the filter into the delivery catheter. Ideally the loading means comprises a funnel having a narrowed portion disposed at the distal end of the delivery catheter and an enlarged portion for receiving a proximal portion of the filter in the expanded configuration, the filter being progressively collapsed as it is moved through the funnel for loading into the delivery catheter.

In a further embodiment the embolic protection system includes engagement means for engaging the filter within the retrieval catheter. Preferably the engagement means comprises a frictional engagement between the filter body and an internal surface of the distal end of the retrieval catheter. Most preferably the engagement means comprises projections on the inner surface of the retrieval catheter adjacent the distal end thereof.

In another preferred embodiment the delivery catheter includes an elongate slot disposed in a first sidewall thereof at a first distal location which is spaced a relatively longer distance from the proximal end of the delivery catheter than from the distal end of the delivery catheter, and wherein the inner deployment catheter includes an aperture disposed in a second sidewall thereof at a second distal location which substantially corresponds with said first distal location for said elongate slot, thereby permitting cooperative movement of said filter with respect to said guidewire and associated delivery and deployment catheters for selective deployment of the filter while facilitating the rapid exchange of said catheter and filer assembly over a guidewire without the utilization of exchange wires or extension wires.

The embolic protection filter may comprise a collapsible filter body, the proximal inlet end of the filter body having one or more inlet openings sized to allow blood and embolic material enter the filter body, the distal outlet end of the filter body having a plurality of outlet openings sized to allow through passage of blood but to retain undesired embolic material within the filter body. Ideally the filter comprises a collapsible filter support frame having a proximal end and a distal end, the filter support frame being movable between a collapsed position for movement during delivery through the vascular system and an extended outwardly projecting position to support the filter body in an expanded position thereby urging the filter body into apposition with the vasculature upon deployment. Most preferably the embolic protection system comprises a guide olive provided at the distal end of the filter body.

Desirably the embolic protection system comprises an inner elongate sleeve to which the filter body and the filter support frame are mounted, the sleeve having a proximal end and a distal end, the guide olive extending distally of the sleeve distal end.

The proximal end of the filter support frame and the inlet end of the filter body are preferably attached to the proximal end of the sleeve.

The guide olive may be integral with the filter body.

Ideally the guide olive tapers distally inwardly.

In another aspect the invention provides a method for the capture and removal of embolic material from a blood vessel during an interventional procedure comprising the steps of:
  advancing a guidewire through a vasculature;
  crossing a desired treatment location with the guidewire;
  introducing over the guidewire a collapsible embolic protection filter having a collapsed configuration, the collapsed configuration permitting delivery and withdrawal of the filter;
  deploying the filter distal to the treatment location;
  carrying out the interventional procedure, embolic material generated during the treatment procedure being captured by the deployed filter;
  advancing a retrieval catheter over the guidewire;
  collapsing the filter into the retrieval catheter and with it the captured embolic material;
  withdrawing the retrieval catheter and the collapsed filter from the vasculature leaving the guidewire in the vasculature.

In one embodiment of the invention the method comprises the step of providing a catheter over the guidewire after withdrawal of the retrieval catheter.

In another embodiment the method includes the step of moving the guidewire after withdrawal of the retrieval catheter and the collapsed filter from the vasculature to re-position the guidewire in the vasculature.

The catheter may be a catheter for delivery of a diagnostic medium.

The catheter may be a catheter for delivery of a lytic agent.

The filter is preferably slidably disposed on the guidewire when the filter is in the expanded deployed configuration.

In one preferred case the filter is rotatably disposed on the guidewire when the filter is in the expanded deployed configuration.

In a further embodiment the method includes the steps of:
  loading the filter in a collapsed configuration within a delivery catheter;
  advancing the delivery catheter and filter over the guidewire to deliver the filter to a desired location; and
  deploying the filter from the delivery catheter at the desired location.

Preferably the method includes the steps of:
  collapsing the filter from an expanded configuration for loading the filter into the delivery catheter;
  the filter being expanded to a deployment configuration on release from the delivery catheter.

The treatment location may be a region of stenosis.

In one embodiment the interventional procedure includes a balloon dilation of the stenosis while the filter is deployed.

In another embodiment the interventional procedure includes a stenting of the treatment location while the filter is deployed.

According to another aspect of the invention there is provided a medical catheter for transvascular delivery and deployment of an embolic protection filter, the catheter comprising:
  an outer catheter tube defining a distal end; and
  an inner catheter tube defining a distal end;
  the outer tube being at least partially movable relative to the inner tube between a delivery configuration in which the distal end of the outer tube extends distally of the distal end of the inner tube to define a reception space for an embolic protection filter within the outer tube, and a deployment configuration in which the distal end of the inner tube extends distally of the distal end of the outer tube for deployment of the embolic protection filter;
  the inner catheter tube providing compressive resistance and the outer catheter tube providing stretch resistance.

In one embodiment the inner catheter tube at least partially comprises a relatively stiff core encased in a more pliable body.

In another embodiment the outer catheter tube at least partially comprises a relatively stiff core encased in a more pliable body.

The core is preferably oriented to prevent elongation of the outer catheter tube and/or compression of the inner catheter tube.

The core may comprise a mesh.

In one case the core comprises a plurality of longitudinally oriented strips of a stiff material. In another case the core comprises a plurality of circumferentially oriented strips of a stiff material.

The core may be of a metallic material. The metal is preferably stainless steel.

The pliable body may be of a plastics material. The plastic is preferably polyamide.

In a further aspect the invention provides an embolic protection device comprising:
  a collapsible filter element for delivery through a vascular system of a patient;
  the filter element comprising a collapsible filter body and a collapsible filter support frame contacting the filter body;
  the filter body having an inlet end and an outlet end, the inlet end of the filter body having one or more inlet openings sized to allow blood and embolic material enter the filter body, the outlet end of the filter body having a plurality of outlet openings sized to allow through passage of blood but to retain undesired embolic material within the filter body;

the filter support frame being movable between a collapsed position for movement through the vascular system and an extended outwardly projecting position to support the filter body in an expanded position;

the frame having an intermediate section to urge the filter body in the expanded position into apposition with a vessel wall, and a proximal section extending radially inwardly of the intermediate section;

at least part of the proximal section of the frame being spaced distally to accommodate inflow of embolic material through the inlet openings in the expanded position.

In one embodiment of the invention the filter body comprises one or more linking webs between adjacent inlet openings, and a part off the proximal section of the frame extends radially inwardly in alignment with the webs.

The frame proximal section preferably comprises one or more frame elements, at least one frame element providing the part of the proximal section spaced distally. Ideally at least one frame element provides the part of the proximal section extending radially inwardly in alignment with a linking web between adjacent inlet openings. Most preferably the number of frame elements is four, two frame elements extending radially inwardly in alignment with two webs between two inlet openings, and two frame elements spaced distally of the inlet openings.

Desirably the support frame is gold-plated and electropolished.

According to the invention there is also provided an assembly for loading a collapsible embolic protection filter into a catheter, the assembly comprising:— a catheter defining a reception space at a distal end of the catheter for receiving a collapsed embolic protection filter;

a separate removable pushing device for delivering the medical device into the reception space.

In one embodiment the assembly comprises a separate loading device to collapse the embolic protection filter, the loading device defining an inlet end and an outlet end, the outlet end being configured for co-operative alignment with the reception space.

The pushing device may comprises a proximal stop for engagement with the embolic protection filter. Preferably the pushing device comprises a stem, the stem having a distal stop for engaging the embolic protection filter. Ideally the pushing device comprises a handle.

In another embodiment the loading device comprises means for radially compressing the embolic protection filter.

The loading device preferably comprises a funnel, the inlet end defining a larger cross sectional area than the outlet end. Ideally the loading device comprises a main support having a funnel-shaped bore formed from a frusto-conical embolic protection filter receiving portion terminating in a cylindrical portion formed by a loading tube projecting from the main support for alignment with the reception space before loading.

The cone angle of the funnel is preferably between 15° and 65°. Most preferably the cone angle is between 35° and 45°.

In a preferred embodiment of the invention the loading device extends into the reception space.

In another preferred embodiment of the invention the loading device extends around the outside of the reception space.

In a further embodiment the assembly comprises a tray, the tray comprising a first retaining means for releasably supporting the pushing device in a disengaged position before delivering the embolic protection filter into the catheter. Preferably the assembly comprises a second retaining means for releasably supporting the loading device in co-operative alignment with the catheter during loading.

The retaining means may comprises a channel for receiving the loading device and/or the catheter and/or the pushing device, and at least one projection on the channel wall projecting inwardly for snap retention of the loading device and/or the catheter and/or the pushing device.

Ideally the tray comprises a liquid retaining bath formed by a recess in the tray, the bath having a depth sufficient to accommodate in a totally submerged state the reception space of the catheter and the embolic protection device for submerged loading of the embolic protection filter into the reception space.

The tray preferably has a catheter holding channel communicating with the bath, the channel defining a pathway around the tray which supports the catheter in a loading position on the tray.

In another embodiment means for securing the catheter within the channel comprises a number of retainers spaced-apart along the channel, each retainer comprising two or more associated projections which project inwardly from opposite side walls of the channel adjacent a mouth of the channel, the projections being resiliently deformable for snap engagement of the catheter within the channel behind the projections.

A ramp may be provided at an end of the channel communicating with the bath to direct the reception space of the catheter towards a bottom of the bath.

Ideally means is provided within the bath for supporting the reception space of the catheter above the bottom of the bath.

Said supporting means is preferably a step adjacent the channel.

The first retaining means may be provided within the bath.

Desirably the assembly comprises a flushing means. Most preferably the flushing means comprises a syringe.

In a further aspect of the invention there is, provided a method of loading an embolic protection filter into a catheter, the method comprising the steps of:

providing an embolic protection filter, the embolic protection device being collapsible;

providing a embolic protection catheter defining a reception space at a distal end of the catheter for receiving the collapsed embolic protection filter;

providing a pushing device for delivering the embolic protection filter into the reception space;

delivering the embolic protection filter into the reception space using the pushing device; and removing the pushing device from the reception space.

In one embodiment the method comprises the steps of providing a loading device to collapse the embolic protection filter, the loading device defining an inlet end and an outlet end;

aligning the outlet end of the loading device in co-operation with the reception space; and delivering the embolic protection filter through the inlet end of the loading device and into the reception space.

In a preferred case the catheter comprises an internal proximal stop, and the method comprises the step of moving the collapsed embolic protection filter proximally in the reception space using the pushing device to engage the internal proximal stop and disassociate the loaded catheter from the loading device before removing the pushing device.

The catheter may be constrained relative to the loading device before delivery of the embolic protection filter through the loading device into the reception space, and the method comprises the step of releasing the constraint to facilitate disassociation of the loaded catheter from the loading device.

In another embodiment the pushing device comprises a wire for threading through the embolic protection filter, the wire defining a distal stop for engaging the embolic protection filter.

The loading device may comprise an elongate neck at the outlet end, and the method comprises the step of at least partially positioning the elongate neck in the reception space before delivering the embolic protection filter into the reception space.

In a preferred embodiment the method comprises the step of flushing the embolic protection filter before delivering the embolic protection filter into the reception space.

Ideally the method comprises the step of flushing the catheter before delivering the embolic protection filter into the reception space.

In a preferred case the catheter comprises an outer catheter tube and an inner catheter tube, the inner catheter tube defining the internal proximal stop.

Desirably both the inner catheter tube and the outer catheter tube are flushed before delivering the embolic protection filter through the loading device.

In another aspect the invention provides a method of loading an embolic protection filter into a catheter, the method comprising the steps of:
  providing a embolic protection filter, the embolic protection filter being collapsible;
  providing a catheter defining a reception space at a distal end of the catheter for receiving the collapsed embolic protection filter, the catheter comprising at least one internal proximal stop;
  providing a loading device to collapse the embolic protection filter, the loading device defining an inlet end and an outlet end;
  aligning the outlet end of the loading device with the reception space;
  delivering the embolic protection filter through the loading device and into the reception space; and
  moving the collapsed embolic protection filter towards its proximal end in the reception space to engage said at least one the internal proximal stop and disassociate the loaded catheter from the loading device.

In one embodiment the method comprises the steps of:
  providing a pushing device for delivering the embolic protection filter through the loading device and into the reception space, and for engaging the collapsed embolic protection filter with the internal proximal stop; and
  removing the pushing device after disassociating the loaded catheter from the loading device.

In a preferred embodiment the pushing device comprises a wire for threading through the embolic protection filter, the wire defining a distal stop for engaging the embolic protection filter.

The loading device preferably comprises an elongate neck at the outlet end, and the method preferably comprises the step of at least partially aligning the elongate neck with the reception space before delivering the embolic protection filter through the loading device.

The method may comprise the step of flushing the embolic protection filter before delivering the embolic protection filter through the loading device.

The method may comprise the step of flushing the catheter before delivering the embolic protection filter into the reception space.

In a preferred embodiment the catheter comprises an outer catheter tube and an inner catheter tube, the inner catheter tube defining the internal proximal stop.

Desirably both the inner catheter tube and the outer catheter tube are flushed before delivering the embolic protection filter through the loading device.

According to a further aspect of the invention there is provided a, removable device for loading a collapsible embolic protection filter into a catheter, the device comprising a distal stop for releasably engaging with the embolic protection filter to push the embolic protection filter towards a proximal end of a catheter thereby loading the embolic protection filter into the catheter.

The distal stop is preferably provided on an elongate stem.

Most preferably the distal stop is integral with the stem.

In one case the distal stop comprises a step in the stem from a small diameter portion proximal of the step to a large diameter portion distal of the step.

The small diameter portion preferably has a diameter of approximately 0.014" (0.3556 mm).

The large diameter portion preferably has a diameter of approximately 0.018" (0.4572 mm).

The distal stop may be attached to the stem.

Ideally the stem comprises a wire.

The stem may comprise a low friction coating for ease of threading through the medical device. Ideally the coating is of polytetrafluoroethylene.

In one case the device comprises a handle.

The invention provides a clinician with the freedom to select from different guidewires prior to selection of an embolic filter.

Prior art assemblies suffer from the disadvantage that different guidewires cannot be used with a particular filter during an interventional procedure. A clinician is thus constrained to discard both the guidewire and the filter if the guidewire proves unsuitable, for example because it is too stiff or some other mechanical property is undesirable.

An important advantage of the invention is that because the filter is not attached to the guidewire in a collapsed configuration for delivery, the guidewire which is first advanced through the vasculature has a lower-profile. Therefore the guidewire alone can more easily navigate narrow and tortuous regions of the vasculature.

Another important advantage of the invention is that because the filter is not fixed to the guidewire, if the deployed filter is mis-sized with respect to the region of the treatment site it is free to be carried distally by blood flow to a narrow section of the vasculature at which the filter effectively achieves apposition with the vessel wall. This ensures that all blood flow with entrained embolic material passes through the filter.

BRIEF DESCRIPTION OF THE DRAWINGS

The invention will be more clearly understood from the following description of some embodiments thereof, given by way of example only, with reference to the accompanying drawings, in which:

FIG. 9 is a plan view of an inner catheter of the embolic protection system;

FIG. 10 is a side, partially cross-sectional view of the inner catheter of FIG. 9;

FIG. 11 is an enlarged view of part of the inner catheter of FIG. 10;

FIG. 12 is an enlarged view of another part of the inner catheter of FIG. 10;

FIG. 13 is a plan view of the inner catheter and the delivery catheter assembled;

FIG. 14 is a side, partially cross-sectional view of the catheter assembly of FIG. 13;

FIG. 15 is an enlarged view of part of the catheter assembly of FIG. 14;

FIG. 16 is an enlarged view of another part of the catheter assembly of FIG. 14;

FIG. 18 is a side, partially cross-sectional view of an embolic protection device of the embolic protection system;

FIG. 19 is a plan view of the embolic protection device of FIG. 18;

FIG. 22 is a side, partially cross-sectional view of a loading device of the embolic protection system;

FIG. 23 is an enlarged view of the detail of the loading device of FIG. 22;

FIG. 23A is a cross-sectional view of an alternative loading device;

FIGS. 30 to 32B are schematic views illustrating loading of the embolic protection device of FIGS: 18 and 19 into the catheter assembly of FIGS. 13 to 17;

FIGS. 33 and 34 are schematic views illustrating disassociation of the loaded catheter assembly of FIG. 32A from the loading device of FIGS. 22 and 23;

FIGS. 48 to 56 are side, partially cross-sectional views of other embolic protection devices of the embolic protection system;

FIGS. 78 to 81 are schematic views illustrating delivery and deployment of an embolic protection device of a rapid exchange embolic protection system in a vasculature;

FIG. 82 is a side, partially cross-sectional view of another embolic protection system;

FIG. 83 is a side, partially cross-sectional view of a further embolic protection device.

DETAILED DESCRIPTION OF THE INVENTION

Figure 1:
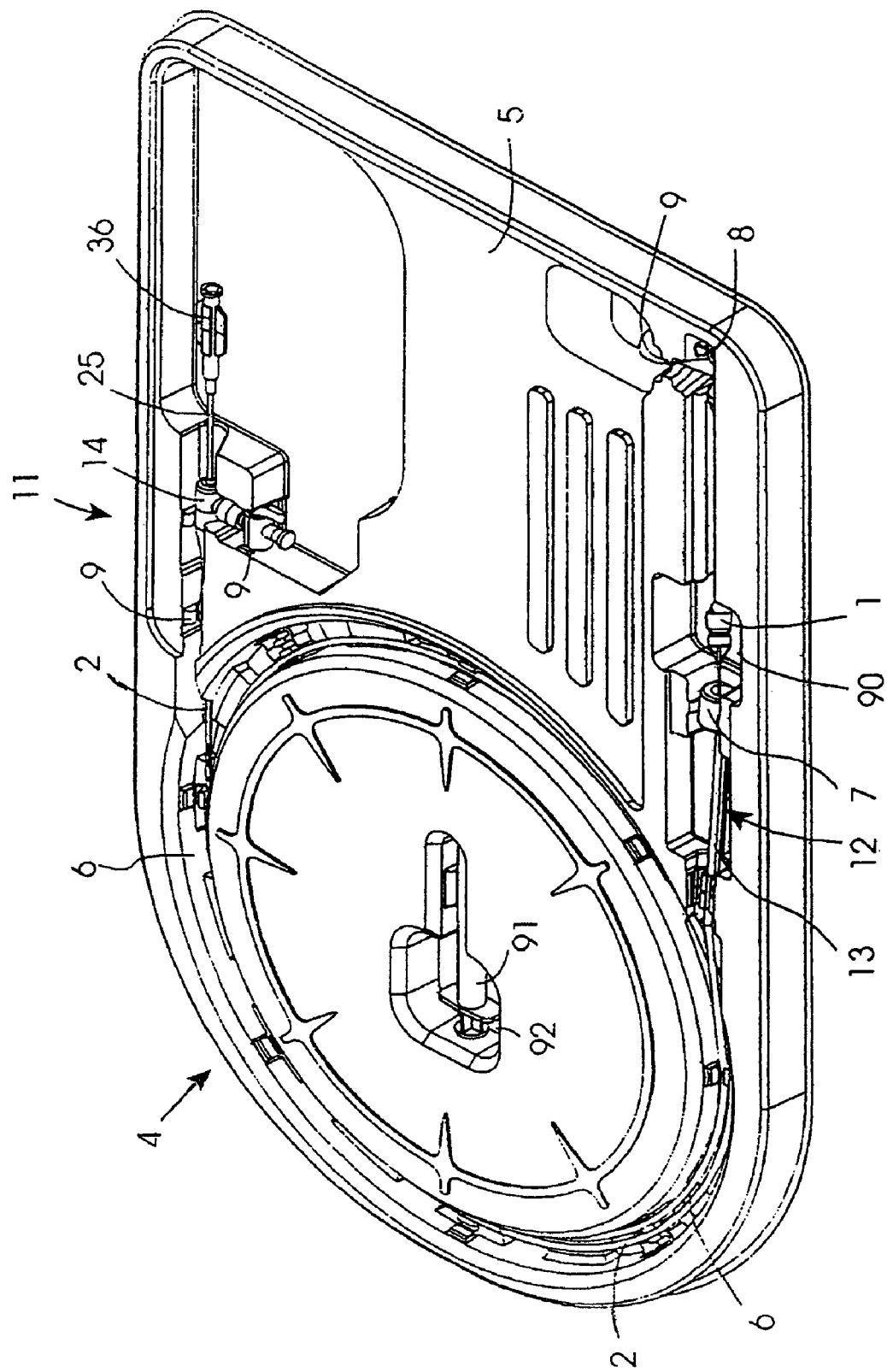
FIG. 1 is a perspective view of an embolic protection system pack.
Figure 2:
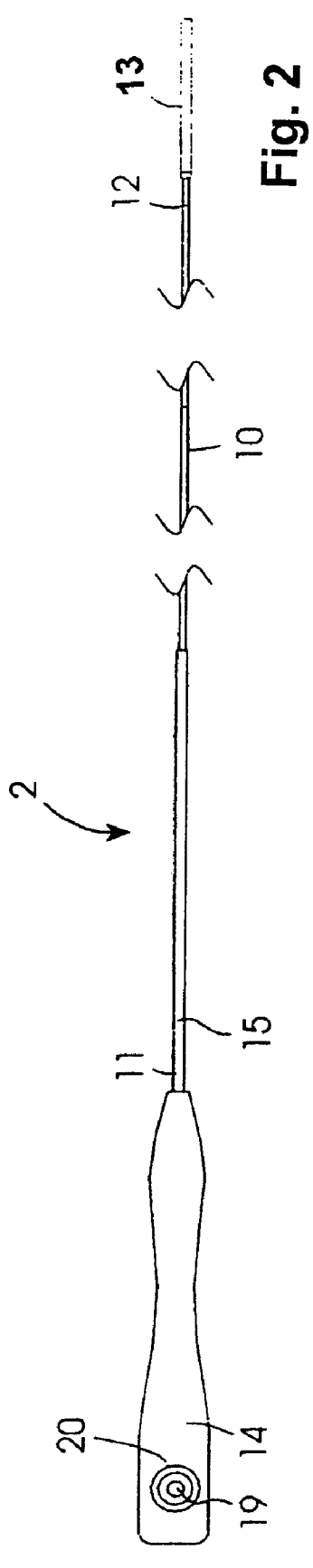
FIG. 2 is a plan view of a delivery catheter of the embolic protection system.

Referring to the drawings there is illustrated a transvascular embolic protection system according to the invention for safely capturing and retaining embolic material released during an interventional procedure while maintaining blood flow.

The embolic protection system comprises an embolic protection device 1, a delivery catheter 2 for delivery of the embolic protection device 1 to a desired location in the vascular system and a proximal stop for deployment of the embolic protection device 1. The device 1 is collapsible from an expanded deployed configuration to a retracted delivery configuration. The delivery catheter 2 has a pod 13 at the distal end to define a reception space for the embolic protection device 1 in the collapsed delivery configuration. The proximal stop in this case is provided by the distal end 27 of an inner catheter 25 which extends towards the pod 13 of the delivery catheter 2 for deployment of the embolic protection device 1 from the pod 13.

In use, the embolic protection device 1 is loaded into the pod 13 of the delivery catheter 2 which is delivered over a pre-positioned guidewire 99. At a desired location the inner catheter 25 is moved relative to the delivery catheter 2 to deploy the embolic protection device 1 from the pod 13. The delivery and inner catheters 2, 25 are then withdrawn leaving a bare guidewire 99 over which various devices such as a dilation balloon and/or a stent can be advanced to the treatment site. Embolic material dislodged during the treatment procedure(s) is collected in the embolic protection device 1. After treatment, the device 1 may be retrieved into a retrieval catheter 3. The guidewire 99 may be left in place for further catheter advancements or may be withdrawn with or subsequent to the withdrawal of the retrieval catheter 3.

Referring in particular to FIG. 1 a pack 4 is provided to safely store and prepare the embolic protection system for use. The pack 4 comprises a vacuum-formed tray 5, typically of PETG. The tray 5 has a channel 6 extending in a looped configuration around the tray 5 for receiving the delivery catheter 2. The delivery catheter 2 has a proximal end 11 and a distal end 12. A handle 14 is provided at the proximal end 11, and the inner catheter 25 which extends through the delivery catheter 2 has a luer 36 at the proximal end. The luer 36 is located in the tray 5 adjacent to the handle 14. The pod 13 is provided at the distal end 12 of the inner catheter 2. A loading device 7 in the form of a funnel piece is mounted in the tray adjacent to and, in this case extending into the pod 13. The embolic protection device 1 is mounted in its expanded configuration in a well 90 in the tray 5 adjacent to and extending into the loading device 7. A pushing device 8 for loading the collapsible embolic protection device 1 is mounted in the tray 5 adjacent to the embolic protection device 1. A syringe 91 is also mounted in a recess 92 of the tray 5. The syringe 91 is used to flush the system and, after flushing, the pushing device 8 is used to push the embolic protection device 1 through the loading device 7 and into the pod 13 of the delivery catheter 2 in the collapsed configuration. The delivery catheter 2 is now ready for advancement over the guidewire 99.

Figure 3:
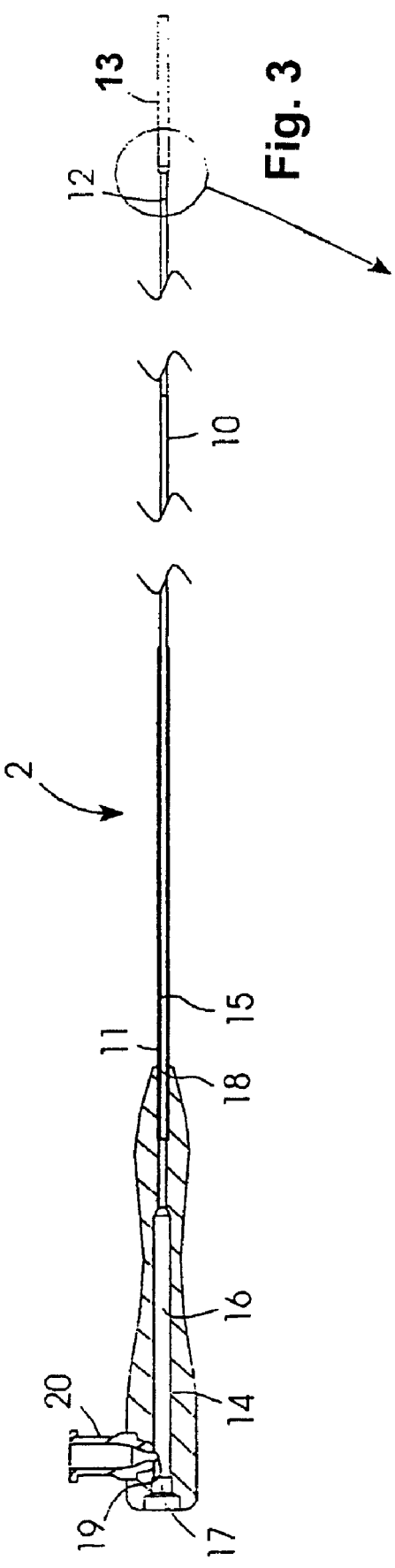
FIG. 3 is a side, partially cross-sectional view of the delivery catheter of FIG. 2.
Figure 4:
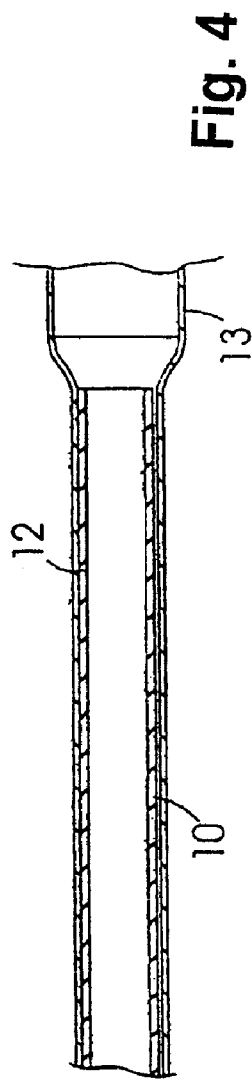
FIG. 4 is an enlarged view of part of the delivery catheter of FIG. 3.
Figure 5:
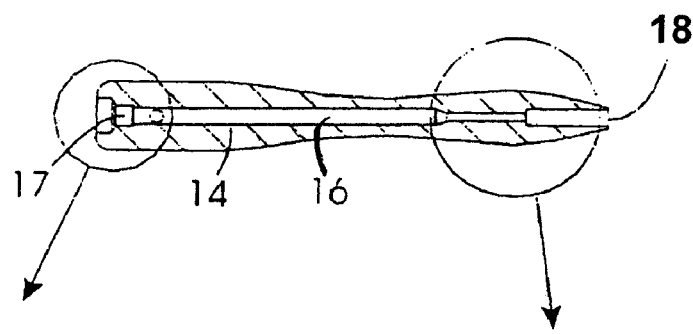
FIG. 5 is a side, partially cross-sectional view of a handle piece of the delivery catheter of FIG. 3.
Figure 6:
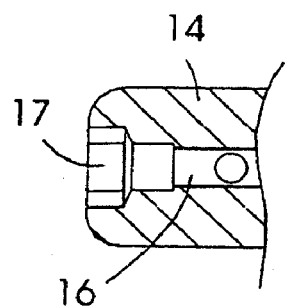
FIG. 6 is an enlarged view of part of the handle piece of FIG. 5.
Figure 7:
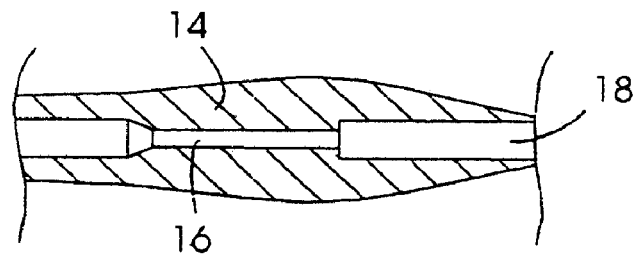
FIG. 7 is an enlarged view of another part of the handle piece of FIG. 5.
Figure 8:
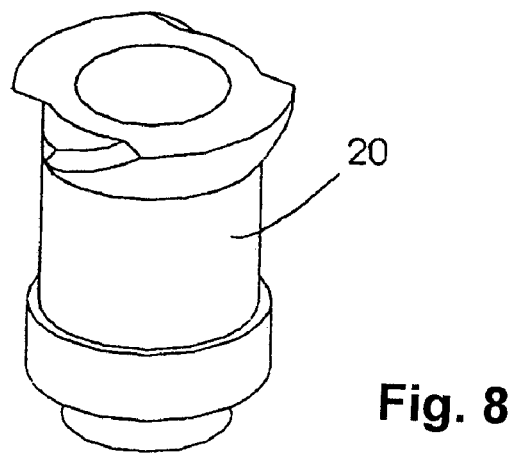
FIG. 8 is a perspective view of a female luer of the delivery catheter of FIG. 3.

Referring now to FIGS. 2 to 8, the delivery catheter 2 is illustrated in more detail. The delivery catheter 2 comprises a tubular body 10, typically of polyimide, or nylon extending between a proximal end 11 and a distal end 12. At the distal end 12 of the tubular body 10 a pod 13 is provided, the pod 13 having a smaller wall thickness and in this case a larger internal diameter, as illustrated in FIG. 4, to define a reception space for receiving the embolic protection device in a collapsed configuration. The handle 14, illustrated in detail in FIGS. 5 to 7, is attached to the proximal end 11 of the tubular body 10, with a strain relief member 15 extending from the handle 14 partially along the tubular body 10. The handle 14 defines a central lumen 16 extending between a proximal opening 17 and a distal opening 18. A side port opening 19 is provided in the handle 14, the side port 19 being in communication with the central lumen 16 (FIG. 3). A female luer 20, as illustrated in FIG. 8, is also provided, the luer 20 being fixedly mounted in the side port 19. A double-start thread is provided at the free end of the luer 20 for threadable attachment of, for example, a flushing syringe 91 to the luer 20.

Figure 12A:
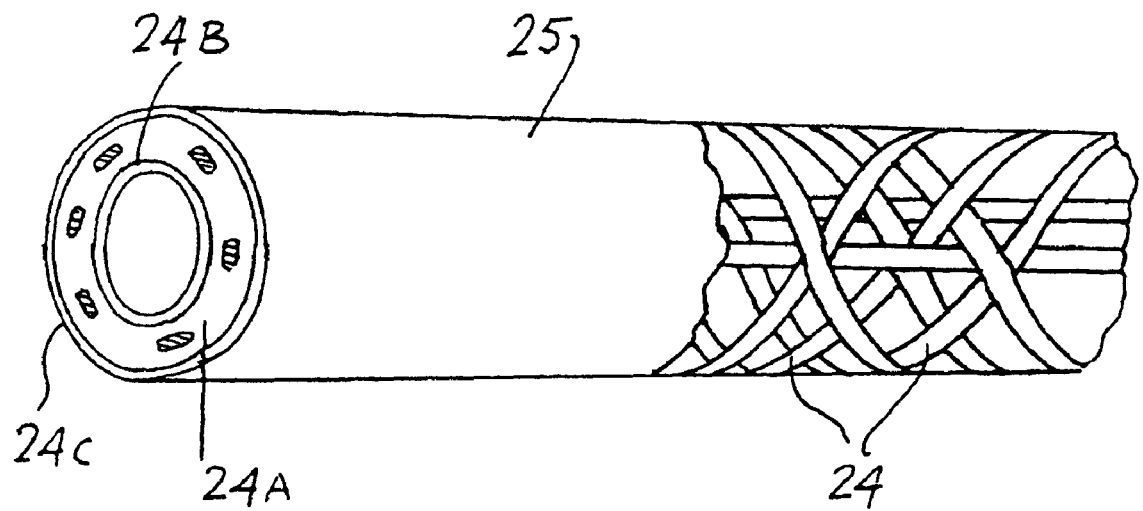
FIG. 12A is a perspective, partially cut-away view of the inner catheter.

In this case the proximal stop is provided by an inner catheter 25. As illustrated in FIGS. 9 to 12, the inner catheter 25 comprises a tubular body extending between a proximal end 26 and a distal end 27. The tubular body comprises an inner tubular stem 28 extending between the proximal end 26 and the distal end 27, and an outer tubular stem 29, typically of polyimide, extending from the proximal end 26 only partially along the inner stem 28, as illustrated in FIG. 10. The outer stem 29 terminates in a protruding O-ring shoulder 30. An annular collar 31 is slidably mounted to the outer stem 29 proximally of the O-ring shoulder 30 (FIG. 12). The female winged luer piece 36 is attached to the proximal end 26 of the stems 28, 29 by means of a flair connector 32. The winged luer 36 defines a central lumen 33 extending between a proximal opening 34 and a distal opening 35.

As illustrated in FIGS. 13 to 17, the inner catheter 25 is configured for insertion through the proximal opening 17 of the handle 14 and advancement through the handle 14, and the tubular body 10 until the collar 31 engages the handle 14 (FIG. 15) in the region of the proximal opening 17. The collar 31 is fixedly attached within the proximal opening 17 of the handle 14.

Figure 17:
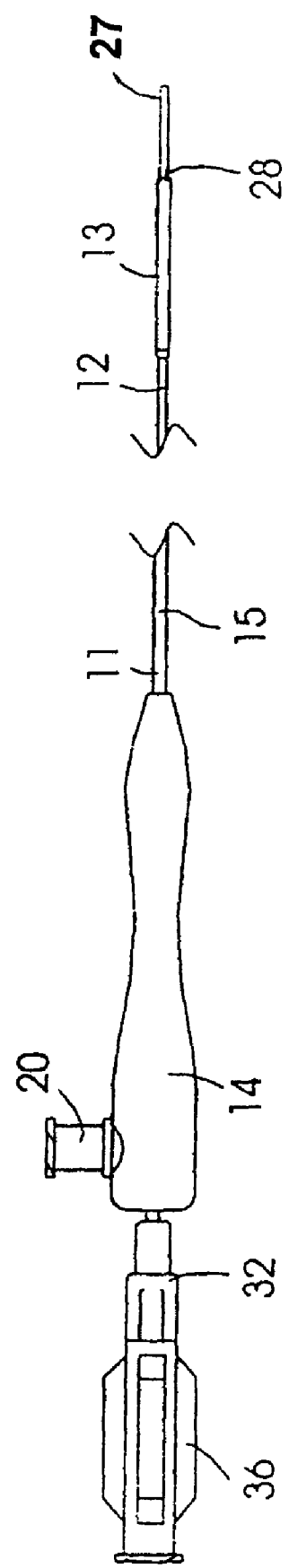
FIG. 17 is a side view of the catheter assembly of FIG. 14 with the inner catheter in a distal configuration of use.

The inner catheter 25 is slidable relative to the delivery catheter 2 between a retracted position, as illustrated in FIG. 14, in which the distal end 27 of the inner catheter 25 is proximal of the pod 13 defining the reception space in the delivery catheter 2 (FIG. 16), and an extended position, in which the distal end 27 of the inner catheter 25 extends distally of the pod 13 of the delivery catheter 2 (FIG. 17). Movement of the inner catheter 25 proximally relative to the delivery catheter 2 is limited by engagement of the O-ring shoulder 30 with the collar 31 (FIGS. 14 and 15).

The pod 13 of the delivery catheter 2 and the inner stem 28 of the inner catheter 25 at least partially comprise a stiff core, for example of a metallic material, such as stainless steel, encased in a more pliable body, for example of a plastics material such as polyimide. The cores comprise a mesh of longitudinally oriented strips of the stiff material and circumferentially oriented strips of the stiff material.

Accurate delivery of a filter to its intended location (a non-diseased vessel area) is a particularly important concern in tortuous anatomy where there is a limited area of non-diseased vessel. The accuracy of deployment is related to the build up of potential strain energy in delivery catheter systems. This strain energy is primarily a combination of strain energy produced in the outer and inner shaft during the deployment action. The designs described below referring in particular to FIGS. 4A and 12A detail a novel solution to these problems.

Figure 4A:
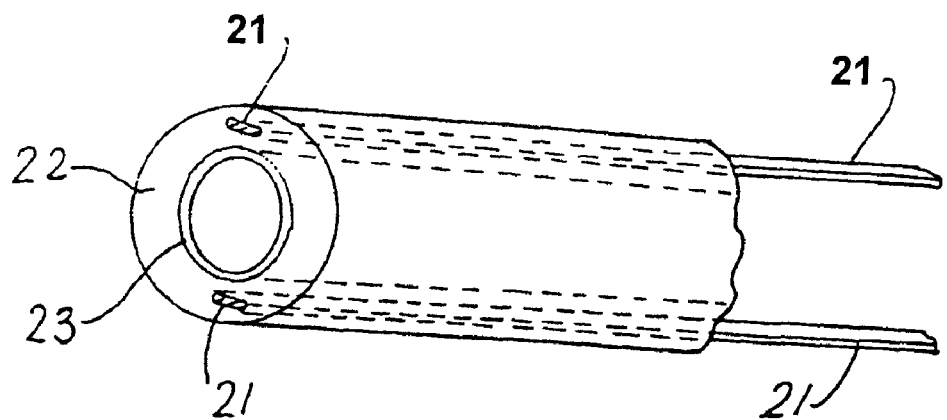
FIG. 4A is a perspective, partially cut-away view of the delivery catheter.

During the deployment action the outer shaft or delivery catheter 2 is subjected to high levels of tensile strain. The design/construction of the outer shaft 2 is such that the amount of strain energy that can be stored within the outer shaft is minimized. Low flexural stiffness is also desirable in catheter design to ensure good catheter flexibility, trackability and low insertion forces. These attributes are achieved by incorporating high tensile elements 21 within the wall construction of the outer shaft 2. These high tensile elements 2 can be high tensile longitudinal steel wires as shown in the example below or they may be flexible high tensile wires or fibers, carbon fibers and or kevlar fibers. These fibers/wires are contained within the wall 22 of the catheter which may be a polymeric material (detailed in FIG. 4A is a polyimide wall). These wires/fibers provide the outer shaft with high tensile modulus (minimal stretch) which results in a shaft that can not store much strain energy. The inclusion of the above high tensile elements 21 allows for a low profile outer shaft 2. This low wall thickness outer catheter shaft, therefore also has low flexural stiffness, good flexibility, trackability and subsequently low insertion force. The inner surface 23 of the lumen of this shaft 2 is a low friction (PTFE) material to minimize the friction strain energy incurred during the deployment action.

During the deployment action the inner catheter shaft 25 is subjected to high levels of compression strain. The design/construction of the inner shaft 25 is such that the modulus of compression is high which reduces the amount of strain energy that can be stored within the inner shaft 25. This is achieved by incorporating elements 24 with high compression modulus. These elements are contained within a material matrix 24A that further enhances the compression modulus of the inner shaft 25. The inclusion of the above high compression elements allows for a low profile outer shaft. The low wall thickness inner shaft will therefore also have low flexural stiffness, good flexibility and trackability. The example illustrated in FIG. 14A is a high compression modulus steel wire braid 24 contained within a polymeric matrix 24A. The inner lumen of the shaft 25 is made of a low friction (PTFE) material layer 24B. The outer surface of the shaft 25 is also provided with a low friction (FEP) material layer 24C. The layers 24B and 24C minimize the frictional strain energy incurred during delivery and deployment. Due to the combination of the above inner and outer shaft 2,25 the amount of strain energy that can be stored within the system during use is very low. Due to the low strain energy build up within the system a precise, controlled, low force deployment is achieved even in difficult vessel paths.

In this case, the embolic protection device 1 comprises a collapsible filter element 40 for delivery through a vascular system of a patient and deployment at a desired location in the vascular system. FIGS. 18 and 19 illustrate the filter element 40 in detail.

The filter element 40 comprises a collapsible filter body 41, a collapsible filter support frame 42 contacting the filter body 41, and an inner elongate sleeve 43 to which both the filter body 41 and the frame 42 are mounted. A proximal end 44 of the filter body 41 and a proximal end 45 of the frame 42 are both fixedly attached to a proximal end 46 of the sleeve 43, in this case by means of an adhesive bond. A distal end 47 of the filter body 41 and a distal end 48 of the frame 42 are free to slide over a distal end 49 of the sleeve 43.

The filter body 41 has a proximal inlet end and a distal outlet end. The inlet end of the filter body 41 has one or more, in this case two, large inlet openings 50, and the outlet end has a plurality of, in this case approximately three hundred, small outlet openings 51 sized to allow through passage of blood but to retain undesired embolic material within the filter body 41.

The filter support frame 42 is movable between a collapsed position for movement of the filter element 40 through a vascular system and an extended outwardly projecting position to support the filter body 41 in an expanded position. The frame 42 has a distal section 52, an intermediate section 53 for urging the filter body 41 in the expanded position into apposition with a vascular vessel wall, and a proximal section 54 extending proximally and radially inwardly of the intermediate section 53 (FIGS. 18 and 19).

At least part of the proximal section 54 of the frame is spaced distally of the inlet openings, 50 in the filter body 41 to accommodate inflow of embolic material through the inlets 50 and into the expanded filter body 41. The filter body 41 comprises one or more, in this case two, linking webs 55 between adjacent inlets 50, and a part of the proximal section 54 of the frame extends radially inwardly in alignment with the webs 55, as illustrated in FIG. 19, to avoid occluding the inlets 50 to the filter body 41 when the filter body 41 is in the expanded position. In this manner the possibility of embolic material becoming caught or hung-up on the proximal section 54 of the frame as the embolic material flows distally through the inlet openings 50 is minimized.

The proximal section 54 of the frame comprises one or more frame elements, in this case four. At least one frame element, in this case two, provides the part of the proximal section 54 which is spaced distally of the inlets 50, and at least one frame element, in this case two, provides the part of the proximal section 54 extending radially inwardly in alignment with the webs 55.

The proximal section of the frame runs generally parallel with a vessel wall and then turns radially inwards. The proximal arm(s) of the frame have a section that is displaced distally. The advantage of this displacement is that it creates an inlet path which is offset and therefore larger.

The frame elements are preferably of a shape memory material, such as Nitinol, or of a superelastic material, and may have a plating of gold or other dense material around the Nitinol. The frame elements facilitate movement of the frame 42 between the collapsed position and the extended outwardly projecting position. The frame 42 is electropolished.

The sleeve 43 defines a lumen 56 extending therethrough for exchange of the filter element 40 over the guidewire 99. The distal end 49 of the sleeve 43 is engageable with a stop such as a stop on the guidewire 99. This is particularly useful for retrieval of the filter element 40 from, a vascular system. The sleeve 43 is typically of polyimide.

The sleeve 43 acts as a barrier between the lumen 56 through which a guidewire may be exchanged, and the internal annular volume of the filter body 41 within which embolic material is retained. In particular, the proximal end 46 of the sleeve 43 is proximal of the inlets 50, and the distal end 49 of the sleeve 43 is distal of the small outlets 51. This ensures that all blood flows into the filter body 41 through the inlets 50, through the filter body 41 and out of the fitter body 41 through the small outlets 51 which are sized to retain undesired embolic material within the filter body 41. The sleeve 43 prevents escape of any embolic material from the filter body 41 into the lumen 56, for example, during exchange of medical devices over a guidewire received within the lumen 56, or during retrieval of the filter element 40.

A guide olive 57 is provided for atraumatic delivery of the filter element 40 through a vascular system, the guide olive 57 forms an extension of the distal end 47 of the filter body 41 and tapering distally inwardly for a smooth transition profile. In this case, the guide olive 57 is integral with the filter body 41 and is of the material Pellethane. As illustrated in FIGS. 18 and 19, the guide olive 57 extends distally of the distal end 49 of the sleeve 43.

In use, the region of a vasculature in which the filter element 40 is deployed is substantially straight for a length at least equal to the longitudinal length of the filter element 40 to ensure apposition of the filter body 41 with the vasculature wall. By directly mounting the guide olive 57 at the distal end 47 of the filter body 41, the overall longitudinal length of the filter element 40 is reduced to define a longitudinally compact filter element 40. Thus, the user has greater freedom when choosing a site in a vasculature to deploy the filter element 40 because the length of the vasculature which is required to be straight is correspondingly reduced.

As illustrated in FIGS. 18 and 19, the distal end 48 of the frame 42 acts to reinforce the proximal section of the guide olive 57 and prevents flaring of the sleeve 43. The guide olive 57 has a soft distal tip 58.

Two gold marker bands 59, 60 are provided mounted to the sleeve 43. One marker band 59 is fixedly attached to the olive 51 and one marker band 60 is fixedly attached to the proximal end 45 of the frame 42. The marker bands 59, 60 assist in visualization of the filter element 40 during an interventional procedure.

A transition element 61 is fixedly mounted to the proximal end 46 of the sleeve 43, in this case by means of an adhesive bond. The transition element 61 is sized to fit made the lumen of the delivery catheter 2 to provide a smooth stiffness transition and prevent kinking.

Figure 20:
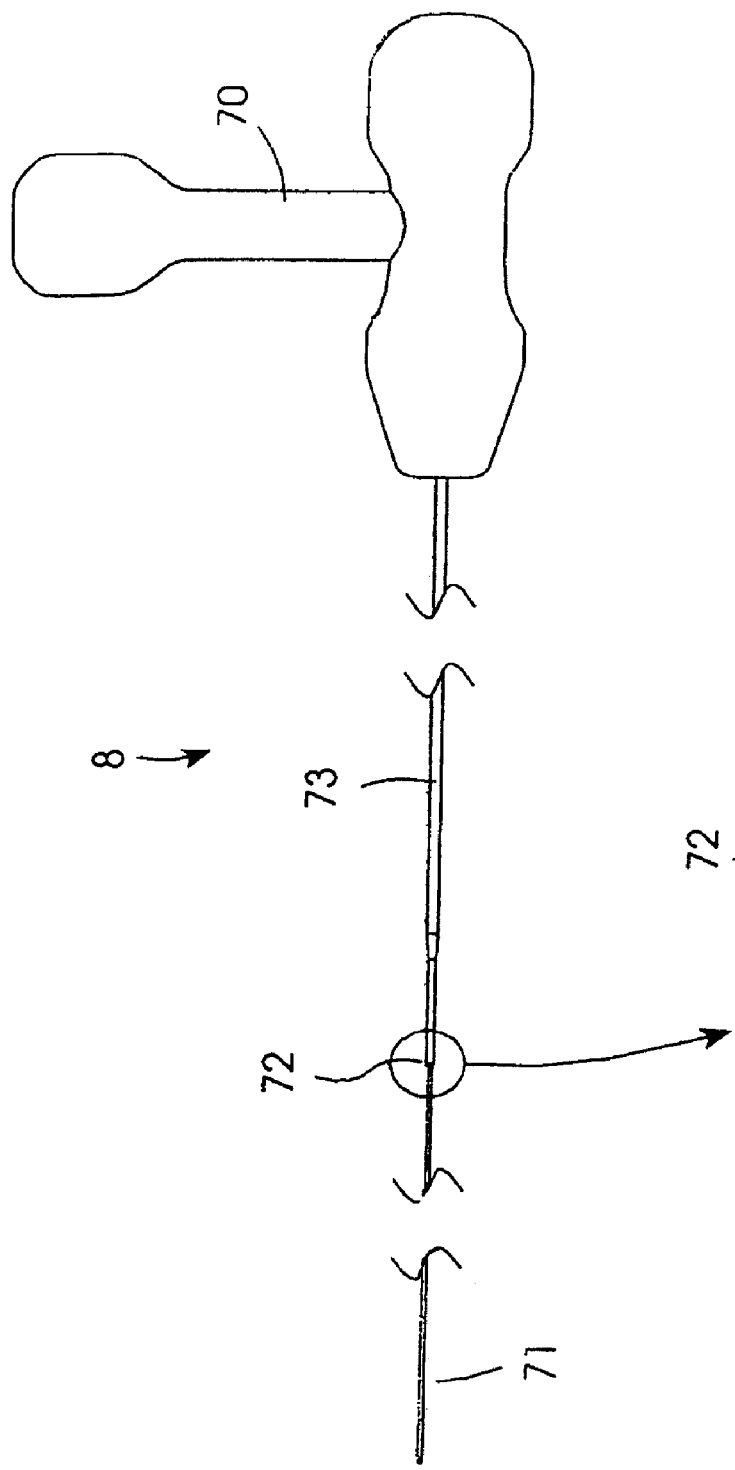
FIG. 20 is a side view of a pushing device of the embolic protection system.
Figure 21:
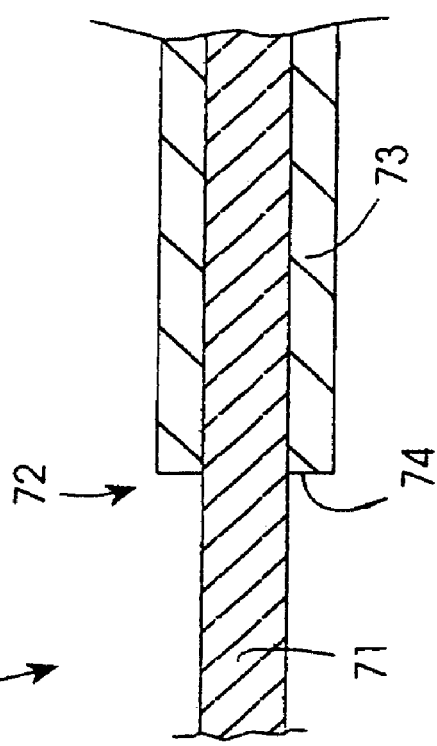
FIG. 21 is a side, cross-sectional view of a part of the pushing device of FIG. 8.

Referring now to FIGS. 20 and 21, the pushing device 8 for loading the collapsible filter element 40 into the pod 13 of the delivery catheter 2 is illustrated. The pushing device 8 comprises a handle 70 for gripping the pushing device 8 and an elongate stem in this case provided by a wire 71, extending from the handle 70 for threading through the lumen 56 of the filter element 40. The wire 71 defines a distal stop 72 for releasably engaging with the distal end 49 of the sleeve 43 of the filter element 40 to push the filter element 40 into the pod 13 of the delivery catheter 2.

As illustrated in FIG. 21 the distal stop 72 is provided by an end 74 of an outer hypotube 73 which extends from the handle 70 partially along the wire 71. The free end 74 of the hypotube 73 forms a step from the small diameter wire 71 proximal of the step to the larger diameter hypotube 73 distal of the step. The small diameter is preferably approximately 0.014" (0.3556 mm), and the large diameter is preferably approximately 0.018" (0.4572 mm). The hypotube 73 may be attached to the wire 71 by any suitable means, such as an adhesive means, or a mechanical keying means, or by brazing, or soldering, or welding, or by any other suitable means.

The wire 71 may have a low friction coating, for example of polytetrafluoroethylene, for ease, of threading of the wire 71 through the filter element 40. The handle 70 facilitates ease of gripping and of use of the pushing device 8.

It will be appreciated that the distal stop 72 may be provided integral with the wire 71, for example by machining a step in the wire 71.

It will further be appreciated that the large diameter portion distal of the step may be only a locally defined feature on the wire 71 that does not extend distally to the handle 70.

The loading device 7 is illustrated in detail in FIGS. 22 and 23. The loading device 7 defines a funnel having an inlet end 80 and an outlet end 81, the inlet end 80 defining a larger cross-sectional area than the outlet end 81, and the outlet end 81 being configured for co-operative alignment with the reception space of the delivery catheter 2.

The loading device 7 has means for radially compressing the filter element 40 from the extended outwardly projecting position to the collapsed position. In this case, the loading device 7 comprises a main support 82 having a funnel-shaped bore formed from a frusto-conical filter element receiving portion terminating in a cylindrical portion formed by a thin walled loading tube 83 projecting from the main support 82 for positioning within the reception space of the delivery catheter 2.

The cone angle of the bore is chosen from an angle in the range of between 15° and 65°, preferably between 35° and 45°.

The loading tube 83 is preferably formed from polyethyleneterephthalate (PET), and is mounted on a metal spigot 84, typically a grit blasted hypotube, by a combination of a polyolefin shrink tube bond and an adhesive bond. The metal spigot 84 is adhesively fixed to the main support 82 which is formed from "Perspex" or a similar material. The loading tube 83 may be coated with a lubricant.

Referring to FIG. 23A there is illustrated an alternative loading device 85 in which an outer support 86 is provided around the pod 13 of the delivery catheter 2. A smooth transition is provided by a funnel section 87 and the distal end of the pod 13. The area between the outer support 86 and the pod 13 may be a wetted annular space for ease of mounting and demounting.

Referring to FIGS. 1 and 24 to 29, the tray 5 will now be described in more detail. The tray includes integral projections 9 that extend into various recesses. The projections 9 releasably support the loading device 7 in cooperative alignment with the delivery catheter 2 before loading and during the loading procedure. In particular, the loading device 7 is supported with the loading tube 83 extending proximally into the reception space of the delivery catheter 2 before loading and during the loading procedure. In addition, the projections 9 on the channel wall are configured to releasably support the pushing device 8 in a position in which the distal stop 72 does not engage the filter element 40 before the loading procedure commences.

Figure 24:
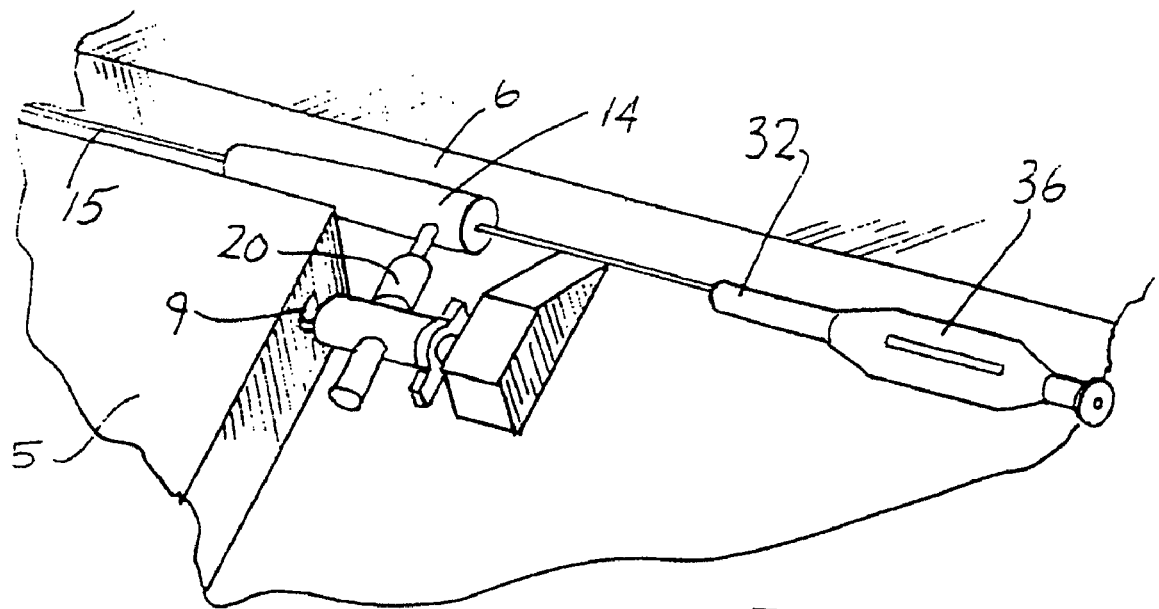
FIGS. 24 to 27 are schematic views illustrating release and flushing of the catheter assembly of FIGS. 13 to 17.

The projections 9 are also configured to releasably support the luer 20 of the delivery catheter 2 in the horizontal position illustrated in FIGS. 1 and 24. In this position it is not possible to slide the delivery catheter 2 proximally in the channel 6, or, in the configuration illustrated, to flush the delivery catheter 2 through the luer 20.

A liquid retaining bath 90 is provided by recesses in the tray 5, the bath 90 having a depth sufficient to accommodate in a totally submerged state the reception space of the delivery catheter 2 and the filter element 40 for submerged loading of the filter element 40 through the loading device 7 and into the pod 13 of the delivery catheter 2. As illustrated in FIG. 1, the channel 6 communicates with the bath 90, and a ramp is provided at an end of the channel 6 communicating with the bath 90 to direct the reception space downwards towards the bottom of the bath 90 but supporting the pod 13 of the delivery catheter 2 above the bottom of the bath 90 by means of a step.

The syringe 91 is provided for flushing the delivery catheter 2, the inner catheter 25, the loading device 7 and the filter element 40. The recess 92 is provided in the tray 5 for snap retention of the syringe 91 before use.

The components of the embolic protection system are placed in the pack 4 in the following manner. The loading device 7 is snapped into place in the channel 6, with the projections 9 releasably supporting the loading device 7 in the position illustrated in FIG. 1.

The inner catheter 25 is inserted through the proximal opening 17 of the handle 14, and advanced through the handle 14 and the tubular body 10 until the collar 31 engages the proximal opening 17 of the handle 14. The collar 31 is fixedly attached within the proximal opening 17 of the handle 14 by pushing the collar 31 home to create an interference fit between the collar 31 and the proximal opening walls. This catheter assembly is then looped through the channel 6 and held in place so that the loading tube 83 of the loading device 7 extends proximally into the pod 13 of the delivery catheter 2.

The wire 71 of the pushing device 8 is then threaded through the filter element 40, a proximal end of the wire 71 is inserted through the loading device 7 and extended partially through the inner catheter 25. The handle 70 is snapped into place in the channel 6 by the projections 9. In this configuration the filter element 40 is slidable over the wire 71 but is normally positioned within the bath 90, as illustrated in FIG. 1. The projections 9 retain the pushing device 8 in a position in which the distal stop 72 is spaced distally of the bath 90, and so the distal stop 72 does not engage the filter element 40 in this storage configuration, as illustrated in FIG. 1.

The syringe 91 is snapped into place in the recess 92, and the assembled pack 4 is now ready to be sealed and stored until required for use.

In this storage configuration the filter element 40 is in the expanded configuration. This is an advantageous arrangement. If the filter element 40 was loaded into the delivery catheter 2 and stored in the collapsed position for a long period of time, the filter element 40 would be subject to material deformation, in particular to material creep. The assembled pack 4 of the invention may be safely stored for long periods in a packaged configuration without risk of filter element material deformation. The pack 4 is placed in a porch and sealed.

Figure 25:
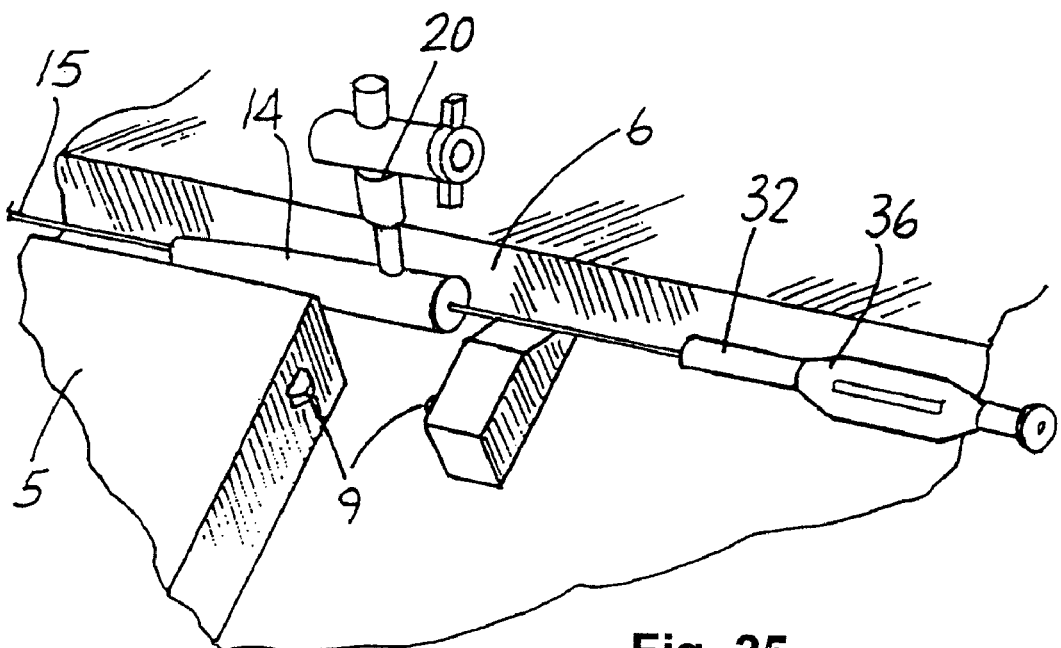
Figure 27:
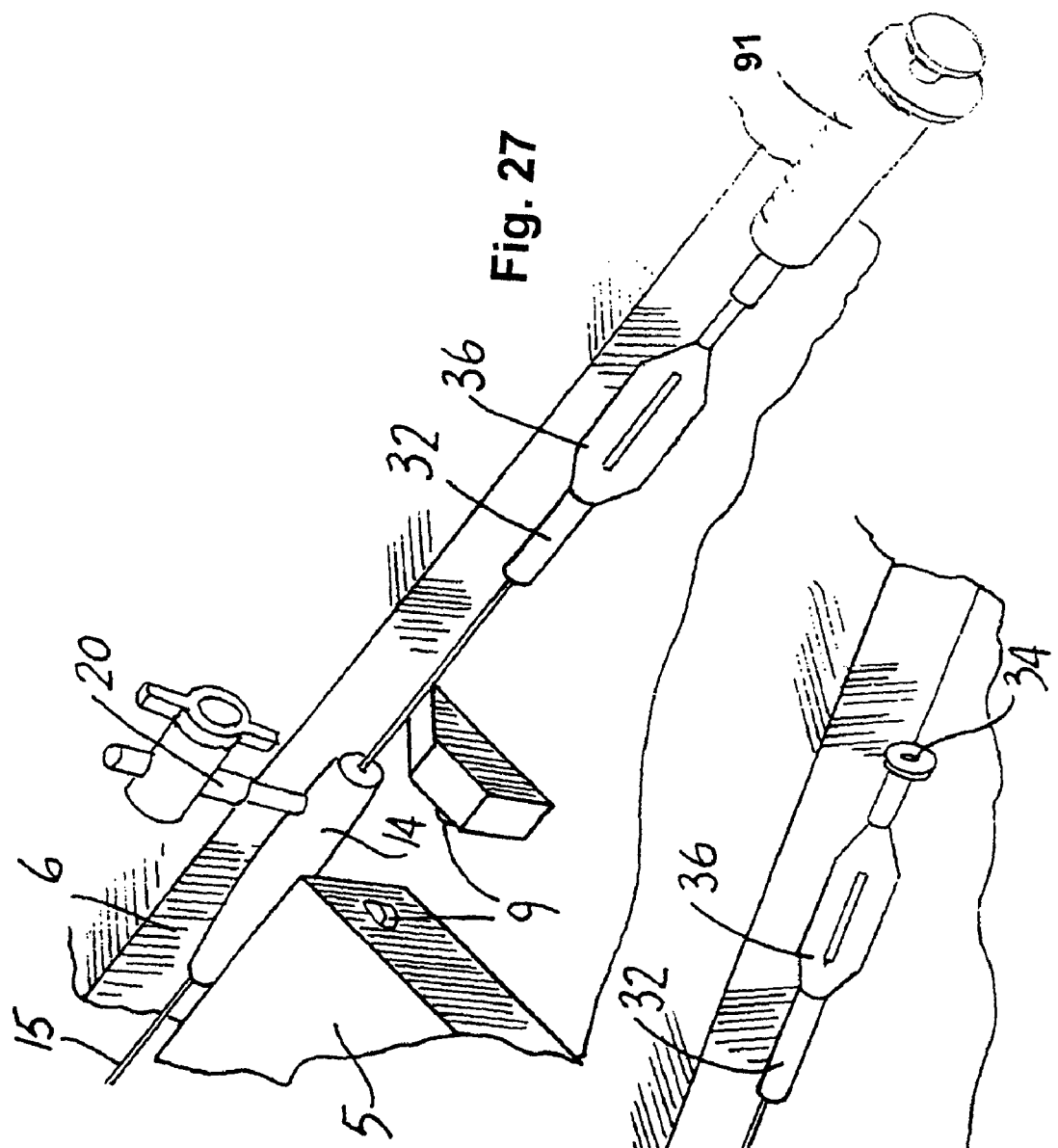
Figure 26:
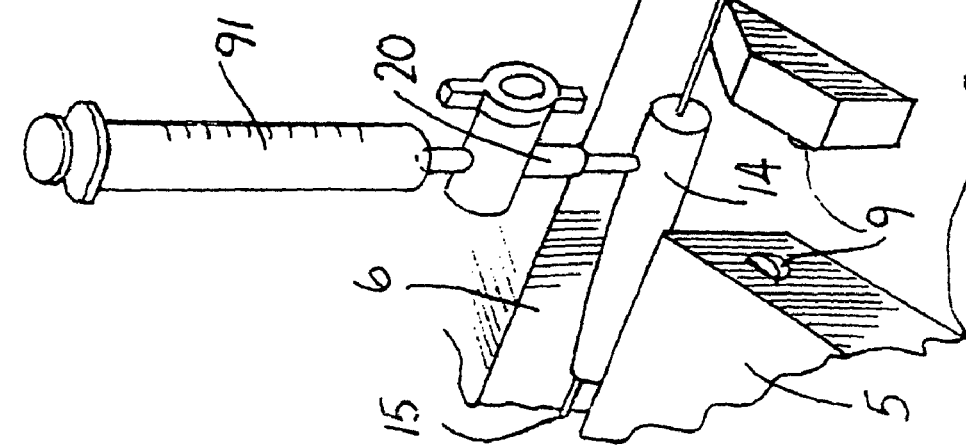

When the assembled pack 4 is required for use, the seal is broken, the pack 4 is removed and the syringe 91 is removed from the recess 92. The luer 20 of the delivery catheter 2 is rotated through 90° in a "bolt-action" to release the luer 20 from the snap-fit retaining projections 9 in the tray 5, as illustrated in FIGS. 24 and 25. The delivery catheter 2 is now slidable proximally in the channel 6, and the luer 20 is now accessible for flushing (FIG. 25). The syringe 91 is used to flush the delivery catheter 2 through the luer 20 (FIG. 26) and to flush the inner catheter 25 through the proximal opening 34 in the female luer piece 36 of the inner catheter 25 (FIG. 27). A saline solution is generally used for flushing the catheters 2, 25. The syringe 91 is also used to fill the bath 90 with saline solution, thereby immersing the filter element 40, the reception space of the delivery catheter 2 and the loading device 7 in the saline solution. This ensures all removed from the system.

This flushing step is performed shortly before intended use. The filter element 40 is completely visible and accessible to the user during prepping in this way, the user can squeeze or pinch parts of the filter element 40 to ensure the filter element 40 is completely flushed of air. This is difficult if the filter element 40 was loaded into the delivery catheter 2 upon assembly and stored for a potentially long period in the collapsed position.

Figure 28:
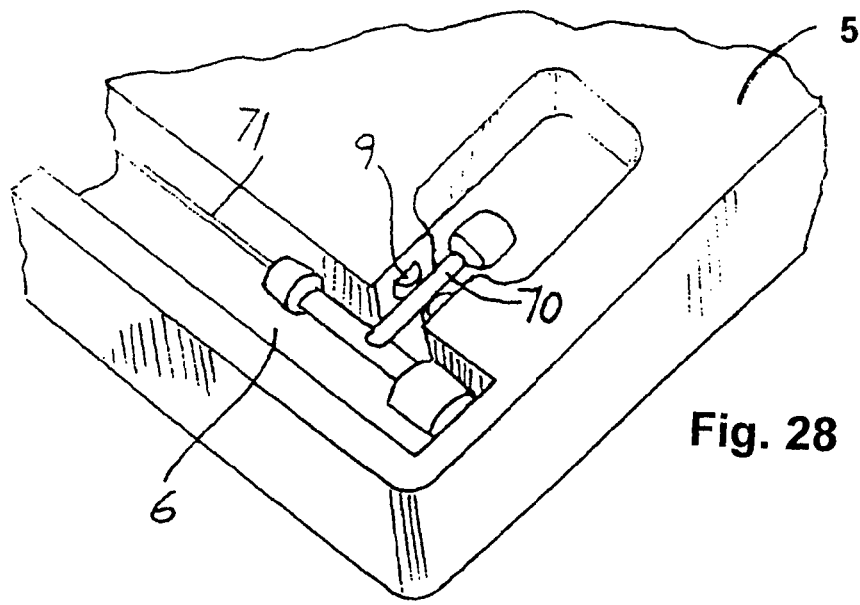
FIGS. 28 and 29 are schematic views illustrating release of the pushing device of FIGS. 20 and 21.
Figure 29:
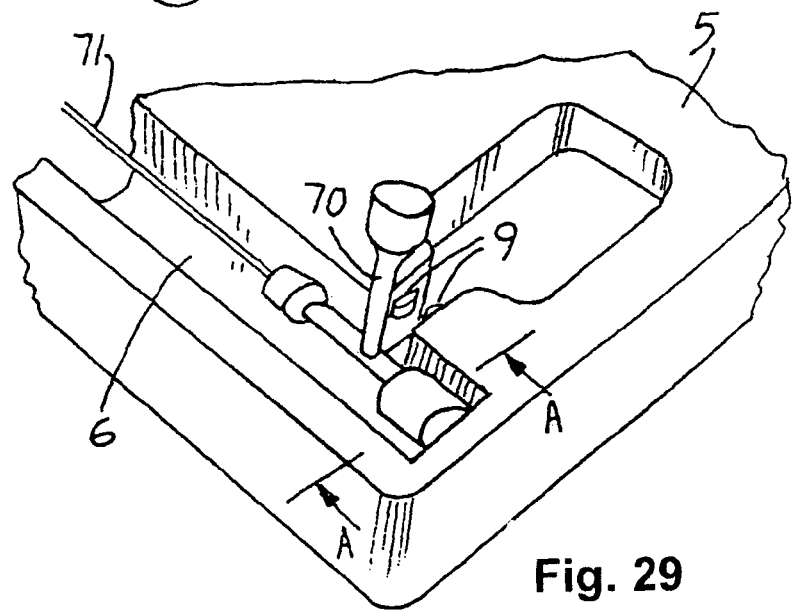
Figure 29A:
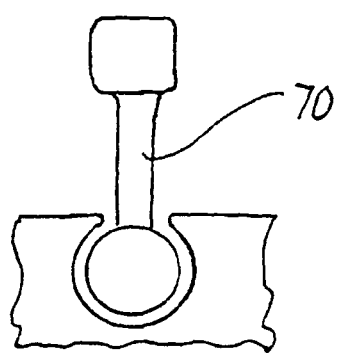
FIG. 29A is a cross sectional view on the line AA in FIG. 29.

The flushed filter element 40 is now ready for loading into the pod 13 of the delivery catheter 2. The pushing device 8 is rotated through 90° in a "bolt action" to release the handle 70 from the snap-fit retaining projections 9 in the tray 5, as illustrated in FIGS. 28 and 29. In this configuration the pushing device is still retained to the tray (FIG. 29A). The pushing device 8 is now free to slide proximally in the channel 6 (FIG. 30), until the distal stop 72 engages with the distal end 49 of the sleeve 43 of the filter element 40 (FIGS. 31A and 31B). Continued pushing of the pushing device 8 will push the filter element 40 proximally towards the loading device 7 (FIG. 31A), through the loading device 7, thereby collapsing the filter element 40 from the extended outwardly projecting position of FIG. 31A to the collapsed position of FIG. 32A, and into the pod 13 of the delivery catheter 2 (FIG. 32A) until the filter element 40 abuts the distal end 27 of the inner stem 28 of the inner catheter 25. Further pushing of the pushing device 8 moves the collapsed filter element 40 and the inner catheter 25 proximally until the O-ring shoulder 30 of the inner catheter 25 abuts the annular collar 31 fixed in the proximal opening 17 of the handle 14, as illustrated in FIGS. 14 and 15. An O-ring 39 is also provided between the shoulder 30 and the collar 31.

The loading device 7 has thus far remained in co-operative alignment with the delivery catheter 2. Because the luer 20 of the delivery catheter 2 has been released from the snap-fit retaining projections 9 in the tray 5, as illustrated in FIG. 32B, the catheter assembly is free to slide proximally in the channel 6 away from the loading device 7. When the pushing device 8 is further pushed proximally, this causes the inner catheter 25 to move proximally and with it the delivery catheter 2 due to the engagement of the O-ring shoulder 30 with the handle 14. In this manner, the delivery catheter 2, the inner catheter 25 and the collapsed filter element 40 are all moved together proximally away from the loading device 7, and thereby the loaded catheter assembly is disassociated from the loading device 7 (FIG. 33).

The loaded catheter assembly is then removed from the channel 6 leaving the loading device 7 and the pushing device 8 behind in the channel 6. The assembly of the loaded delivery catheter 2 and the inner catheter 25, as illustrated in FIG. 34, is now ready for insertion into a vascular system of a patient.

The filter element 40 is loaded into the pod 13 of the delivery catheter 2 by a simple, single-direction pushing action. This minimizes potential loading difficulties.

The components of the pack 4 are retained in the correct loading alignments by the tray 5. The pushing device 8 is completely separated from the loaded catheter assembly after completion of the loading procedure.

In addition, the loaded filter element 40 is not attached or associated in any way with the pushing device 8. Thus, the user is free to choose any suitable guidewire, as desired, for subsequent delivery of the filter element 40 through a vascular system of a patient.

Figure 35:
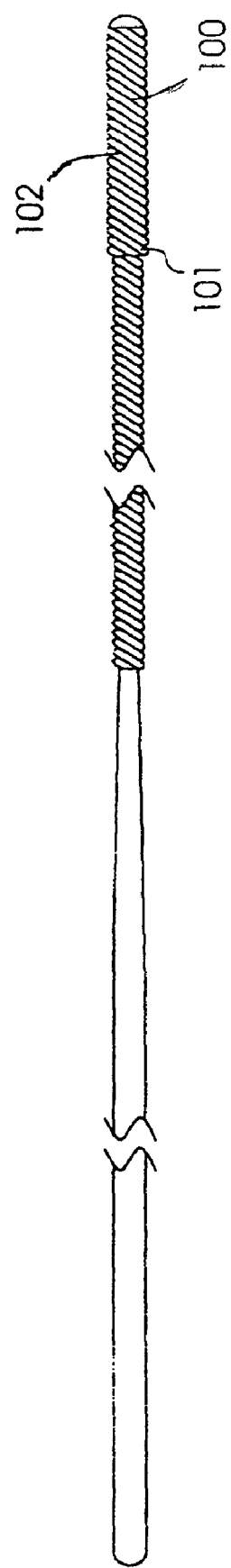
FIG. 35 is a side view of a guidewire of the embolic protection system.

Referring now to FIG. 35 the guidewire 99 of the embolic protection system is illustrated in detail. The guidewire 99 is suitable for the exchange of the filter element 40 through a vascular system of a patient over the guidewire 99. The guidewire 99 defines a distal end 100 and comprises a distal stop 101 to prevent relative movement of the filter element 40 distally of the distal end 100 of the guidewire 99. The portion of the guidewire 99 proximally of the distal stop 101 is bare for exchange of the filter element 40 and/or other medical devices over the guidewire 99.

In this case the distal stop 101 is provided by a wire coil 102 fixedly attached around the distal end 100 of the guidewire 99 (FIG. 35). The coil 102 has a larger outer diameter than the bare portion of the guidewire 99 to define a step from the small diameter bare portion of the guidewire 99 to the large diameter coil portion of the guidewire 99. The small diameter is preferably approximately 0.014" (03556 mm), and the large diameter is preferably 0.018" (0.4572 mm). A curve is typically formed towards the distal end 100 of the guidewire 99 to facilitate navigating and/or positioning the guidewire 99 in a vasculature.

The coil 102 may be attached to the small diameter portion of the guidewire 99 by an adhesive means, or by a mechanical keying means, or by brazing, or soldering, or welding, or by any other suitable means of attachment.

In this case, the guidewire 99 is partially of stainless steel, and partially of a radiopoque material to aid the user in positioning the guidewire 99 accurately in a vasculature. The guidewire 99 has a coating of a low friction material, for example of a fluoropolymer such as polytetrafluoroethylene, or of a silicone material, or of a hydrophilic material, for ease of advancement of the guidewire 99 through a vasculature and ease of exchange of the filter element 40 and/or other medical devices over the guidewire 99.

As illustrated in FIG. 35, the large diameter coil 102 extends distally of the step to the distal end 100 of the guidewire 99. However it will be appreciated that the large diameter portion of the guidewire 99 may extend distally of the step only a part of the distance to the distal end 101 of the guidewire 99. The large diameter portion may taper distally inwardly back to the small diameter in an arrow-head type shape or by gradually tapering.

Referring now to FIGS. 36 to 41, delivery and deployment of the filter element 40 at a desired location within a vasculature 110 is illustrated. The guidewire 99 will be selected to suit the geometry of the vasculature 110 to be negotiated, and/or the disease site, and/or the preference of the user.

Figure 36:
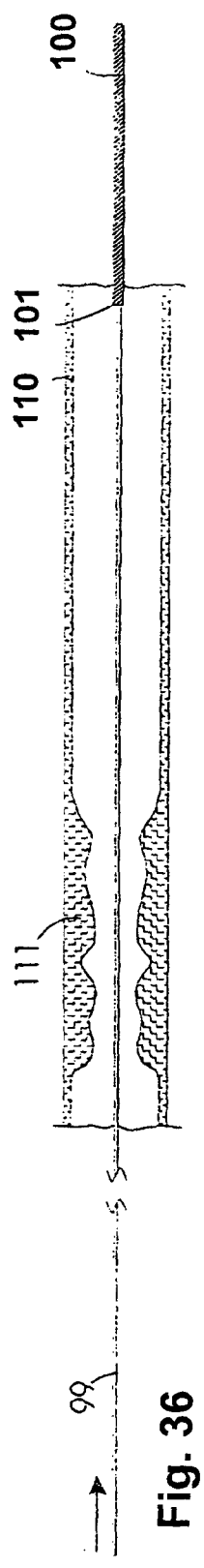
FIGS. 36 to 41 are schematic views illustrating delivery and deployment of the embolic protection device of FIGS. 18 and 19 in a vasculature.

The guidewire 99 is firstly inserted on its own into the vasculature system of a patient and advanced through the vasculature 110 until the distal stop 101 of the guidewire 99 is distal of a treatment site such as a region of stenosis 111 in the vasculature 110 (FIG. 36).

The curved distal end 100 of the guidewire 99 is often anchored in a bend in the vasculature 110 distally of the stenosed region 111 (FIG. 41) to facilitate some straightening of the anatomy by the user prior to delivery of the filter element 40.

Figure 37:
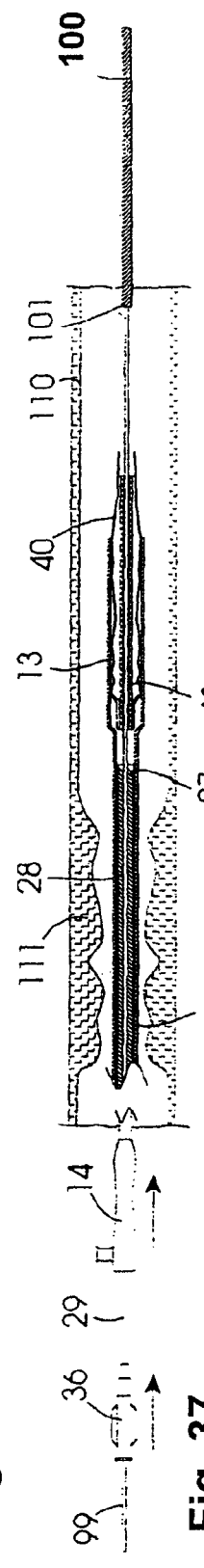

The loaded delivery catheter assembly of FIG. 34 is then inserted into the vasculature system and advanced over the guidewire 99 through the vasculature 110, until the pod 13 of the delivery catheter 2 with the collapsed filter element 40 therein is positioned at a desired location of the vasculature 110 distally of the stenosed region 111 (FIG. 37). At least part of the filter element 40, in this case part of the distal end 58 of the guide olive 57, protrudes distally out of the pod 13 of the delivery catheter 2 during advancement of the delivery catheter 2 through the vascular system to minimize trauma to the vessel walls. The olive also provides a stiffness transition.

Figure 38:
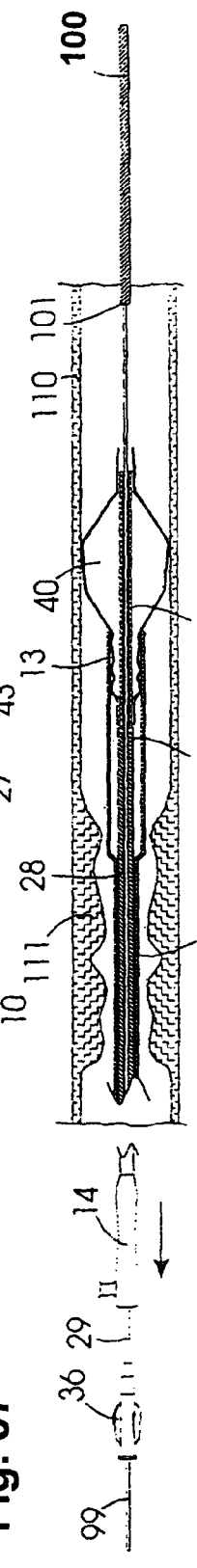
Figure 39:
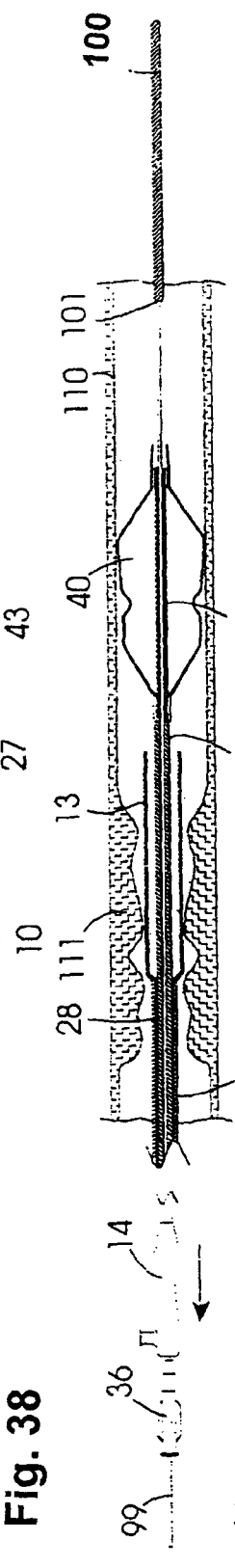

The delivery catheter 2 is refracted while maintaining the position of the inner catheter 25 (FIG. 38). In this way the distal end 27 of the inner stem 28 of the inner catheter 25 acts as a proximal stop against which the transition element 61 of the filter element 40 abuts, thus the distal end 27 of the inner stem 28 of the inner catheter 25 prevents retraction of the collapsed filter element 40 with the delivery catheter 2. As the restraining delivery catheter 2 is withdrawn, the filter element 40 is freed to expand from the collapsed, delivery configuration to the extended, outwardly projecting position of FIG. 39.

The filter element 40 may alternatively be deployed by advancing the inner catheter 25 while maintaining the position of the delivery catheter 2. In this case the distal end 27 of the inner stem 28 of the inner catheter 25 effectively acts as a pusher to eject the collapsed filter element 40 from the pod 13 of the delivery catheter 2, and thereby facilitate expansion of the filter element 40 to the deployed configuration of FIG. 39.

It will be appreciated that the filter element 40 may be deployed by any sufficient movement of the delivery catheter 2 proximally relative to the inner catheter 25, thereby engaging the distal end 27 of the inner stem 28 of the inner catheter 25 with the filter element 40 to facilitate deployment of the filter element 40.

The construction of the pod 13 of the delivery catheter 2 and the inner stem 28 of the inner catheter 25 prevent deformation of the pod 13 and the inner stem 28 during deployment of the filter element 40. In particular, elongation of the pod 13 and compression of the inner stem 28 are avoided. This ensures that the filter element 40 is accurately and smoothly deployed in the desired location in the vasculature 110.

In the extended outwardly projecting position the filter body 41 is in complete circumferential apposition with the wall of the vasculature 110 over a length substantially equal to the intermediate section 53 of the filter support frame 42.

Figure 40:
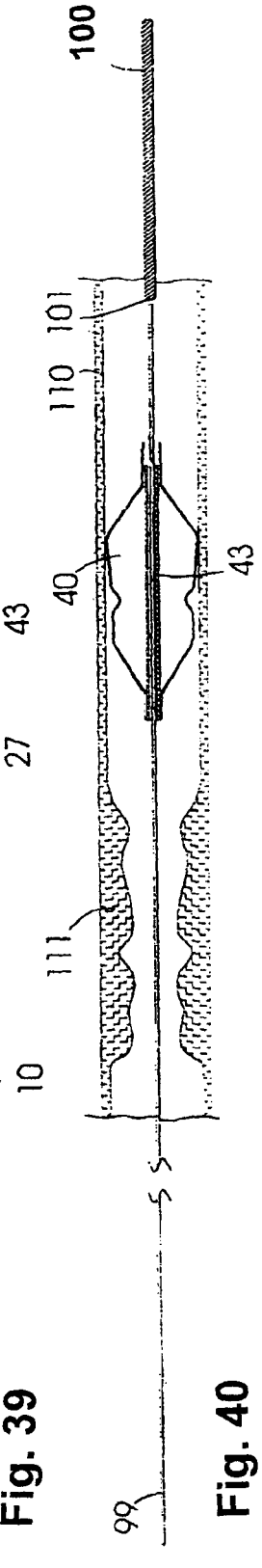
Figure 41:
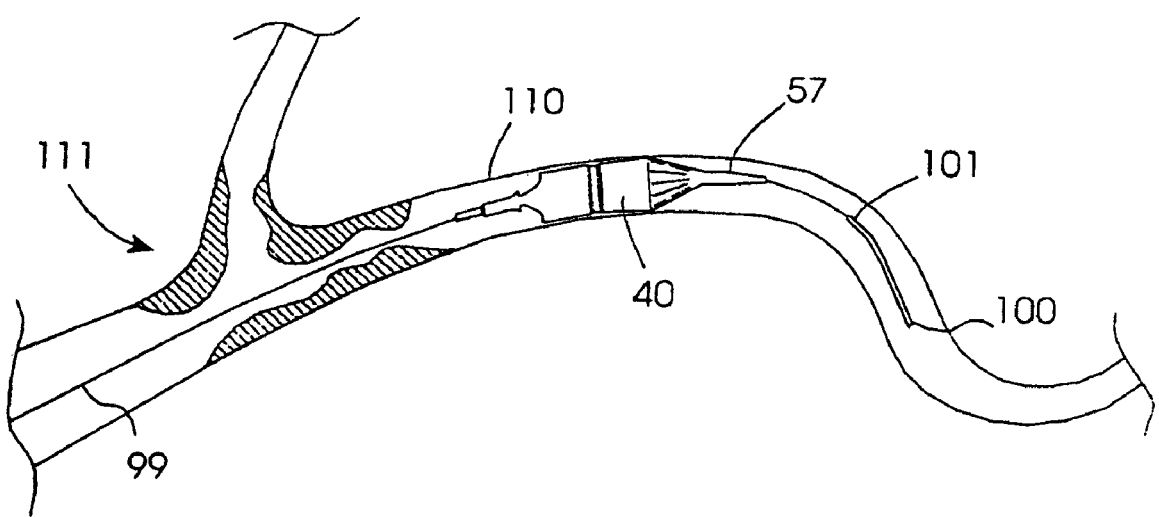

After deployment of the filter element 40 both the delivery catheter 2 and the inner catheter 25 are retracted and withdrawn from the vasculature 110, leaving the guidewire 1 in place in the vasculature 110, and the deployed filter element 40 in place in the vasculature 110 distally of the stenosed region 111 (FIGS. 40 and 41).

The guidewire 99 is not attached to the filter element 40, and thus the guidewire 99 is free to rotate and/or to move longitudinally relative to the deployed filter element 40. This is highly advantageous as it prevents any accidental movement of the guidewire 99 causing twisting and/or dislodging of the deployed filter element 40. Thus, the user has more freedom to carry out a treatment procedure on the stenosed region 111 without the risk of intimal abrasion, or of the deployed filter element 40 becoming dislodged or in some other way creating a potential flow path for embolic material around the filter element 40.

Figure 42:
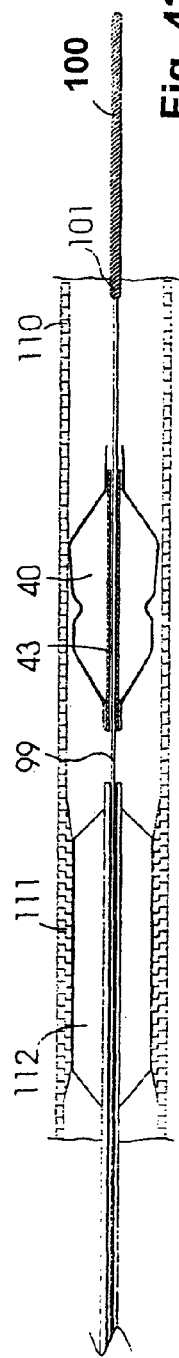
FIGS. 42 and 43 are schematic views illustrating treatment of the vasculature.
Figure 43:
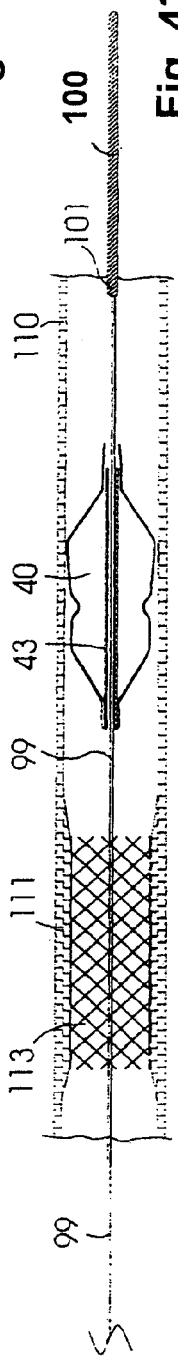

In addition, the portion of the guidewire 99 in place in the vasculature 110 proximal of the deployed filter element 40 is bare. This bare portion of the guidewire 99 facilitates the, exchange of a wide variety of different medical devices, for example a treatment means, over the bare guidewire 99 while the deployed filter element 40 remains in place in the vasculature 110. Examples of such medical devices are atherectomy devices to carry out an atherectomy procedure on the stenosed region 111, or an angioplasty balloon 112 to carry out an angioplasty procedure on the stenosed region 111, as illustrated in FIG. 42, or a stent 113 to carry out a stenting procedure on the stenosed region 111, as illustrated in FIG. 43, or any possible combination of these procedures, or any other therapeutic or diagnostic procedure. Any embolic material released during such an interventional procedure will be collected and safely retained in the filter element 40.

After completion of an interventional procedure, for example a treatment of the stenosed region 111, the retrieval catheter 3 is flushed, for example with a saline solution, using the syringe 91. In this case, the retrieval catheter 3 comprises an elongate tubular centering catheter 121. The centering catheter 121 has a tapered distal tip 122 which protrudes distally of a distal end 120 of the retrieval catheter 3 during advancement through the vasculature 110, as illustrated in FIG. 44, to prevent snagging of the retrieval catheter 3 on the stent 113, and to minimize vessel trauma.

Figure 44:
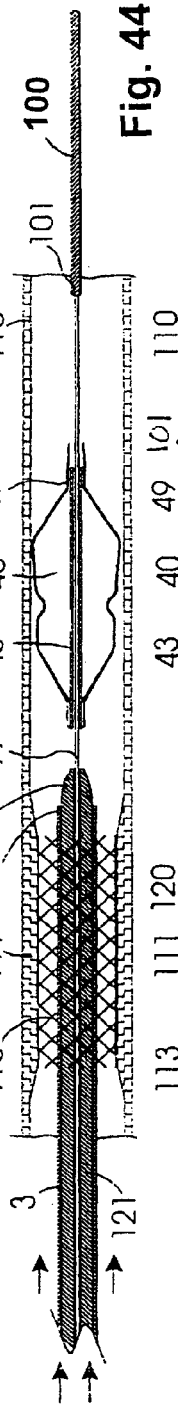
FIGS. 44 to 47 are schematic views illustrating retrieval of the embolic protection device of FIGS. 18 and 19 from the vasculature.

The retrieval catheter 3 is inserted into the vascular system and advanced over the bare guidewire 99 until the distal end 120 of the retrieval catheter 3 is distal of the stent 113 (FIG. 44). The retrieval catheter 3 is then further advanced distally over the guidewire 99 while maintaining the position of the centering catheter 121 until the distal end 120 of the retrieval catheter 3 is immediately proximal of the deployed filter element 40. The guidewire 99 is retracted to engage the distal stop 101 with the distal end 49 of the sleeve 43 of the filter element 40.

The distal stop 101 of the guidewire 99 may alternatively be engaged with the distal end 49 of the sleeve 43 of the filter element 40 by advancing the retrieval catheter 3 further distally to engage the deployed filter element 40 and push the deployed filter element 40 distally until the distal end 49 of the sleeve 43 of the filter element, 40 engages the distal stop 101 of the guidewire 99. In this case no retraction of the guidewire 99 is necessary to engage the distal stop 101 with the distal end 49 of the sleeve 43 of the filter element 40.

It will be appreciated that any suitable combination of advancement of the retrieval catheter 3 and retraction of the guidewire 99 may be employed to effect engagement of the distal stop 101 of the guidewire 99 with the distal end 49 of the sleeve 43 of the filter element 40.

Figure 45:
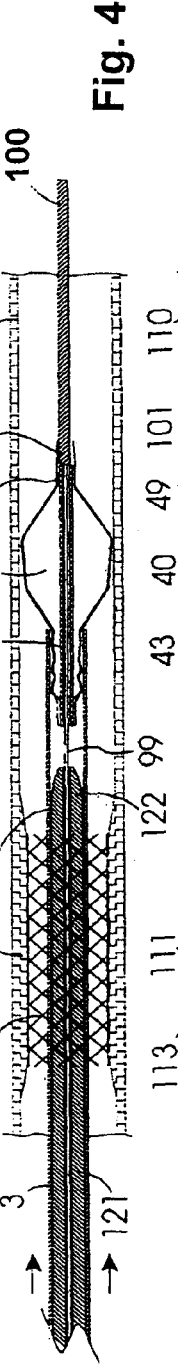
Figure 46:
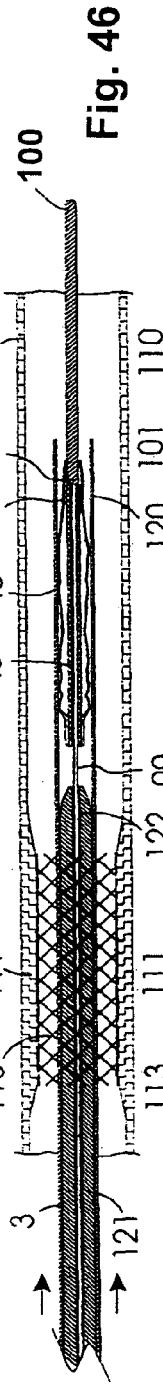

With the distal stop 101 of the guidewire 99 engaging the distal end 49 of the sleeve 43 of the filter element 40, the retrieval catheter 3 is advanced while maintaining the position of the guidewire 99 (FIG. 45). This causes the filter element 40 to collapse into the retrieval catheter 3 until the filter element 40 is retrieved into the retrieval catheter 3 (FIG. 46).

The filter element 40 may alternatively be retrieved into the retrieval catheter 3 by retracting the guidewire 99 while maintaining the position of the retrieval catheter 3 to collapse and retrieve the filter element 40 into the retrieval catheter 3. In this case the guidewire 99 acts to pull the filter element 40 proximally into the retrieval catheter 3.

It will be appreciated that the filter element 40 may be retrieved by any suitable movement of the retrieval catheter 3 distally relative to the guidewire 99.

The distal stop 101 facilitates retrieval of the filter element 40 by preventing the filter element 40 moving distally of the distal end 100 of the guidewire 99.

The guide olive 57 of the filter element 40 may or may not protrude distally out of the distal end 120 of the retrieval catheter 3 after collapse of the filter element 40.

The retrieval filter element 40 is then withdrawn from the vasculature 110 by withdrawing the retrieval catheter 3 and the centering catheter 121 together from the vasculature 110.

Figure 47:
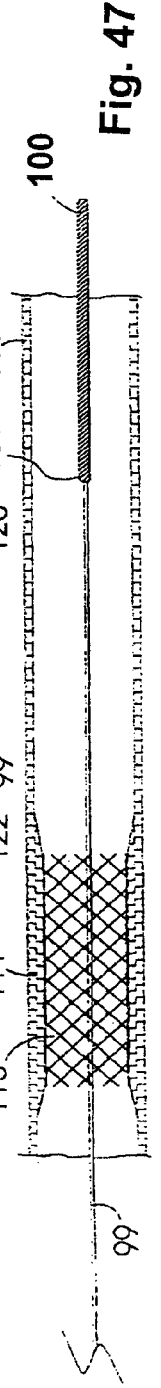

The guidewire 99 may be left in place in the vasculature 110 after the retrieval catheter 3, the centering catheter 121, and the retrieval filter element 40 have been withdrawn from the vasculature 110, as illustrated in FIG. 47. Alternatively the guidewire 1 may be withdrawn from the vasculature 110 upon withdrawal of the retrieval catheter 3, the centering catheter 121, and the retrieval filter element 40.

When the bare guidewire 99 is left in place in the vasculature 110 after withdrawal of the retrieval catheter 3, a further treatment or diagnostic means may be advanced over the bare guidewire 99 to access any desired location in the vasculature 110. The position of the bare guidewire 99 may be adjusted, proximally or distally, as desired, to suit a further treatment or diagnostic procedure. Otherwise a fluoroscopic assessment of the treated vessel may be made through the guiding catheter or sheath prior to withdrawal of the guidewire. This is desirable.

The embolic protection system of the invention offers considerable clinical advantages. The arrangement allows a clinician to select a suitable guidewire from a range of such guidewires. This provides enhanced flexibility by ensuring that filter performance can be optimized. The embolic protection device is not dedicated to a particular guidewire.

Because the embolic protection device is not attached to the guidewire, the guidewire which is first advanced through a vasculature can have a low profile and be tailored to the proposed procedure or vasculature. Consequently, the guidewire can easily navigate narrow and tortuous regions of the vasculature.

Thus, a clinician may readily select a particular type of guidewire which provides the appropriate flexibility and performance required for a particular vascular procedure being performed. The system also facilitates the safe crossing of a lesion not only in a first lesion.

Another important advantage is that because the embolic protection device is not attached to the guidewire, if the embolic protection device is undersized with respect to the region of the treatment site it is free to be carried by blood flow to a distal narrowed section of the vasculature at which the embolic protection device effectively achieves apposition with the vessel wall. This ensures that all blood flow with entrained embolic material passes through the embolic protection device. The guidewire distal stop prevents movement of the embolic protection device distally off the guidewire.

The possibility of successfully achieving filter deployment at the intended site is significantly improved due to:
 Initial crossing with a bare guidewire is easier as a bare guidewire has an extremely low profile, is highly trackable and highly pushable.
 Attempted crossing with a bare guidewire presents a very low risk of an embolic event due to its low profile, and atraumatic tip.
 Once the bare wire is across the lesion, crossing with the filter delivery system is simplified. Advancing the tip of the guidewire and positioning it in the distal vasculature provides additional support to the filter delivery catheter.

The possibility of successfully delivering other catheters and interventional devices to the lesion area is enhanced because of the independent movement compatibility of the deployed filter, and guidewire. The guidewire tip can be advanced into the distal vasculature to provide anchorage during the advancement of additional catheters and devices. The filter position is maintained by visual apposition and blood flow forces. In this configuration the wire provides extra support to the catheter or interventional device being advanced. This increases the possibility of delivering the catheter to the intended location and minimizes the possibility of an uncontrolled proximal movement of the guidewire/filter. This uncontrolled proximal movement occurs when the guidewire has insufficient support to guide an advancing catheter, through a tortuous path. With fixed wire systems the filter may be quickly withdrawn back into the lesion area with increased, risk of an embolic event or stent dislodgement. The design of this invention substantially eliminates some of these serious clinical risks.

Referring now to FIGS. 48 to 56 there is illustrated other embolic protection devices which are similar to the embolic protection device of FIGS. 1 to 47, and similar elements are assigned the same reference numerals in FIGS. 48 to 56.

In the case of the embolic protection devices of FIGS. 48 to 51 the lumen 56 of the sleeve 43 is of a diameter greater than the outer diameter of the pushing device distal stop 72, and greater than the diameter of the guidewire distal stop 101. Thus, the distal end 49 of the sleeve 43 is not engageable with either the distal stop 72 of the pushing device 8 or the distal stop 101 of the guidewire 99. Instead an engagement grip 130 is provided on an inner wall of the sleeve 43, the engagement grip 130 providing an abutment for engagement with the distal stop 72 of the pushing device 8, and for engagement with the distal stop 101 of the guidewire 99.

Figure 48:
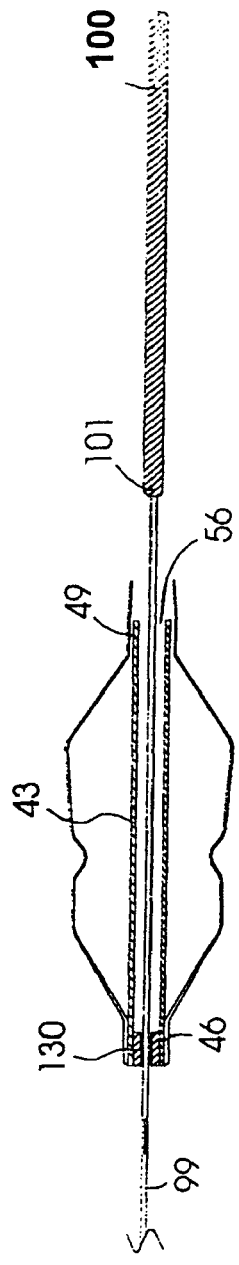
Figure 49:
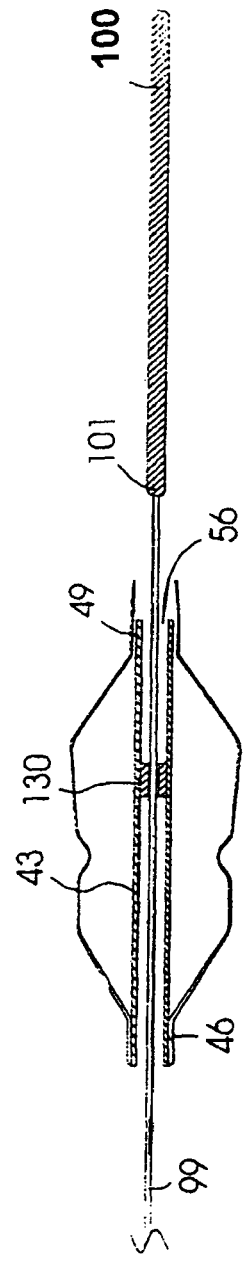
Figure 50:
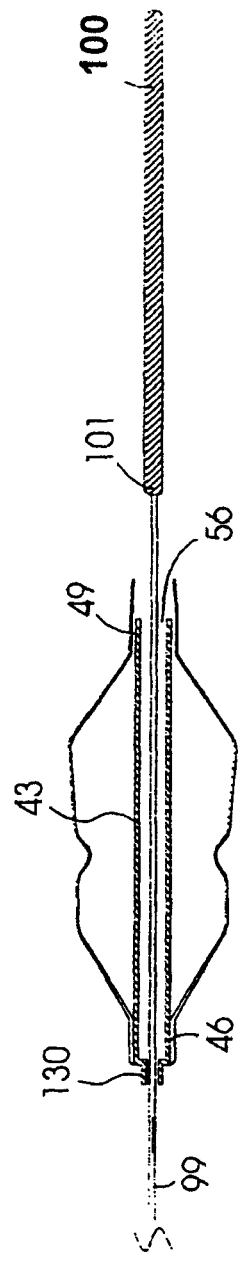
Figure 51:
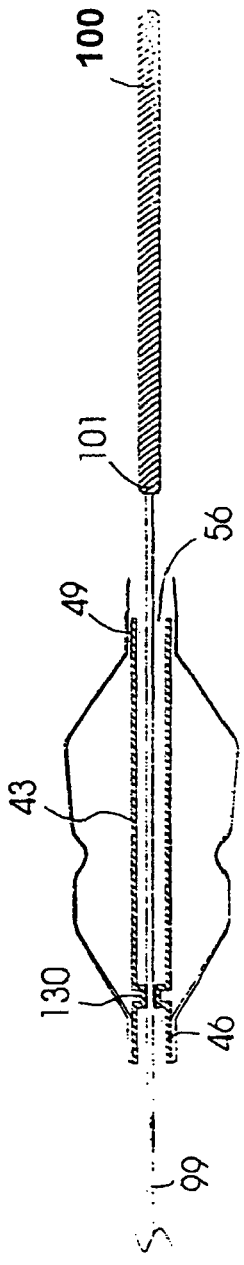

The engagement grip 130 may be provided at the proximal end 46 of the sleeve 43 (FIGS. 48 and 50) or at the distal end 49 of the sleeve 43, or at any suitable point along the length of the sleeve 43 as desired (FIGS. 49 and 51).

The engagement grip 130 may be provided by a relatively short stop rigidly attached to the inner wall of the sleeve 43, as illustrated in FIGS. 48 and 49, for example by chemical means, such as an adhesive, or by mechanical means, such as welding, or brazing, or soldering, or keying means.

Alternatively the engagement grip 130 may be provided by crimping a portion of the sleeve 43, as illustrated in FIGS. 50 and 51.

in the case of FIGS. 52 to 54, the distal end 49 of the sleeve 43 is engageable with the distal stop 72 of the pushing device 8, and the distal stop 101 of the guidewire 99. However, the sleeve 43 does not extend along the length of the filter body 41 as far distally as in the embolic protection device of FIGS. 1 to 51. The sleeve 43 may terminate close to the distal end 47 of the filter body 41 (FIG. 52), or close to the proximal end 44 of the filter body 41 (FIG. 54), or at any suitable point along the filter body 41 (FIG. 53).

In the case of FIGS. 55 and 56, a distal portion of the lumen 56 of the sleeve 43 is of a diameter greater than the outer diameter of the pushing device distal stop 72, and greater than the diameter of the guidewire distal stop 101, and a proximal portion of the lumen 56 of the sleeve 43 is of a smaller diameter to facilitate engagement of the distal stop 72 of the pushing device 8 and engagement of the distal stop 101 of the guidewire 99 with a step 140 in the sleeve 43. The step 140 may be provided by overlapping a small diameter sleeve with a large diameter sleeve (FIG. 55), or alternatively the step 140 may be provided integral with the sleeve 43 for example by machining the step 140 into the sleeve 43.

Figure 57:
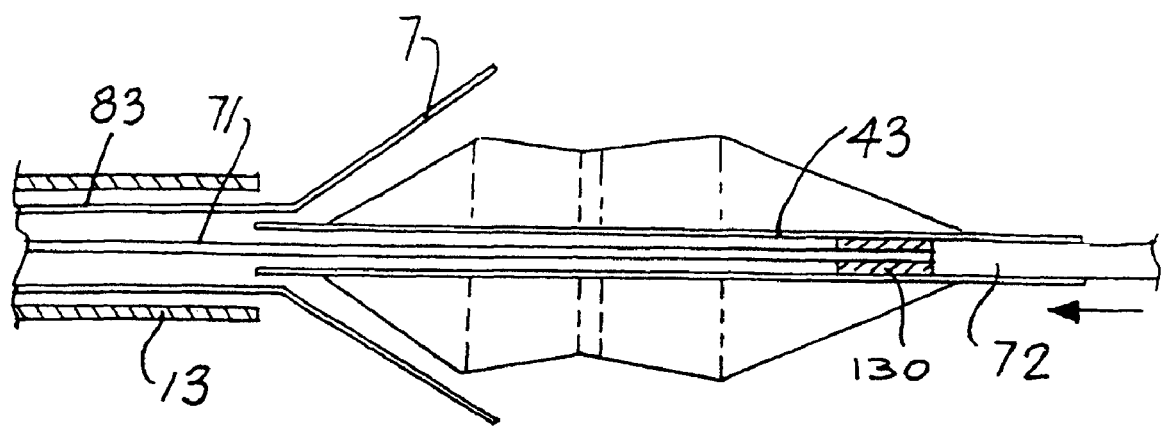
FIGS. 57 and 58 are schematic views illustrating loading of embolic protection devices into the catheter assembly of FIGS. 13 to 17.

Referring to FIG. 57 there is illustrated the loading of an embolic protection device, which is similar to that illustrated above in FIG. 49, into the pod 13 at the distal end 12 of the delivery catheter 2. The loading procedure is similar to that described above with reference, in particular, to FIGS. 28 to 34. In the case of FIG. 57, the distal stop 72 on the pushing device 8 engages the engagement grip 130 on the inner wall of the sleeve 43 to push the embolic protection device through the loading device 7 and into the delivery catheter reception space, thereby collapsing the embolic protection device, as described previously.

Figure 58:
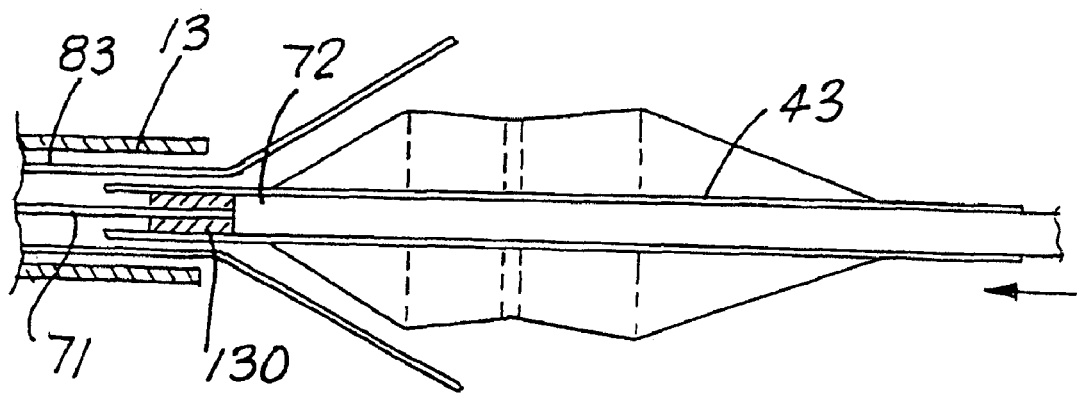
Figure 59:
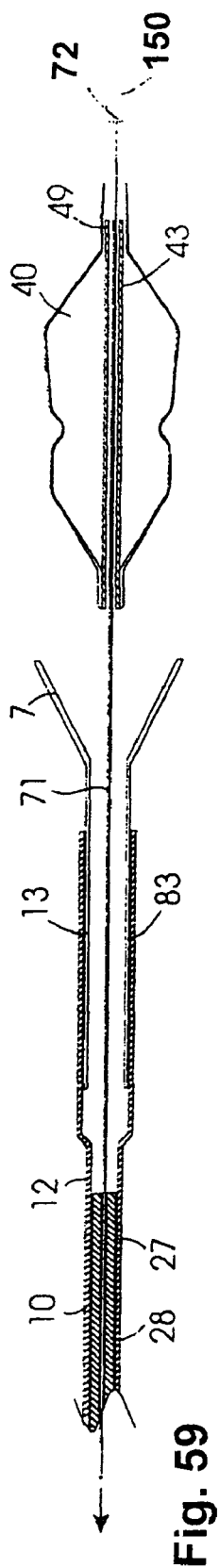
FIGS. 59 to 61 are schematic views illustrating loading of the embolic protection device of FIGS. 18 and 19 into the catheter assembly of FIGS. 13 to 17 using a removable pulling device.
Figure 60:
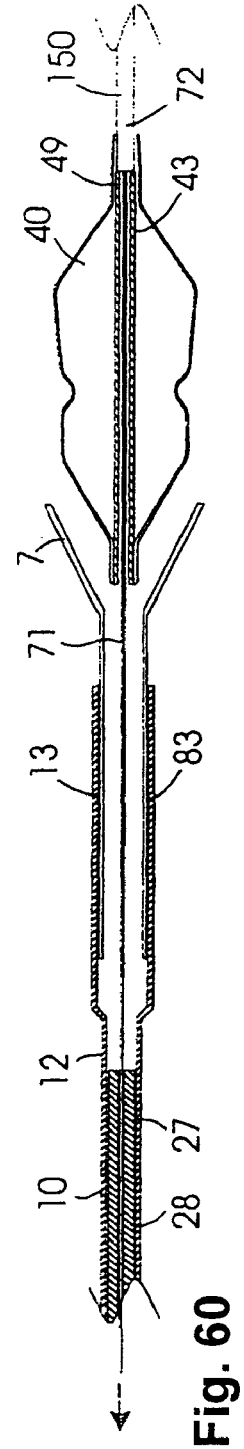
Figure 61:
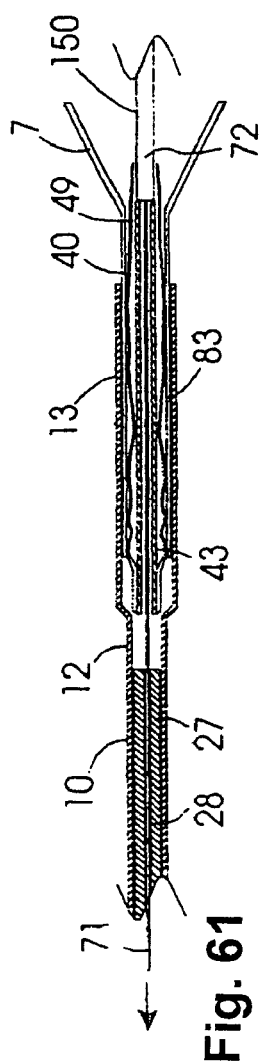
Figure 62:
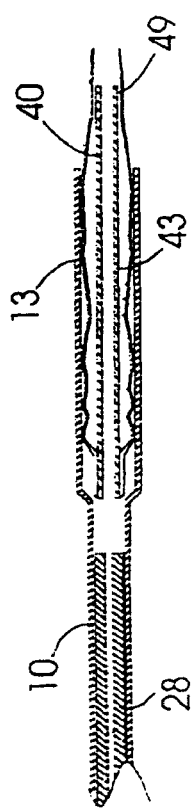
FIG. 62 is a side view of the loaded catheter assembly.

FIG. 58 illustrates the loading of an embolic protection device, which is similar to that illustrated above in FIG. 48, into the pod 13 of the delivery catheter 2.

It will be appreciated that the engagement grip 130 may be of any suitable configuration that facilitates engagement with the distal stop 72 of the pushing device 8 for loading the embolic protection device into the pod 13 of the delivery catheter 2.

Referring to FIGS. 59 to 62 there is illustrated an alternative loading of the filter element 40 into the pod 13 at the distal end 12 of the delivery catheter 2, which is similar to the loading procedure described above with reference, in particular, to FIGS. 28 to 36. In this case, a pulling device 150 is provided in place of the pushing device 8. The pulling device 150 is similar to the pushing device 8 described above, in particular with reference to FIGS. 20 and 21. However, the wire 71 of the pulling device 150 extends proximally through the inner catheter 25, and out of the proximal opening 34 of the catheter for manipulation by a user.

The filter element 40 is loaded by pulling the pulling device 150 proximally to engage the distal stop 72 of the pulling device 150 with the distal end 49 of the sleeve 43. Further pulling of the pulling device 150 draws the filter element 40 through the loading device 7 and into the pod 13 at the distal end 12 of the delivery catheter 2, thereby collapsing the filter element 40, in a manner similar to that described previously. Further pulling of the pulling device 150 proximally disassociates the loaded catheter assembly from the loading device 7 (FIG. 62), as described previously.

Figure 63:
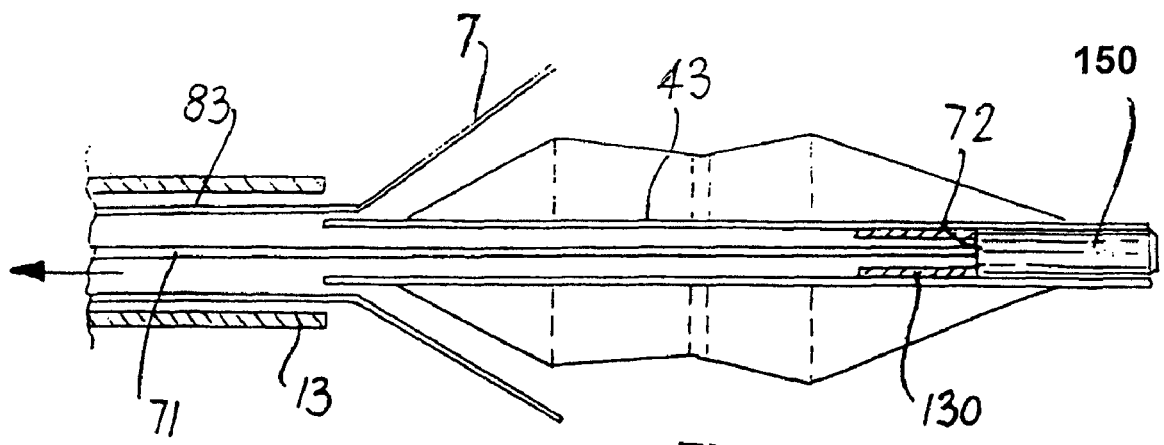
FIGS. 63 and 64 are schematic views illustrating loading of embolic protection devices into the catheter assembly of FIGS. 13 to 17 using the pulling device of FIGS. 59 to 61.

Referring to FIG. 63 there is illustrated the loading of an embolic protection device, which is similar to that illustrated above in FIG. 49, into the pod 13 at the distal end 12 of the delivery catheter 2. The loading procedure is similar to that described above in FIGS. 59 to 62. In the case of FIG. 63, the distal stop 72 of the pulling device 150 engages the engagement grip 130 on the inner wall of the sleeve 43 to pull the embolic protection device through the loading device 7 and into the delivery catheter reception space, thereby collapsing the embolic protection device.

Figure 64:
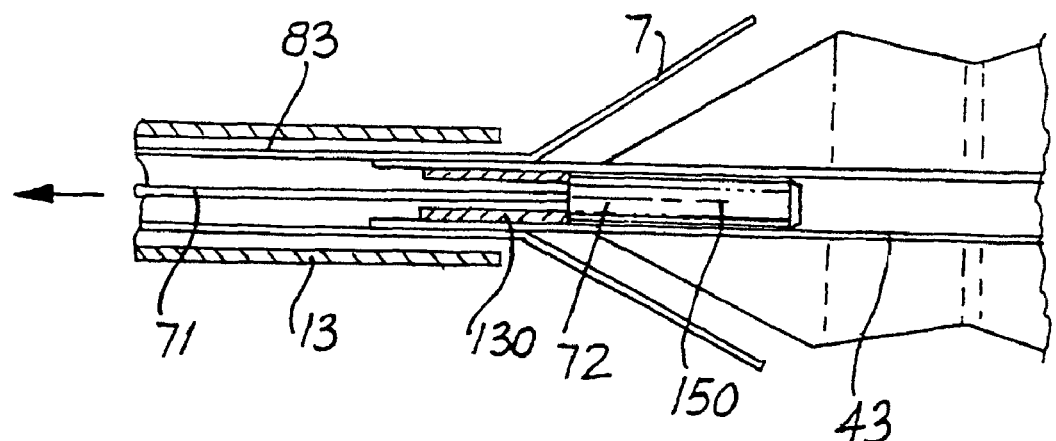
Figure 65:
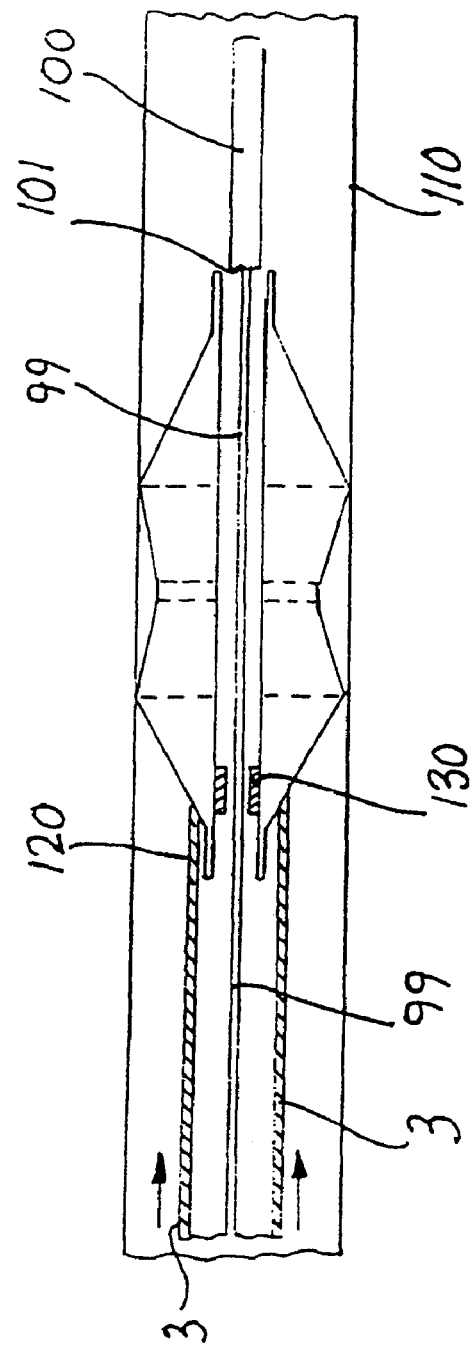
FIGS. 65 to 69 are schematic views illustrating retrieval of an embolic protection device from a vasculature.
Figure 66:
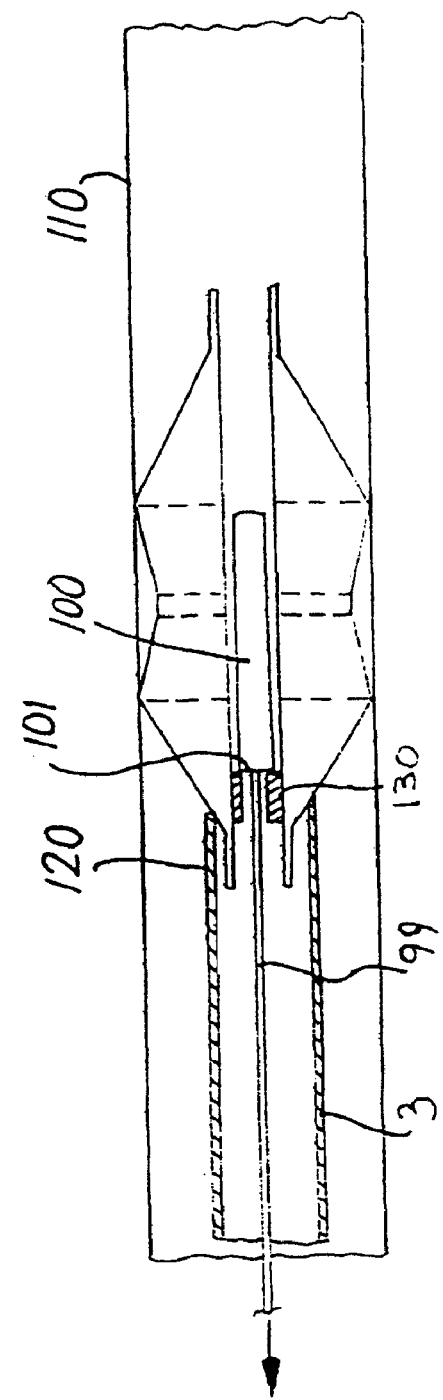
Figure 67:
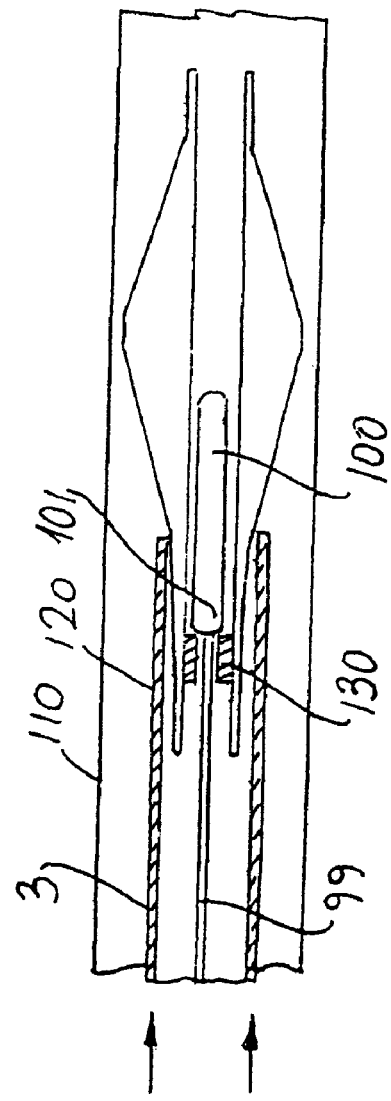
Figure 68:
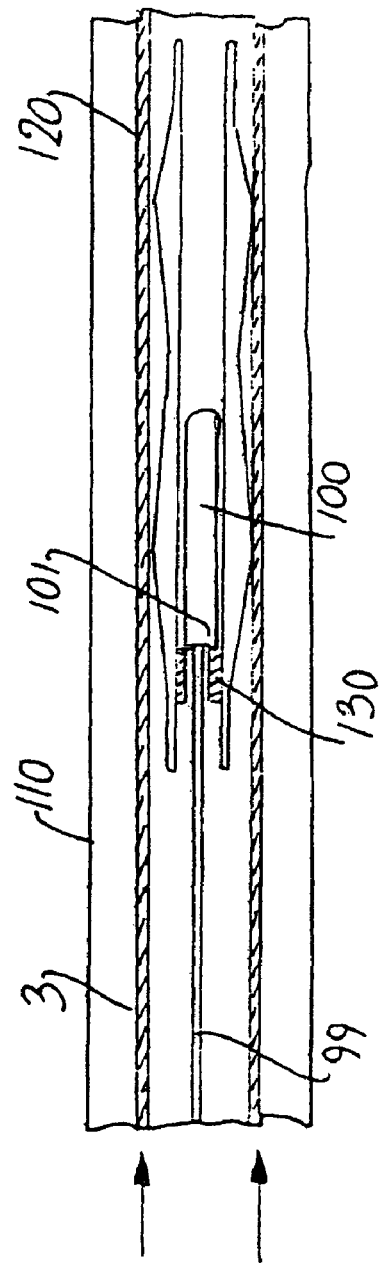

FIG. 64 illustrates the loading of an embolic protection device, which is similar to that illustrated above in FIG. 48, into the pod 13 of the delivery catheter 2 using the pulling device 150.

Referring to FIGS. 65 to 69 there is illustrated the retrieval of an embolic protection device, which is similar to that described above in FIG. 48, into the retrieval catheter 3. The retrieval procedure is similar to that described above with reference, in particular, to FIGS. 44 to 47. In this case, the distal stop 101 on the guidewire 99 engages the engagement grip 130 on the inner wall of the sleeve 43 to prevent the embolic protection device moving distally relative to the distal stop 101 on the guidewire 1 during retrieval.

It will be appreciated that the engagement grip 130 may be of any suitable configuration that facilitates engagement with the distal stop 101 of the guidewire 99 for retrieving the deployed embolic protection device into the retrieval catheter 3.

Figure 69:
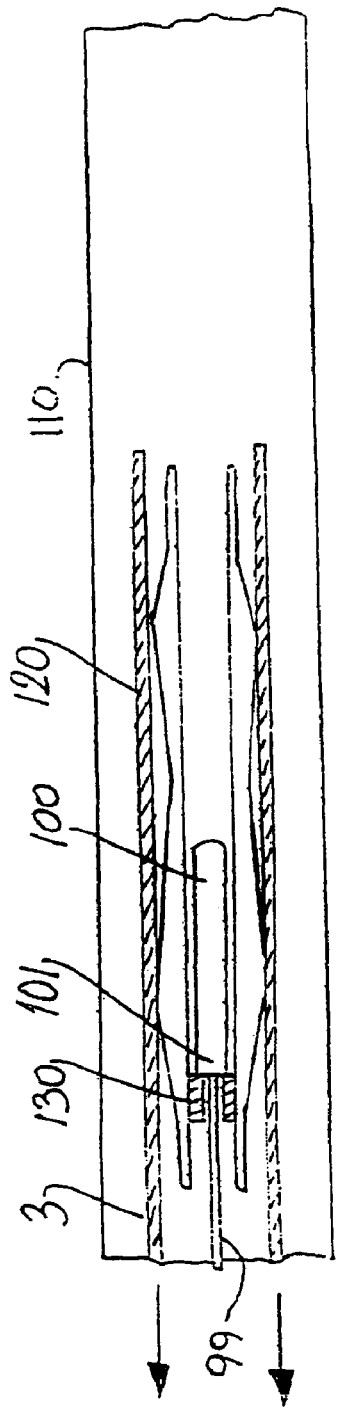
Figure 70:
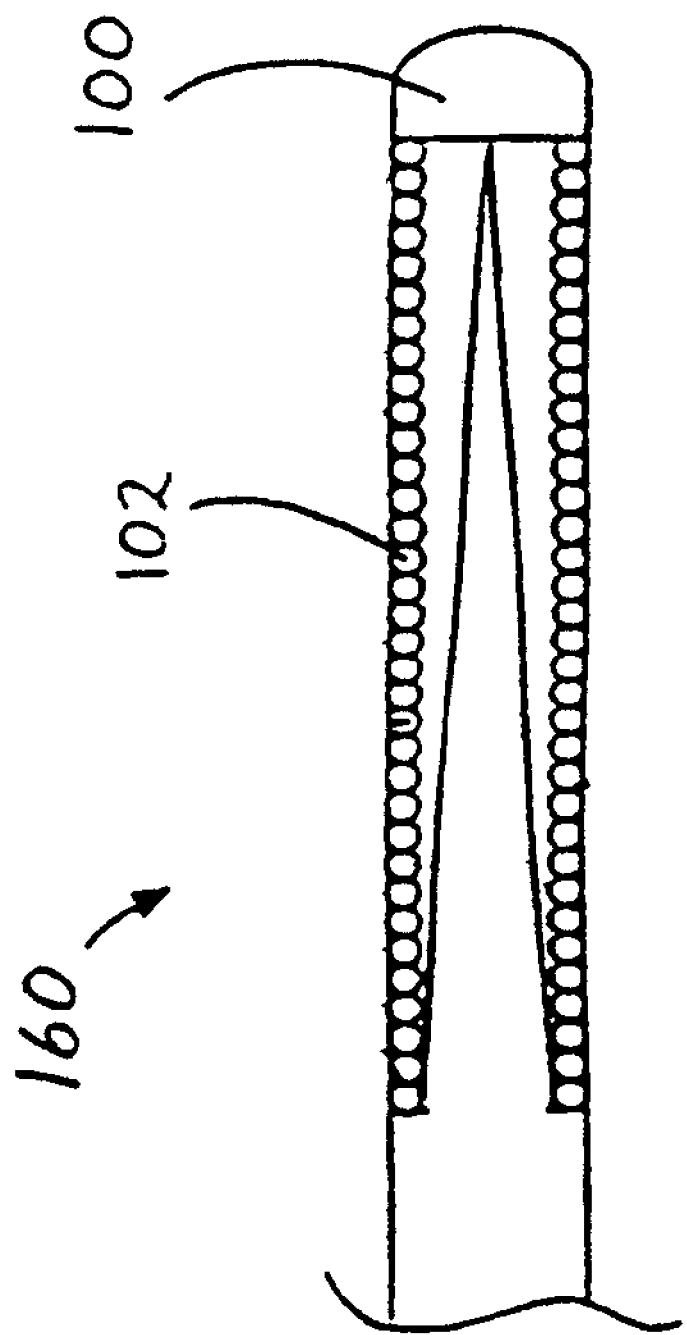
FIG. 70 is a side view of another guidewire of the embolic protection system.

FIG. 70 illustrates another guidewire 160 of the embolic protection system, which is similar to the guidewire 99 of FIGS. 1 to 69, and similar elements are assigned the same reference numerals in FIG. 70. In this case, the guidewire 160 does not comprise a step from a small diameter portion to a large diameter portion.

FIGS. 71 to 74 illustrate the deployment of an embolic protection device of the embolic protection system which has been delivered over the guidewire 160 of FIG. 70. The delivery and deployment procedure is similar to that described above with reference, in particular to FIGS. 36 to 41. In this case, however, a tapered ring 161 is provided slidably mounted on the guidewire 160 between the distal end 27 of the inner stem 28 of the inner catheter 25 and a proximal end 163 of the embolic protection device.

Figure 71:
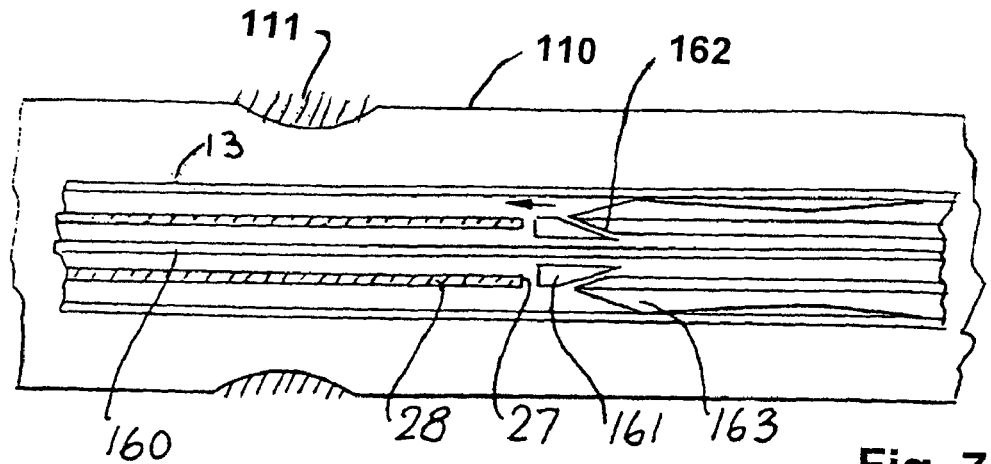
FIGS. 71 to 74 are schematic views illustrating deployment of an embolic protection device in a vasculature.
Figure 72:
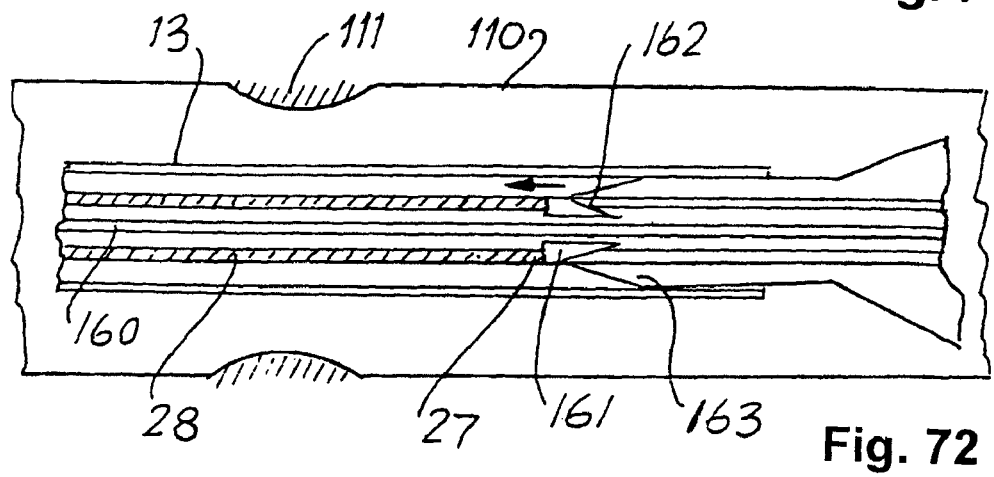
Figure 73:
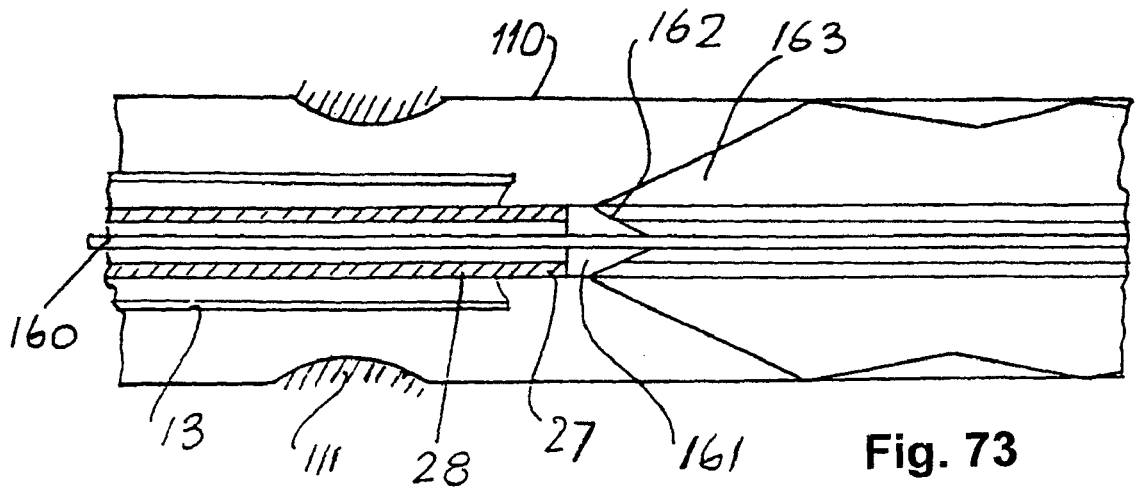
Figure 74:
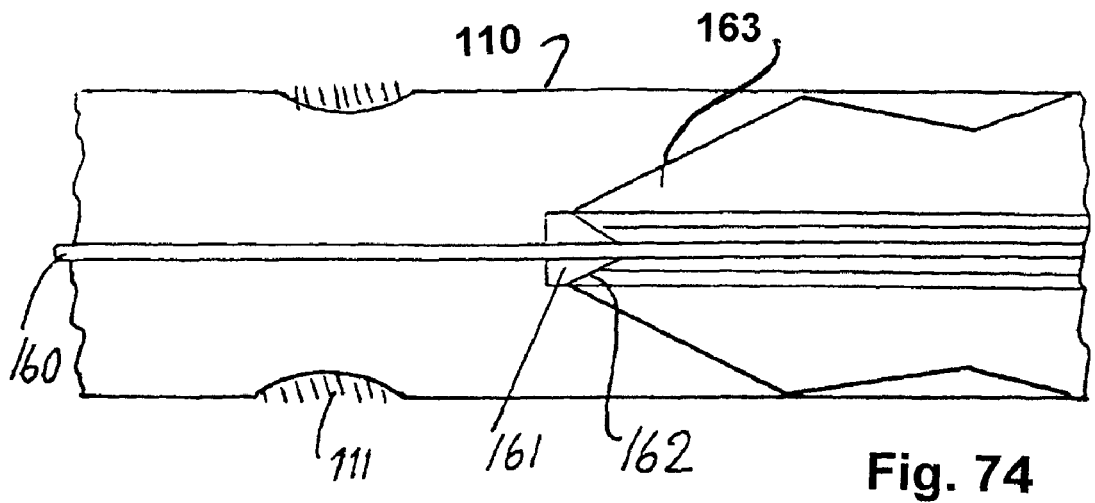

To deploy the embolic protection device at a desired location in the vasculature 110, the delivery catheter 2 is retracted while maintaining the position of the inner catheter 25. The retraction of the delivery catheter 2 initially draws the embolic protection device proximally due to the frictional force acting between the pod 13 of the delivery catheter 2 and the embolic protection device (FIG. 71). As the embolic protection device is initially drawn proximally it abuts the tapered ring and pushes the tapered ring 161 proximally until the tapered ring 161 abuts the distal end 27 of the inner stem 28 of the inner catheter 25 (FIG. 72). Further retraction of the delivery catheter 2 while maintaining the position of the inner catheter 25 causes the embolic protection device and the tapered ring 161 to slide relative to one another along a tapered plane of contact 162. This movement exerts an inward force on the tapered ring 161 to lockingly engage the tapered ring 161 to the guidewire 160. In this way the embolic protection device is taper-locked to the guidewire 160 by means of an interference fit between the embolic protection device, and the tapered ring 161, and by means of an interference fit between the tapered ring 161 and the guidewire 160 (FIG. 73). The delivery catheter 2 and the inner catheter 25 may then be withdrawn from the vasculature 110 to leave the deployed embolic protection device engaged to the bare guidewire 160 in place in the vasculature 110 (FIG. 74).

The embolic protection device is retrieved in a manner similar to that described previously with reference to FIGS. 44 to 47. The retrieval catheter 3 is advanced over the guidewire 160 until the retrieval catheter 3 is proximally adjacent the deployed embolic protection device. The retrieval catheter 3 is then further advanced while maintaining the position of the guidewire 160 to collapse and retrieve the embolic protection device into the retrieval catheter 3. Because the embolic protection device is taper-locked to the guidewire 160 it is not necessary to provide a distal stop on the guidewire 160 for abutment with the embolic protection device. The taper-lock ensures no movement of the deployed embolic protection device distally relative to the guidewire 160 is possible, and thus facilitates retrieval of the embolic protection device into the retrieval catheter 3. The retrieved embolic protection device is then withdrawn from the vasculature 110 by withdrawing the retrieval catheter 3 and the guidewire 160 together.

Figure 75:
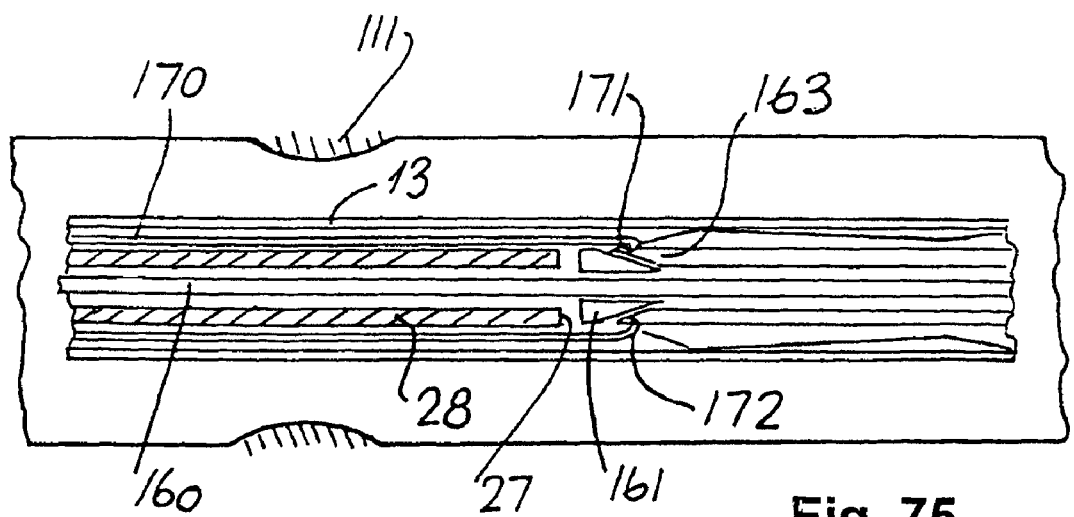
FIGS. 75 and 76 are schematic views illustrating deployment of another embolic protection device in the vasculature using tethers.
Figure 76:
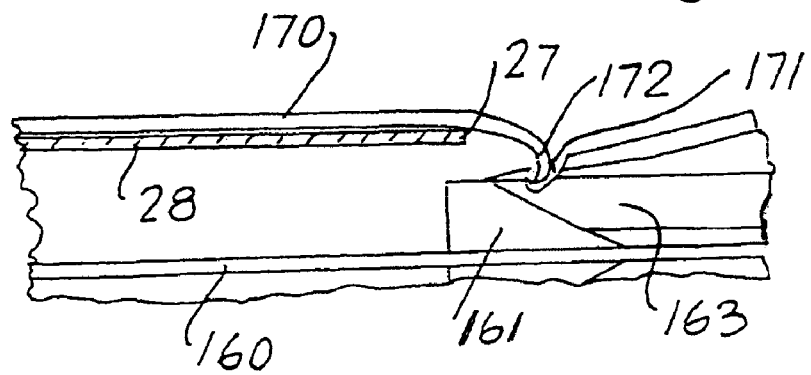
Figure 77:
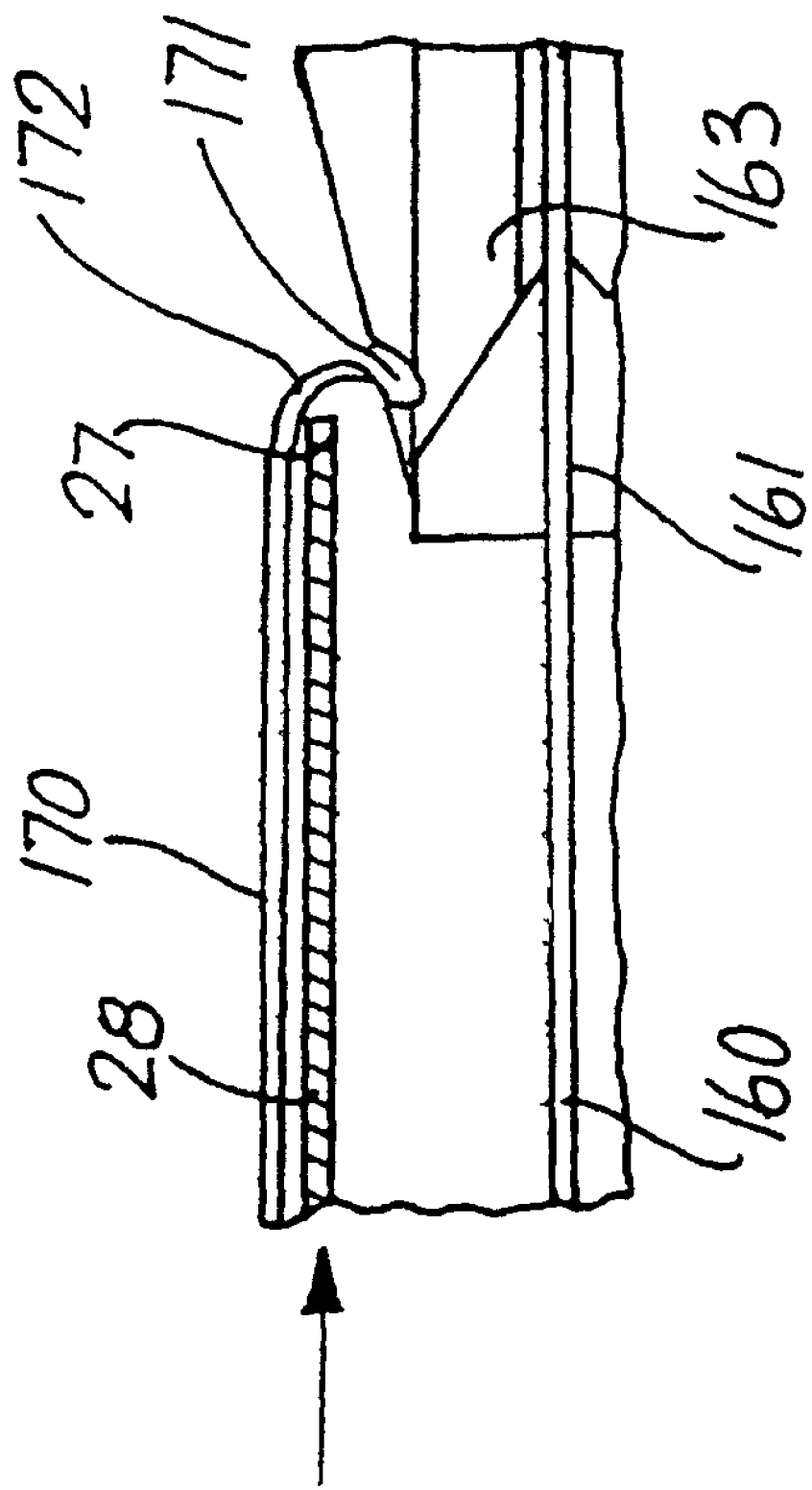
FIG. 77 is a schematic view illustrating release of a tether of FIGS. 75 and 76.

Referring to FIGS. 75 to 77 there is illustrated an embolic protection system which is similar to the embolic protection system described above with reference to FIGS. 71 to 74, and similar elements are assigned the same reference numerals in FIGS. 75 to 77. In this case the embolic protection system comprises two tethers 170 with inwardly arcing hooks 172 at distal ends of the tethers 170, the tethers 170 extending between the inner catheter 25 and the delivery catheter 2. The embolic protection device comprises co-operating recesses 171 in the proximal end 163 of the embolic protection device for receiving the tether hooks 172, as illustrated in FIG. 76.

Deployment of the embolic protection device proceeds in a manner similar to that described above with reference to FIGS. 71 to 74. During retraction of the delivery catheter 2, the tethers 170 are also retracted to ensure that the embolic protection device is drawn proximally to effect a secure taper-lock of the embolic protection device to the guidewire 160 (FIG. 76). The tethers 170 act in addition to the frictional force between the pod 13 of the delivery catheter 2 and the embolic protection device to draw the embolic protection device proximally.

After deployment and taper-locking of the embolic protection device, the hooks 172 of the tethers 170 are unclipped by advancing the inner catheter 25 (FIGS. 76 and 77). The distal end 27 of the inner stem 28 of the inner catheter 25 engages the hooks 172 and levers the hooks 172 outwardly disengaging the hooks 172 from the co-operating recesses 171 (FIG. 77). The tethers 170 and the inner catheter 25 are then withdrawn from the vasculature 110 to leave the deployed embolic protection device in place in the vasculature 110 taper-locked to the bare guidewire 160.

Figure 78:
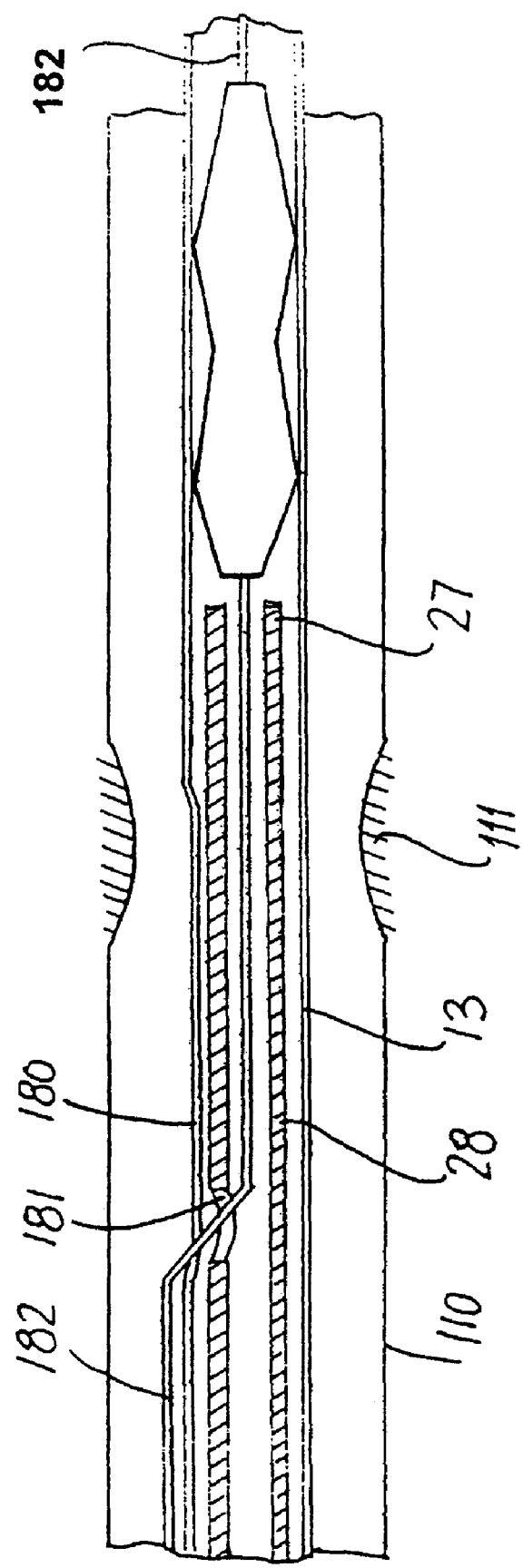

Referring to FIGS. 78 to 81 there is illustrated a rapid exchange embolic protection system which is similar to the embolic protection systems of FIGS. 1 to 77, and similar elements are assigned the same reference numerals in FIGS. 78 to 81. In this case, the pod 13 of the delivery catheter 2 comprises an elongate slit 180 and the inner stem 28 of the inner catheter 25 comprises a rapid exchange aperture 181 for passage of a guidewire 182 through the aperture 181 and the slit 180 (FIG. 78).

The embolic protection device is delivered to a desired location in the vasculature 110 distally of the stenosed region 111 (FIG. 78) in a manner similar to that described previously with reference to FIGS. 36 and 37. The embolic protection device is deployed by retracting the delivery catheter 2 while maintaining the position of the inner catheter 25 (FIGS. 79 to 81), which facilitates deployment of the embolic protection device in a manner similar to that described previously with reference to FIGS. 38 and 39.

The slit 180 in the pod 13 of the delivery catheter 2 is aligned with the rapid exchange aperture 181 in the stem 28 of the inner catheter 25 to prevent occlusion of the rapid exchange aperture 181 during the relative movement of the delivery catheter 2 and the inner catheter 25.

The aperture 181 provided in a sidewall of inner stem 28 of inner catheter is preferably located at a position along the length of the inner catheter which is spaced a relatively longer distance from the proximal end of the catheter than from the distal end of the catheter. Additionally, delivery catheter 2 desirably incorporates an elongate slit 180 which is located adjacent the distal end the catheter and co-operates with aperture 181 and the guide wire 182 which exits therethrough to facilitate a rapid exchange of the catheter and filter assembly over the guide wire, thereby promoting ease of exchange without the necessity of utilizing exchange wires or extension wires. As illustrated in FIGS. 78-81, this arrangement permits use of rapid exchange wire techniques as well as controlled deployment and retrieval of the filter at the delivery pod portion 13 located at the distal end of delivery catheter 2.

This is advantageous in that it facilitates single operator use. A shorter guidewire may be used than for conventional systems making the device less cumbersome.

Referring now to FIG. 82 there is illustrated another embolic protection system 200 according to the invention. The system is similar to these described above and like parts are assigned the same reference numerals. In this case the guidewire 99 includes a proximal stop provided by a step 201 and the filter has a proximal engagement element provided by integral projections 202 which extend radially inwardly. The projections 202 are configured to pass over the proximal step 201 when the filter element is being moved distally over the guidewire 99 for deployment but are prevented from moving proximally over the proximal step 201. Thus, the filter element, on deployment can move between the proximal and distal stops on the guidewire. The arrangement may allow the filter to be retrieved over the proximal step 202.

Referring to FIG. 83 there is illustrated a system 205 similar to that of FIG. 82 and like parts are assigned the same reference numerals. In this case the proximal step on the guidewire is provided by a proximally tapering element 206.

The embolic protection device is not restricted to use with a particular guidewire because it is not attached or engaged with the guidewire in any way as it is advanced over the guidewire. This is a highly advantageous arrangement. If the guidewire proves unsuitable for some reason, for example because it is too large or not trackable enough to access a desired site in a vascular system, the guidewire may be replaced with a more suitable guidewire, for example a guidewire with greater flexibility. However, because the embolic protection device is independent of the guidewire it may be used with any suitable guidewire.

The invention gives greater freedom to a user by providing a choice of guidewires to suit a patient anatomy without requiring the user to select the embolic protection device to be used with the guidewire until after successful crossing of a lesion with the guidewire.

Numerous vascular catheter functions are facilitated by the invention, such as:

(i) Permits Dye Injections:

After performing a therapeutic procedure (e.g. angioplasty or atherectomy), the embolic protection device can be retrieved if desired, in order to inject dye (over the remaining guidewire), such that minimal obstruction or interference occurs with the subsequent dye flow measurements. Alternatively, the wire can also be safely partially-retracted "behind" or "upstream" of the treated area, prior to performing the dye injection.

(ii) Delivery of Lytic Agents:

Depending upon therapeutic needs, lytic agents can be site-specifically delivered to a region of interest, either with the embolic protection device deployed, or with the embolic protection device retrieved, if desired.

(iii) Facilitates Guidewire Replacements:

Assuming appropriate design considerations have been incorporated; the retrieval sheath can also facilitate safe removal of the embolic protection device following a stenting procedure. For example, after deployment of an intravascular stent, the process of removing the embolic protection device favors certain sheath designs, such as a tapered distal tip. Specifically, the distal tip of the sheath needs to permit easy crossing of the stent in a manner which will not catch up or "snag" at the proximal edge of the implanted stem, nor along any inwardly-projecting surface of the interior of the implanted stent, as the sheath is being introduced. More specifically, the distal region of the retrieval sheath is also preferably formed of a material which permits radial expansion at the distal tip in order to accommodate retrieval of the embolic protection device.

(iv) Facilitates Guidewire Replacements:

Because this embolic protection system accommodates barewire introduction, it is possible to replace a guidewire during a procedure, if desired. For example, during treatment of two or more, distally spaced-apart lesions, it may become necessary to replace the initial guidewire during the procedure with another guidewire offering improved steering or distal flexibility. The present invention might support such guidewire replacements as follows. First, the embolic protection device is retrieved into the retrieval sheath (which has already crossed the first lesion area). Then the wire can be withdrawn (or alternatively, the wire and embolic protection device together can be withdrawn), while the sheath remains across the lesion. Subsequently, a replacement guidewire can be introduced through the sheath lumen to the area of interest.

Figure 84:
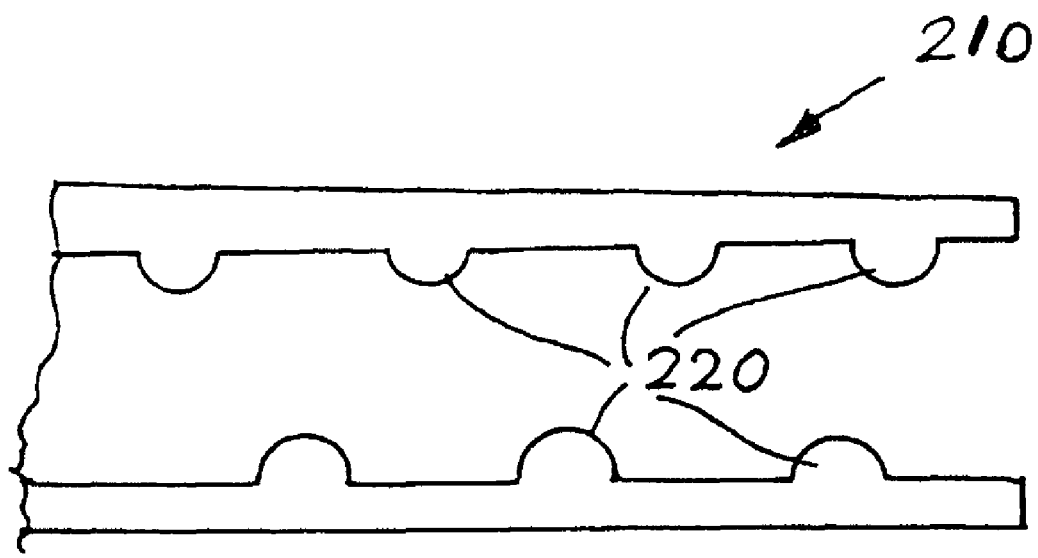
FIGS. 84 and 85 are cross-sectional views of a distal portion of catheters.
Figure 85:
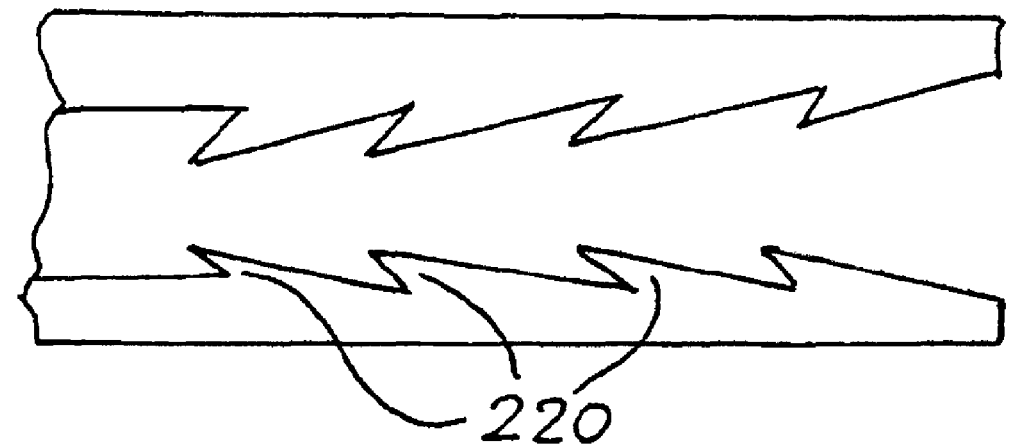

A number of engagement means between the embolic protection device and the guidewire are described above which ensure that the embolic protection device is anchored or tethered while the retrieval sheath is advanced over the embolic protection device. It is also envisaged that an engagement means may be provided between the embolic protection device and the retrieval sheath after the filter is retrieved, to ensure that there is a positive engagement between the embolic protection device and the sheath. For example, frictional engagement means may be provided on one or both of the embolic protection device and sheath. For example, projections, rings, or the like may be provided on the inner surface of the retrieval sheath adjacent the distal end thereof to provide a frictional fit with the retrieved embolic protection device. Typical arrangements 210; 220 of this type are illustrated in FIGS. 84 and 85. The frictional engagement may be provided by projections 225 which may be of any type including continuous, discontinuous, radially and/or longitudinally extending.

The invention is not limited to the embodiments hereinbefore described, which may be varied in construction and detail.

What is claimed is:

1. A method of providing embolic protection, comprising:
   delivering a guidewire through a vascular system of a patient;
   delivering a filter element on the guidewire to a location within a blood vessel that is distal to a treatment location, the filter element being delivered in a collapsed stored position for movement through the vascular system;
   expanding the filter element to an expanded position in which the filter element at least partially contacts a wall of the blood vessel such that blood passing through the blood vessel is delivered through the filter element but embolic material in the blood is retained in the filter element, and the guidewire is slidable relative to the entire filter element when the filter element is in the expanded position;
   delivering an interventional device to the treatment location while the filter is in the expanded position, the interventional device being directly engaged with the guidewire in vivo;
   performing an interventional procedure at the treatment location;
   advancing a retrieval catheter over the filter element;
   at least partially collapsing the filter element; and
   withdrawing the retrieval catheter and filter element from the blood vessel,
   wherein the filter element comprises a collapsible filter body and a collapsible filter support frame, the filter body having a proximal inlet end and a distal outlet end, the inlet end of the filter body having one or more large inlet openings, and the outlet end of the filter body having a plurality of small outlet openings sized to allow through passage of blood but to retain undesired embolic material within the filter body.

2. The method of providing embolic protection of claim 1, further comprising delivering lytic agents within the blood vessel.

3. The method of providing embolic protection of claim 2, wherein the lytic agents are delivered after the retrieval catheter and the filter element have been withdrawn.

4. The method of providing embolic protection of claim 2, wherein the lytic agents are delivered while the filter element is deployed at the location distal to a treatment location.

5. The method of providing embolic protection of claim 1, wherein the interventional procedure is an angioplasty procedure.

6. The method of providing embolic protection of claim 1, wherein the interventional procedure is an arthrectomy procedure.

7. The method of providing embolic protection of claim 1, wherein the interventional procedure is a stenting procedure.

8. The method of providing embolic protection of claim 2, wherein the interventional procedure is an angioplasty procedure.

9. The method of providing embolic protection of claim 2, wherein the interventional procedure is an arthrectomy procedure.

10. The method of providing embolic protection of claim 2, wherein the interventional procedure is a stenting procedure.

* * * * *